(12) United States Patent
Wang et al.

(10) Patent No.: US 8,041,515 B2
(45) Date of Patent: *Oct. 18, 2011

(54) USE OF IMPEDANCE-BASED CYTOLOGICAL PROFILING TO CLASSIFY CELLULAR RESPONSE PROFILES UPON EXPOSURE TO BIOLOGICALLY ACTIVE AGENTS

(75) Inventors: Xiaobo Wang, San Diego, CA (US); Yama A. Abassi, San Diego, CA (US); Wen fu Zhang, San Diego, CA (US); Xiao Xu, San Diego, CA (US)

(73) Assignee: Acea Biosciences, Inc., San Diego, CA (US)

( * ) Notice: Subject to any disclaimer, the term of this patent is extended or adjusted under 35 U.S.C. 154(b) by 873 days.

This patent is subject to a terminal disclaimer.

(21) Appl. No.: 11/903,454

(22) Filed: Sep. 20, 2007

(65) Prior Publication Data
US 2008/0124703 A1 May 29, 2008

Related U.S. Application Data

(60) Provisional application No. 60/846,067, filed on Sep. 20, 2006.

(51) Int. Cl.
G06F 19/00 (2011.01)
C12Q 1/02 (2006.01)
C12M 1/42 (2006.01)

(52) U.S. Cl. .......................... 702/19; 435/29; 435/285.2
(58) Field of Classification Search .................... None
See application file for complete search history.

(56) References Cited

U.S. PATENT DOCUMENTS

| | | | |
|---|---|---|---|
| 2,656,508 A | 10/1953 | Coulter | |
| 3,259,842 A | 7/1966 | Coulter et al. | |
| 3,743,581 A | 7/1973 | Cady et al. | |
| 3,890,201 A | 6/1975 | Cady | |
| 4,072,578 A | 2/1978 | Cady et al. | |
| 4,225,410 A | 9/1980 | Pace | |
| 4,686,190 A | 8/1987 | Cramer et al. | |
| 4,920,047 A | 4/1990 | Giaever et al. | |
| 5,001,048 A | 3/1991 | Taylor et al. | |
| 5,134,070 A | 7/1992 | Casnig | |
| 5,187,096 A | 2/1993 | Giaever et al. | |
| 5,218,312 A | 6/1993 | Moro | |
| 5,247,827 A | 9/1993 | Shah | |
| 5,278,048 A | 1/1994 | Parce et al. | |
| 5,284,753 A | 2/1994 | Goodwin | |
| 5,514,555 A | 5/1996 | Springer et al. | |
| 5,563,067 A | 10/1996 | Sugihara et al. | |
| 5,601,997 A | 2/1997 | Tchao et al. | |
| 5,622,872 A | 4/1997 | Ribi | |
| 5,626,734 A | 5/1997 | Docoslis et al. | |
| 5,643,742 A | 7/1997 | Malin et al. | |
| 5,766,934 A | 6/1998 | Guiseppi-Elie | |
| 5,801,055 A | 9/1998 | Henderson | |
| 5,810,725 A | 9/1998 | Sugihara et al. | |
| 5,851,489 A | 12/1998 | Wolf et al. | |
| 5,981,268 A | 11/1999 | Kovacs et al. | |
| 6,051,422 A | 4/2000 | Kovacs et al. | |
| 6,132,683 A | 10/2000 | Sugihara et al. | |
| 6,169,394 B1 | 1/2001 | Frazier et al. | |
| 6,232,062 B1 | 5/2001 | Kayyem et al. | |
| 6,235,520 B1 | 5/2001 | Malin et al. | |
| 6,280,586 B1 | 8/2001 | Wolf et al. | |
| 6,288,527 B1 | 9/2001 | Sugihara et al. | |
| 6,368,795 B1 | 4/2002 | Hefti | |
| 6,368,851 B1 | 4/2002 | Baumann et al. | |
| 6,376,233 B1 | 4/2002 | Wolf et al. | |
| 6,377,057 B1 | 4/2002 | Borkholder | |
| 6,440,662 B1 | 8/2002 | Gerwen et al. | |
| 6,448,030 B1 | 9/2002 | Rust et al. | |
| 6,448,794 B1 | 9/2002 | Cheng et al. | |
| 6,461,808 B1 | 10/2002 | Bodner et al. | |
| 6,472,144 B2 | 10/2002 | Malin et al. | |
| 6,485,905 B2 | 11/2002 | Hefti | |
| RE37,977 E | 2/2003 | Sugihara et al. | |
| 6,566,079 B2 | 5/2003 | Hefti | |
| 6,573,063 B2 | 6/2003 | Hochman | |
| 6,596,499 B2 | 7/2003 | Jalink | |
| 6,626,902 B1 | 9/2003 | Kucharczyk et al. | |
| 6,627,461 B2 | 9/2003 | Chapman et al. | |

(Continued)

FOREIGN PATENT DOCUMENTS

EP 1138758 A1 4/2001

(Continued)

OTHER PUBLICATIONS

Luan et al. Clustering of time-course gene expression data using a mixed-effects model with B-splines Bioinformatics vol. 19, pp. 474-482 (2003).*
Rabow et al. Mining the National Cancer Insittute's Tumor-Screening Database: Identification of Compounds with Similar Cellular Activities Journal of Medicinal Chemistry vol. 45, pp. 818-840 (2002).*
Xing et al. Dynamic Monitoring of Cytotoxicity on Microeletronic Sensors Chemical Research in Toxicology vol. 18, pp. 154-161 (2005).*
Aravanis et al. Biosensors & Bioelectronics 16:571-577 (2001).
Baumann at al. Sensors & Accuators B55:77-89 (1999).
Becker et al, Cell Biology. 92:960-964 (1995).
Berens et al, Clin. Exp. Metastasis 12:405-415 (1994).
Bergveld, Biosensors & Bioelectronics. 6:55-72 (1991).

(Continued)

*Primary Examiner* — John S Brusca
(74) *Attorney, Agent, or Firm* — Biotech Beach Law Group PC; Raymond Wagenknecht

(57) ABSTRACT

The present invention provides methods of multi-dimensional profiling of biologically active agents and determining their effects on biological systems. The methods of the present invention include real-time impedance monitoring of cellular responses to biologically active agents and categorization of cellular kinetic profiles into mechanism specific cellular response profile groups. The grouping of similar cellular response profiles allows the correlation between agent and mechanism, thus allowing for the identification of potential therapeutic applications of agents or further study of cellular responses or mechanisms.

35 Claims, 41 Drawing Sheets

U.S. PATENT DOCUMENTS

| | | |
|---|---|---|
| 6,630,359 B1 | 10/2003 | Caillat |
| 6,637,257 B2 | 10/2003 | Sparks |
| RE38,323 E | 11/2003 | Sugihara et al. |
| 6,686,193 B2 | 2/2004 | Maher et al. |
| 6,716,620 B2 | 4/2004 | Bashir et al. |
| 6,723,523 B2 | 4/2004 | Lynes et al. |
| 7,192,752 B2 | 3/2007 | Xu et al. |
| 2002/0032531 A1 | 3/2002 | Mansky et al. |
| 2002/0076690 A1 | 6/2002 | Miles et al. |
| 2002/0086280 A1 | 7/2002 | Lynes et al. |
| 2002/0090649 A1 | 7/2002 | Chan et al. |
| 2002/0110847 A1 | 8/2002 | Baumann et al. |
| 2002/0150886 A1 | 10/2002 | Miles et al. |
| 2003/0032000 A1 | 2/2003 | Liu et al. |
| 2003/0072549 A1 | 4/2003 | Facer et al. |
| 2003/0116447 A1 | 6/2003 | Surridge et al. |
| 2003/0143625 A1 | 7/2003 | Martin et al. |
| 2003/0157587 A1 | 8/2003 | Gomez et al. |
| 2003/0166015 A1 | 9/2003 | Zarowitz et al. |
| 2004/0091397 A1 | 5/2004 | Picard |
| 2004/0146849 A1 | 7/2004 | Huang et al. |
| 2004/0152067 A1 | 8/2004 | Wang et al. |
| 2005/0014130 A1 | 1/2005 | Liu et al. |
| 2005/0112544 A1 | 5/2005 | Xu et al. |
| 2005/0213374 A1 | 9/2005 | Xu et al. |
| 2006/0023559 A1 | 2/2006 | Xu et al. |
| 2006/0050596 A1 | 3/2006 | Abassi et al. |
| 2006/0120204 A1 | 6/2006 | Abassi et al. |
| 2006/0121446 A1 | 6/2006 | Abassi et al. |
| 2007/0172939 A1 | 7/2007 | Xu et al. |

FOREIGN PATENT DOCUMENTS

| | | |
|---|---|---|
| EP | 1195432 B1 | 9/2004 |
| EP | 11954323 | 9/2004 |
| WO | 96/01836 | 1/1996 |
| WO | 99/66329 | 12/1999 |
| WO | 00/71669 | 11/2000 |
| WO | 01/25769 | 4/2001 |
| WO | 01/38873 | 5/2001 |
| WO | 02/04943 | 1/2002 |
| WO | 02/42766 | 5/2002 |
| WO | 03/016887 | 2/2003 |
| WO | 2005/005979 | 1/2005 |

OTHER PUBLICATIONS

Bieberich and Guiseppi-Elie, Biosensors and Bioelectronics, 19:923-931 (2004).
Burnett et al., J. Biomo. Screening, 8(6):660-667 (2003).
Burns et al, Journal of Immunology 2893-2903 (1997).
Ciambrone et al., J. Biomo. Screening, 9(6):467-480 (2004).
Connolly et al, Biosensors & Bioelectronics 5: 223-234 (1990).
Duan et al, Anal. Chem. 66:1369-1377 (1994).
Ehret et al, Biosensors and Bioelectronics 12(1):29-41 (1997).
Ehret et al. Medical & Biological Engineering and Computing 36:365-370, (1998).
Falk et al, J. Immunol. Meth. 33:239-247 (1980).
Fuhr et al, Sensors and Materials 7(2):131-146 (1995).
Gaiever et al, Proc. Natl. Acad. Sci 81:3761-3764 (1984).
Giaever et al, Proc. Natl. Acad. USA 88: 7896-7900 (1991).
Gutmann et al, Pharmaceutical Research, 16(3):402-407 (1999).
Hadjout et al., BioTechniques 31: 1130-1138 (2001).
Henning et al, Anti-Cancer Drugs 12:21-32 (2001).
Hidalgo et al, Gastroenterology 96:736-749 (1989).
Huang et al, Anal. Chem. 74:3362-3371 (2002).
Hug, Assay and Drug Dev. Tech., 1(3): 479-488 (2003).
Keese et al, Biotechniques 33:842-850 (2002).
Kleinmann et al, Biochemistry. 26:312-318 (1986).
Kowolenko et al, Journal of Immunological Methods 127: 71-77 (1990).
Larsen et al, Micro Total Analysis Systems 103-106 (2000).
Lin and Huang, J. Micromech. Microeng., 11:542-547 (2001).
Lin et al., Min. For Chem., Bio., & Bioeng., 4:104-108 (2004).
Lo et al, Experimental Cell Research 204:102-109 (1993).
Lo et al, Experimental Cell Research 213: 391-397 (1994).
Lo et al, Biophysical Journal 69: 2800-2807 (1995).
Loffert et al., QIAGENNews, 4:15-18 (1997).
Luong, et al, Analytical Chemistry 73: 1844-1848 (2001).
Mitra et al, Biotechniques 11(4):504-510 (1991).
Miyata et al, Jpn. J. Ophthalmol, 34:257-266 (1990).
Nerurkar et al, Pharmaceutical Research 13(4);528-534, (1996).
Ong et al, Sensors 2:219-222 (2002).
Pancrazio et al, Sensors and Actuators B 53:179-185 (1998).
Patolsky et al, Nature Biotechnology 19:253-257 (2001).
Pethig et al, Appl. Phys. 24:881-888 (1992).
Richards et al, Immunological Communications 13(1):49-62 (1984).
Rishpon et al., Biosensors & Bioelectronics, 12(3):195-204 (1997).
Simpson et al., Trends in Biotechnology 19: 317-323 (2001).
Sohn et al, Proc. Nat. Acad. Sci. 97(20)10687-10690 (2000).
Stenger et al, Trends in Biotechnology 19: 304-309 (2001).
Svetlicic et al, Bioelectrochemistry 53: 79-86 (2000).
Tiruppathi et al, Proc Natl Acad Sci USA 89:7919-7923 (1992).
Wang et al, Appl. Phys. 1649-1660 (1996).
Wang et al, Appl. Phys. 26:1278-1285 (1993).
Wang et al, Anal. Chem. 72:832-839 (2000).
Wang et al, Biophysical Journal 72:1887-1899 (1997).
Wang et al, Biophysical Journal 74:2689-2701 (1998).
Warburg, Ann. Phy. 6:125-135 (1901).
Wegener et al., Eur. J. Physiol., 437:925-934 (1999).
Wolf et al, Biosensors & Bioelectronics 13:501-509 (1998).
Xiao and Luong, Biotechnol. Prog., 19:1000-1005 (2003).
Xiao et al., Anal. Chem., 74:5748-5753 (2002).
Xiao et al, Anal. Chem 74:1333-1339 (2002).
Yamauchi et al., Nuc. Acids Res., 32(22):1-8 (2004).
Yang et al, Anal. Chem. 71:911-918 (1999).
http://www.tecan.com.migration_introl-pdf (1999).
New Products page. Science 298:2409 (2002).
Abstract: Real-Time Impedance Assay to Follow the Invasive Activities of Metastatic Cells in Culture. Biotechniques 33: 842 (2002).
http://www.biophysics.com/pages/front.html, (2002)
Cady et al., Electrical Impedance Measurements: Rapid Method for Detecting and Monitoring Microorganisms.
Mohr et al., Performance of a thin film microelectrode array for monitoring electrogenic cells in vitro, Sensors and Actuators B34:265-269. 1996.
Wegner et al. Electric Cell-Substrate Impedance Sensing (ECIS) as a Noninvasive Means to Monitor the Kinetics of Cell Spreading to Artificial Surfaces. Experimental Cell Research 259, 158-166 (2000).
Slaughter et al., International Joint Conference on Neural Networks, ICJN '06, Jul. 15, 2006, pp. 2001-2008.

* cited by examiner

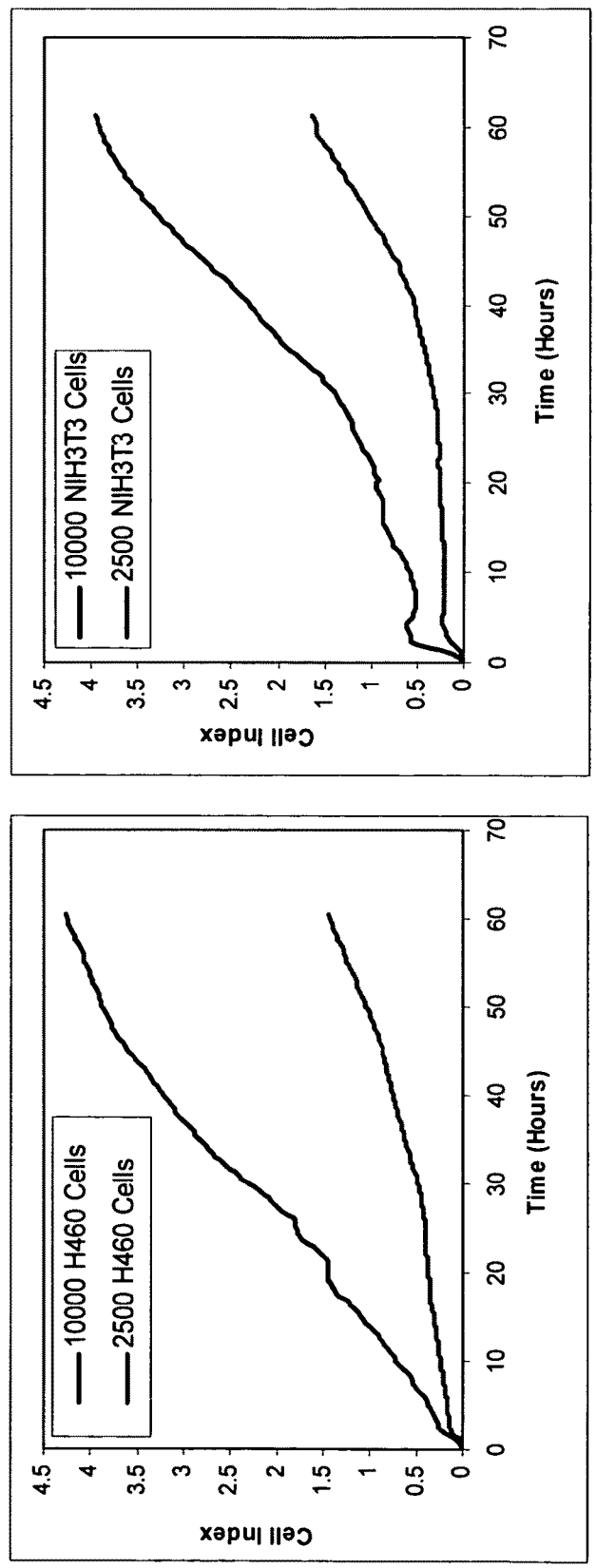
FIG. 3A: Panel 1

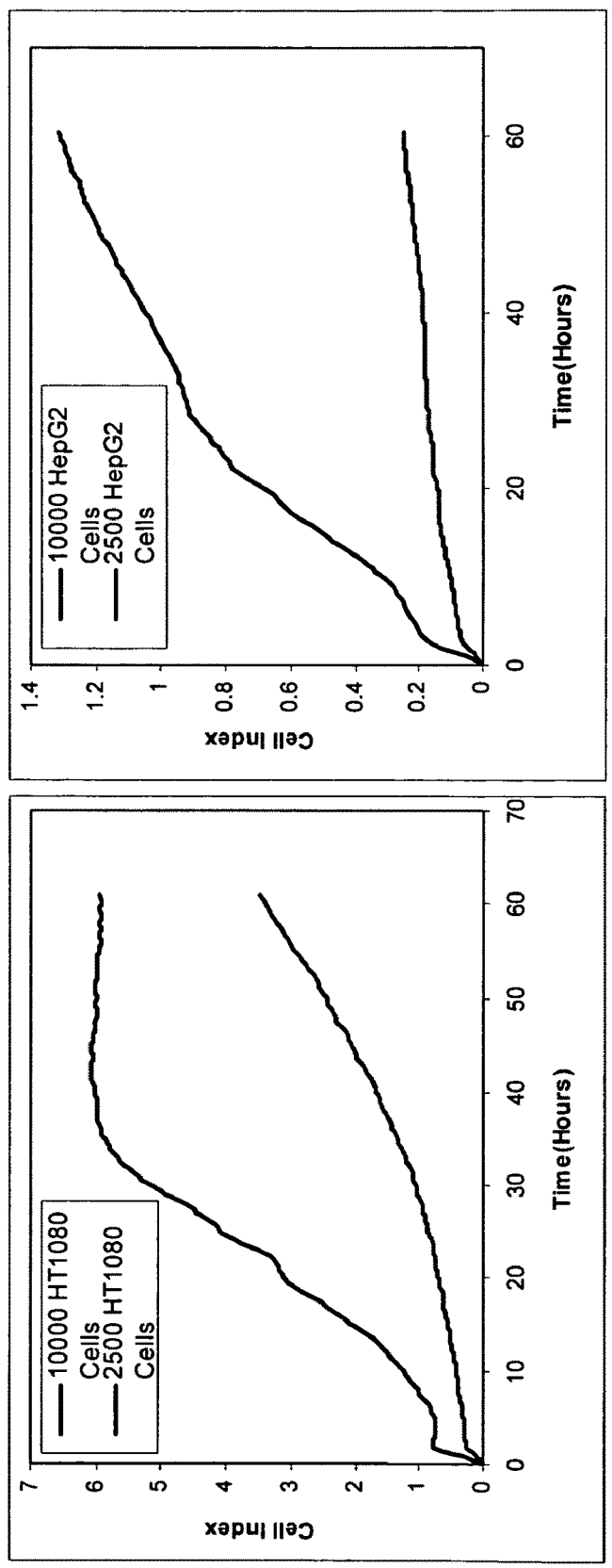
FIG. 3B: Panel 2

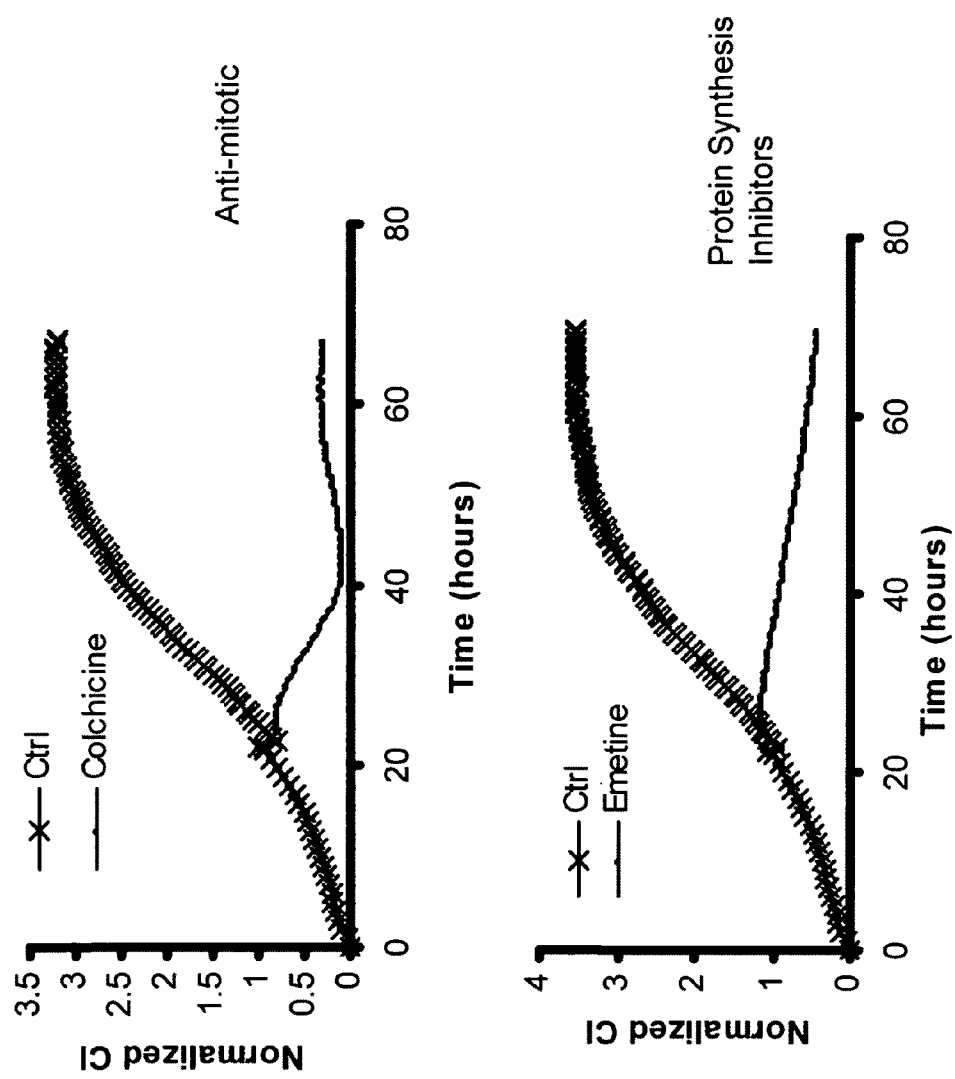
FIG. 5A: Panel 1

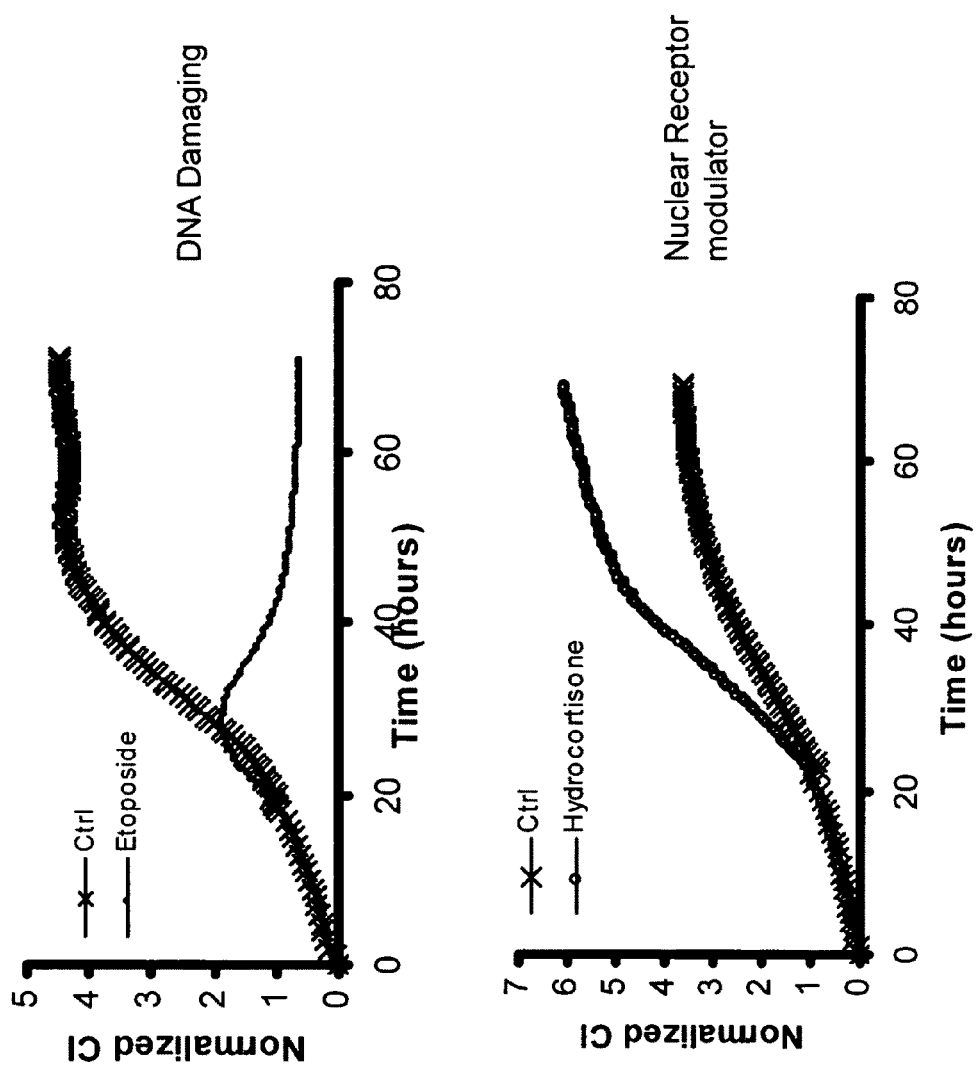
FIG. 5B: Panel 2

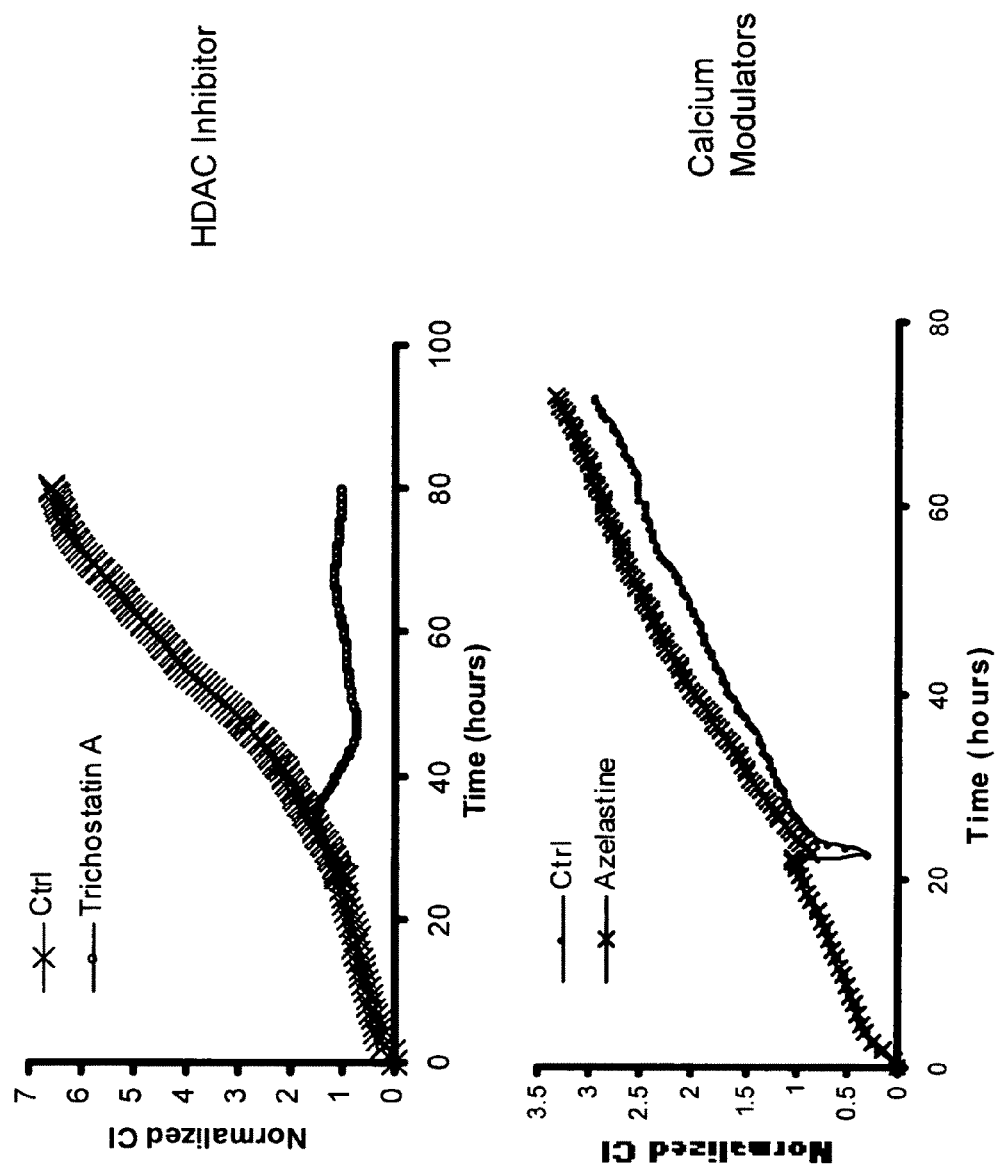

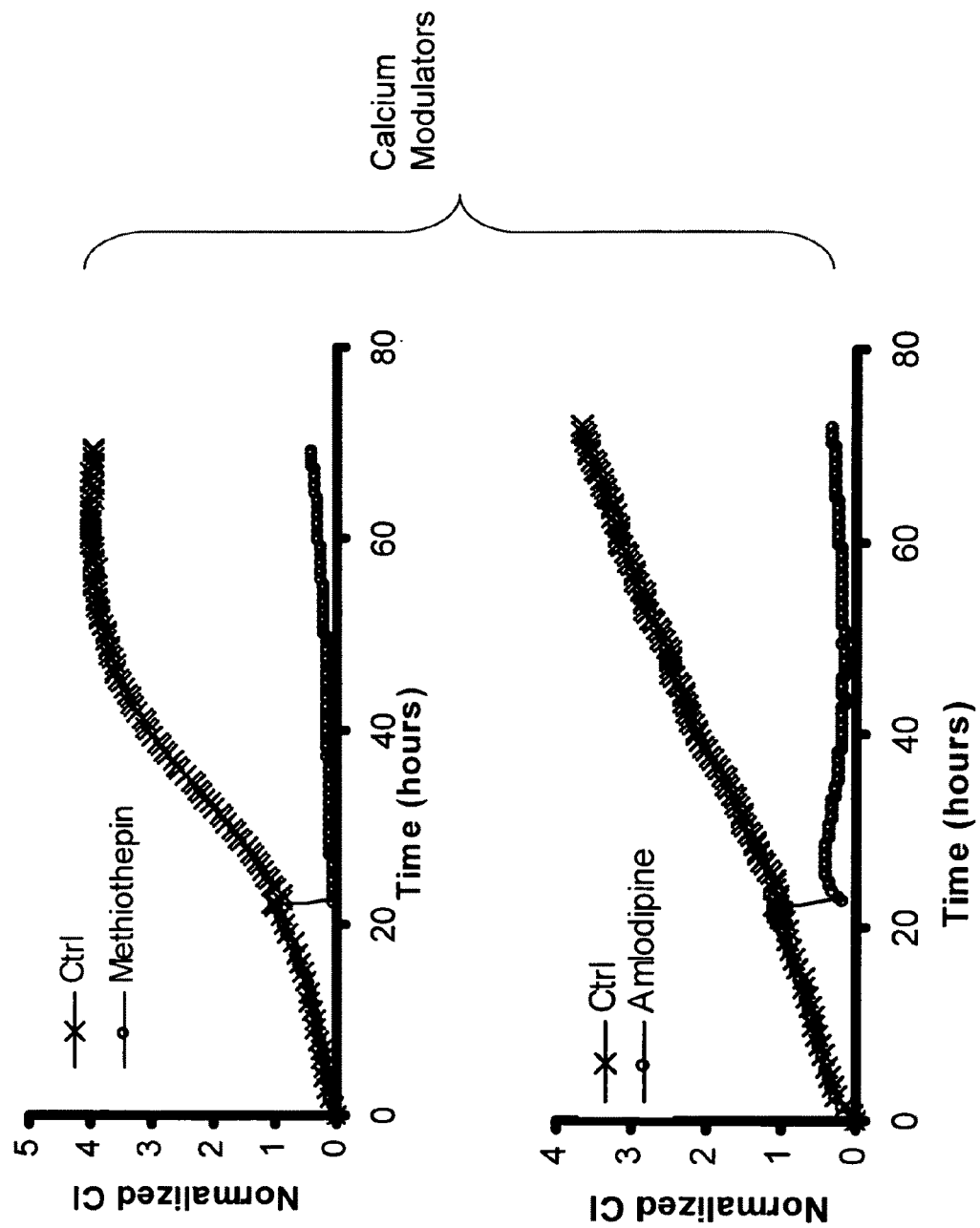
FIG. 5D: Panel 4

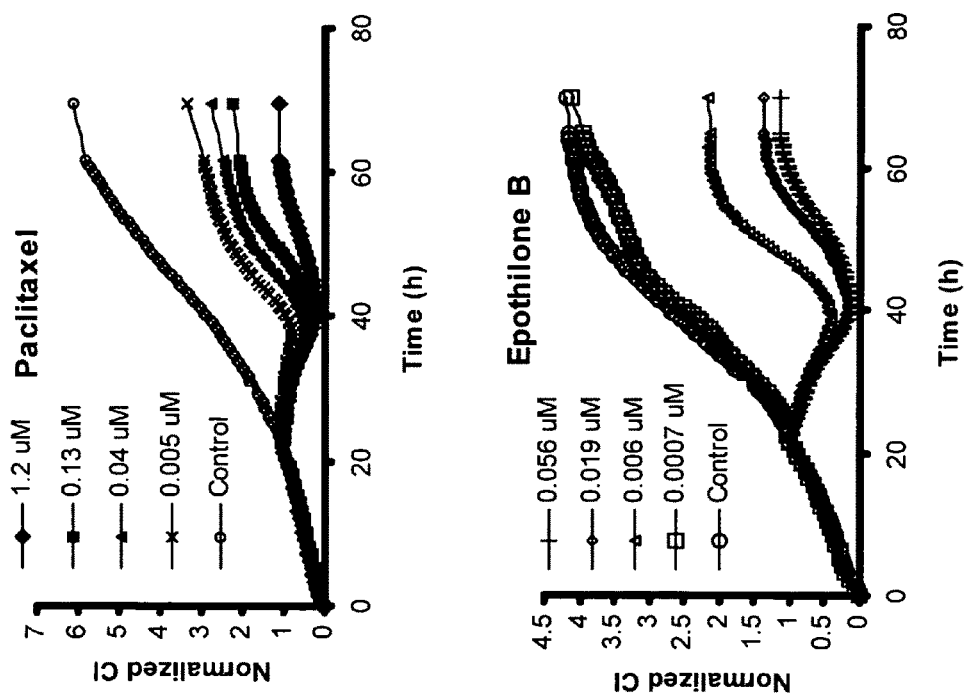

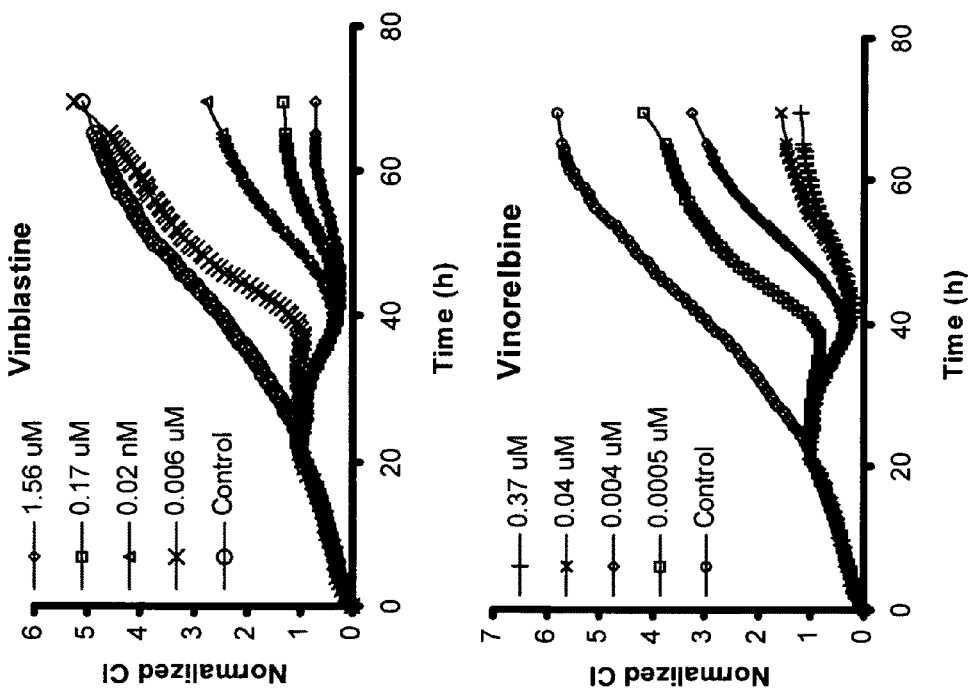
FIG. 6A-2: Panel 2

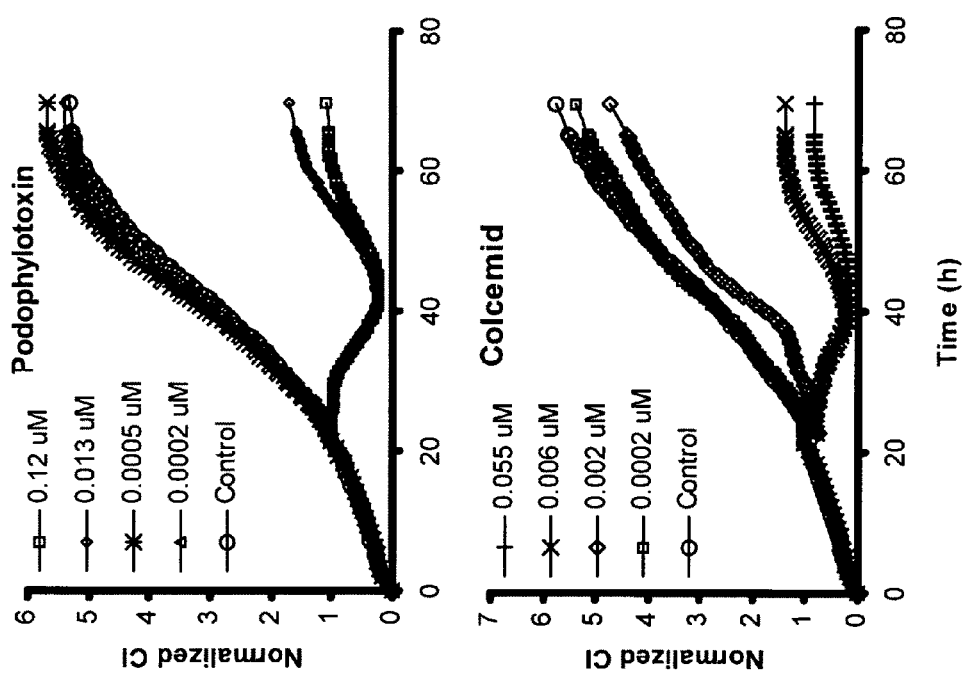
FIG. 6A-3: Panel 3

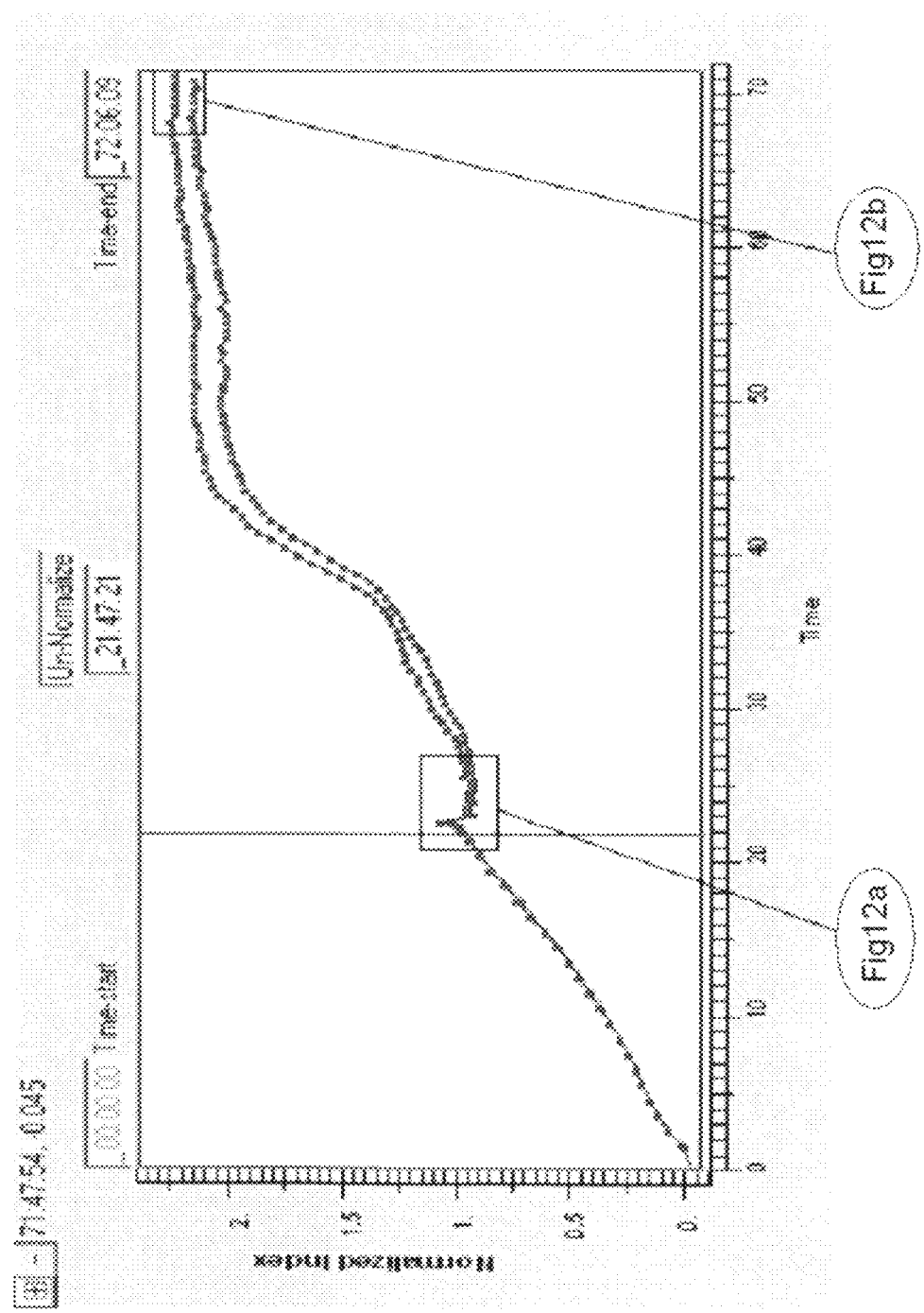
FIG. 12A: Panel 1

FIG. 12B: Panel 2

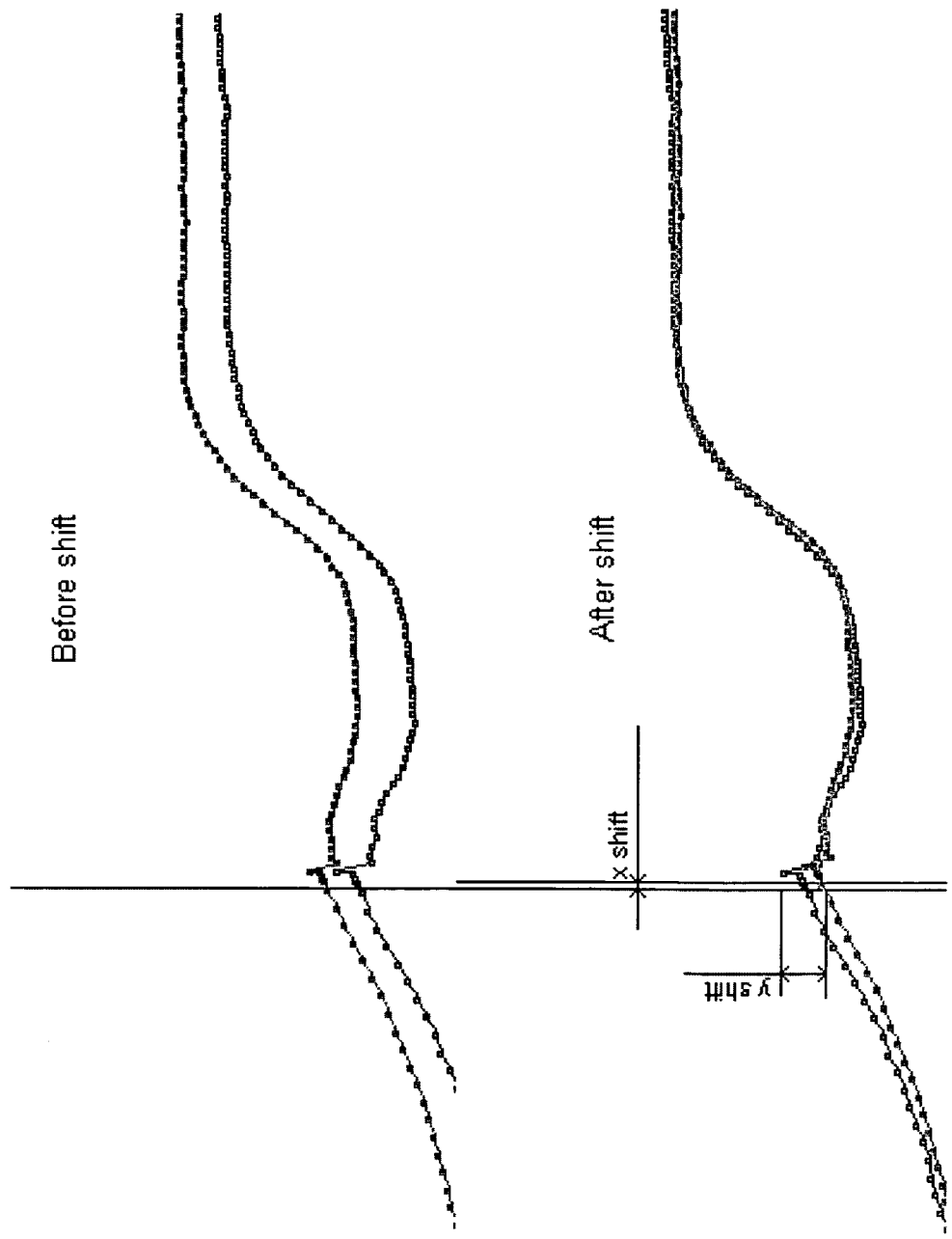

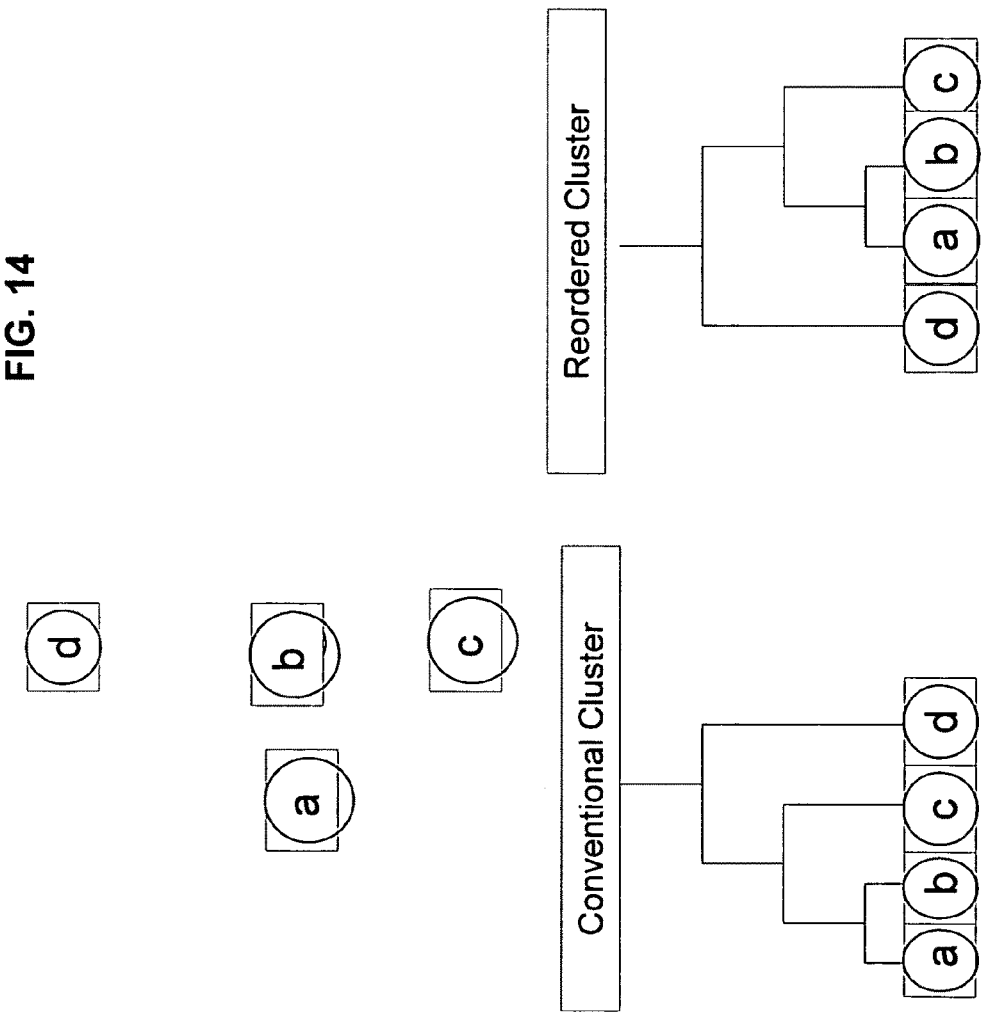

FIG. 17A: Panel 1

Suppose there are 10 curves: A, B, C, D, E, F, G, H, I, and J.
Distance among the wells are

|   | A | B | C | D | E | F | G | H | I | J |
|---|---|---|---|---|---|---|---|---|---|---|
| A |   |   |   |   |   |   |   |   |   |   |
| B | 7 |   |   |   |   |   |   |   |   |   |
| C | 8 | 10 |   |   |   |   |   |   |   |   |
| D | 3 | 17 | 11 |   |   |   |   |   |   |   |
| E | 15 | 4 | 33 | 14 |   |   |   |   |   |   |
| F | 25 | 1 | 14 | 6 | 38 |   |   |   |   |   |
| G | 19 | 24 | 23 | 38 | 32 | 16 |   |   |   |   |
| H | 27 | 34 | 37 | 2 | 39 | 36 | 44 |   |   |   |
| I | 12 | 5 | 20 | 40 | 21 | 41 | 28 | 42 |   |   |
| J | 26 | 35 | 18 | 19 | 22 | 43 | 45 | 9 | 29 | 30 | 31 |

(Use minimum distance rule)
1. BF clustered to group 1
2. DH clustered to group 2
3. A added to DH, and AD < AH
4. E added to BF, and EB < EF
5. I added to EBF, and IE < IF
6. IEBF and ADH form new group (IEBF reversed)
7. C added to FBEIADH, and CF < CH
8. G added to CFBEIADH
9. J added to GCFBEIADH

FIG. 17B: Panel 2

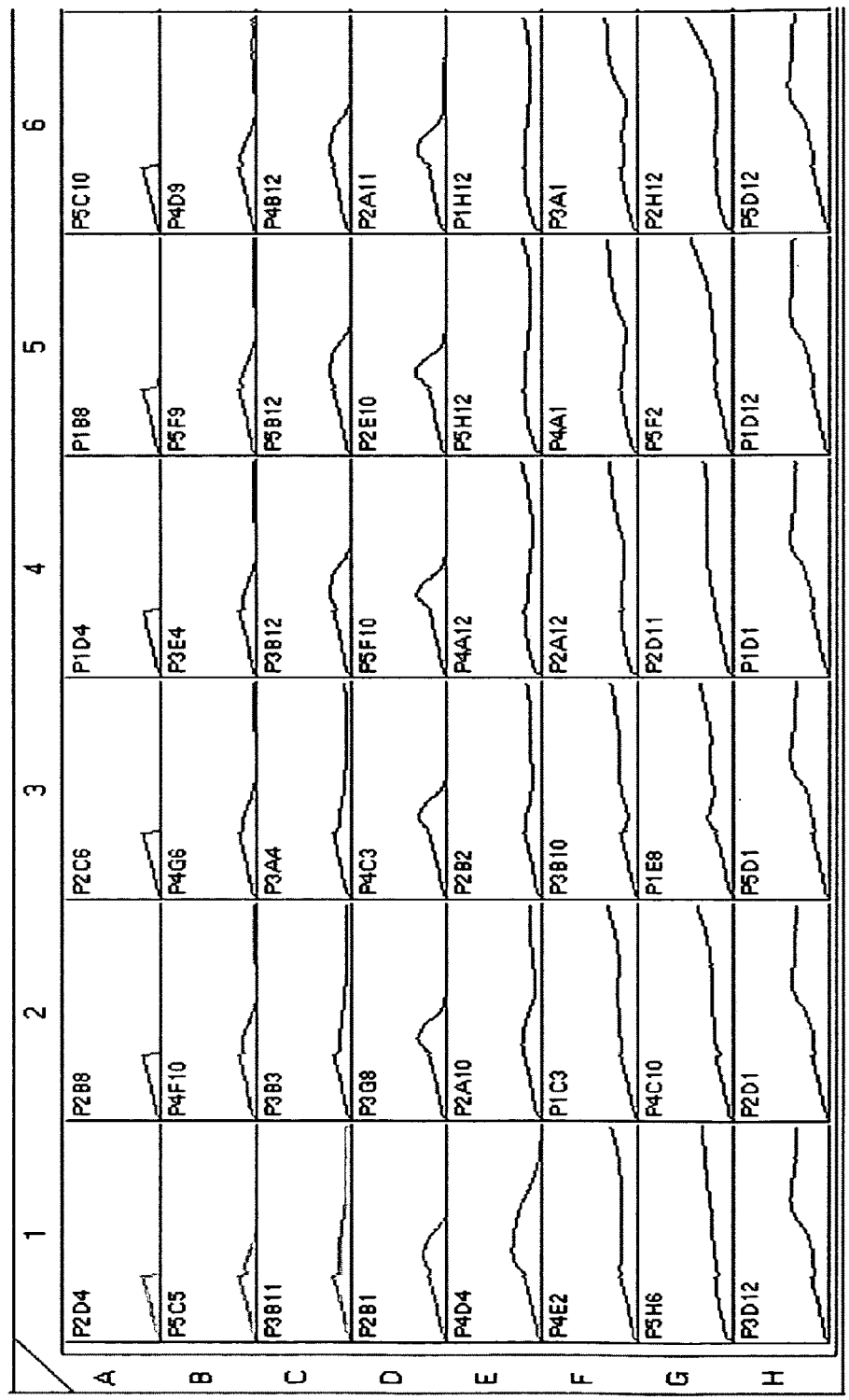
FIG. 19A: Panel 1

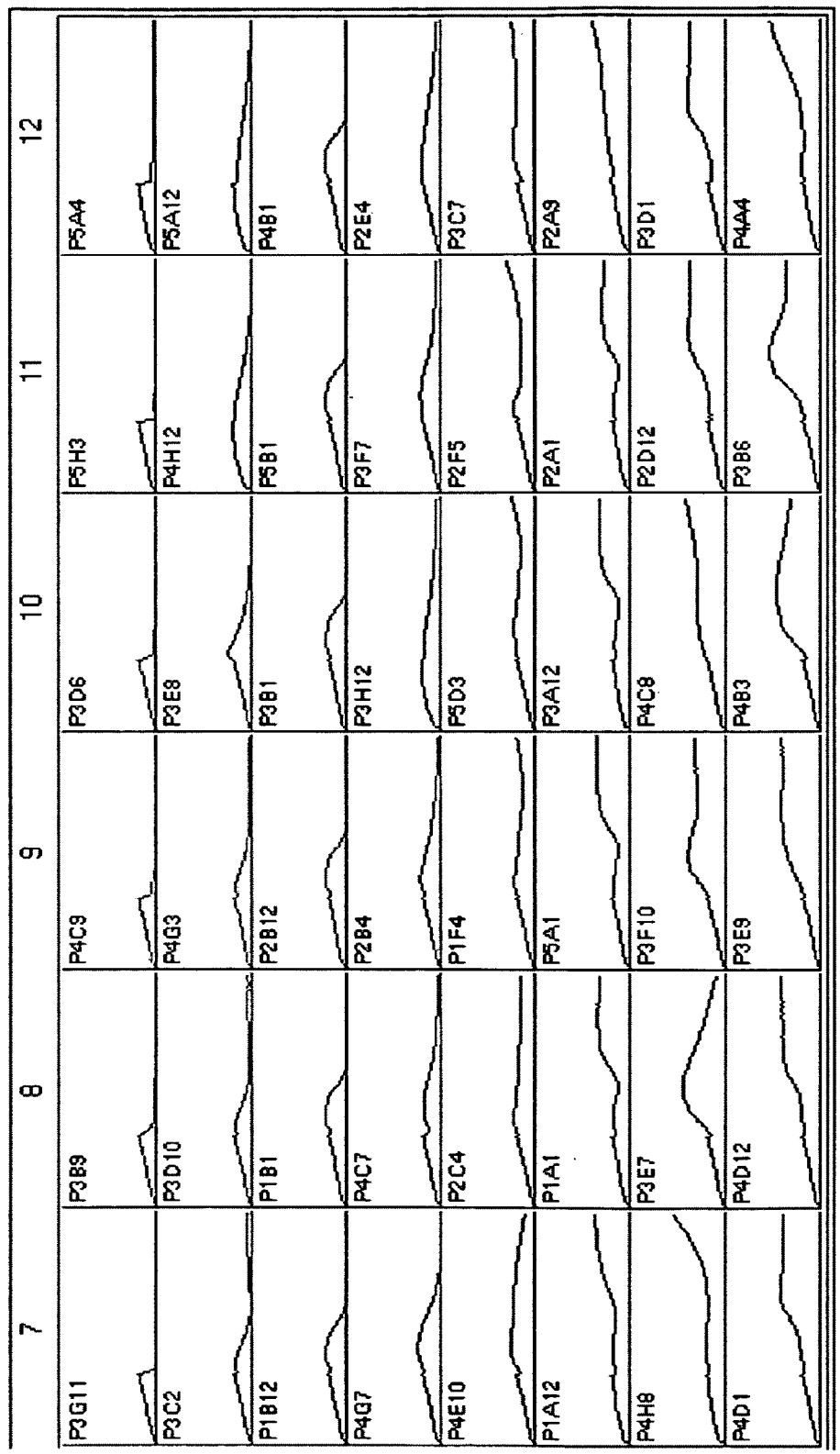
FIG. 19B: Panel 2

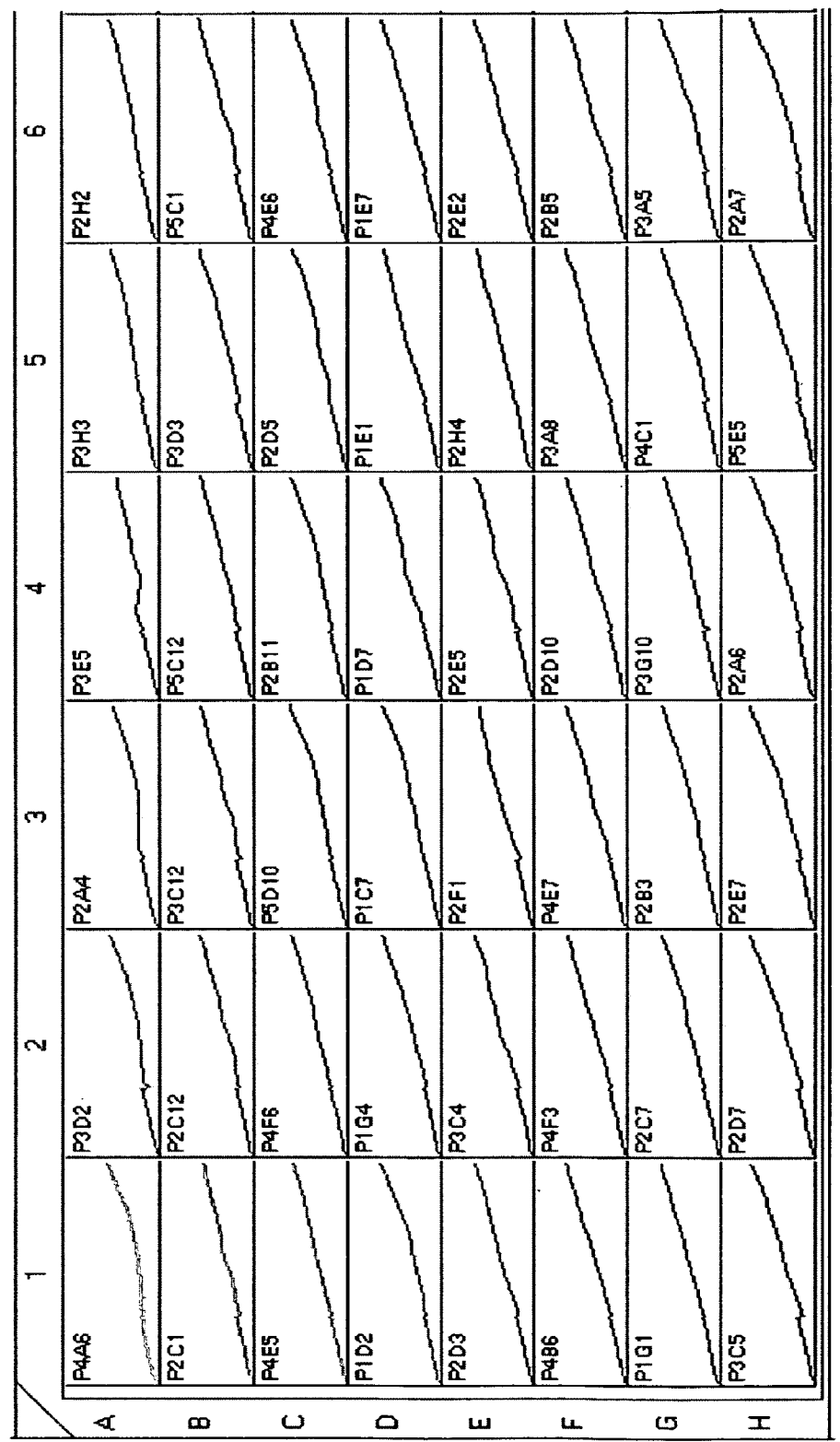
FIG. 19C: Panel 3

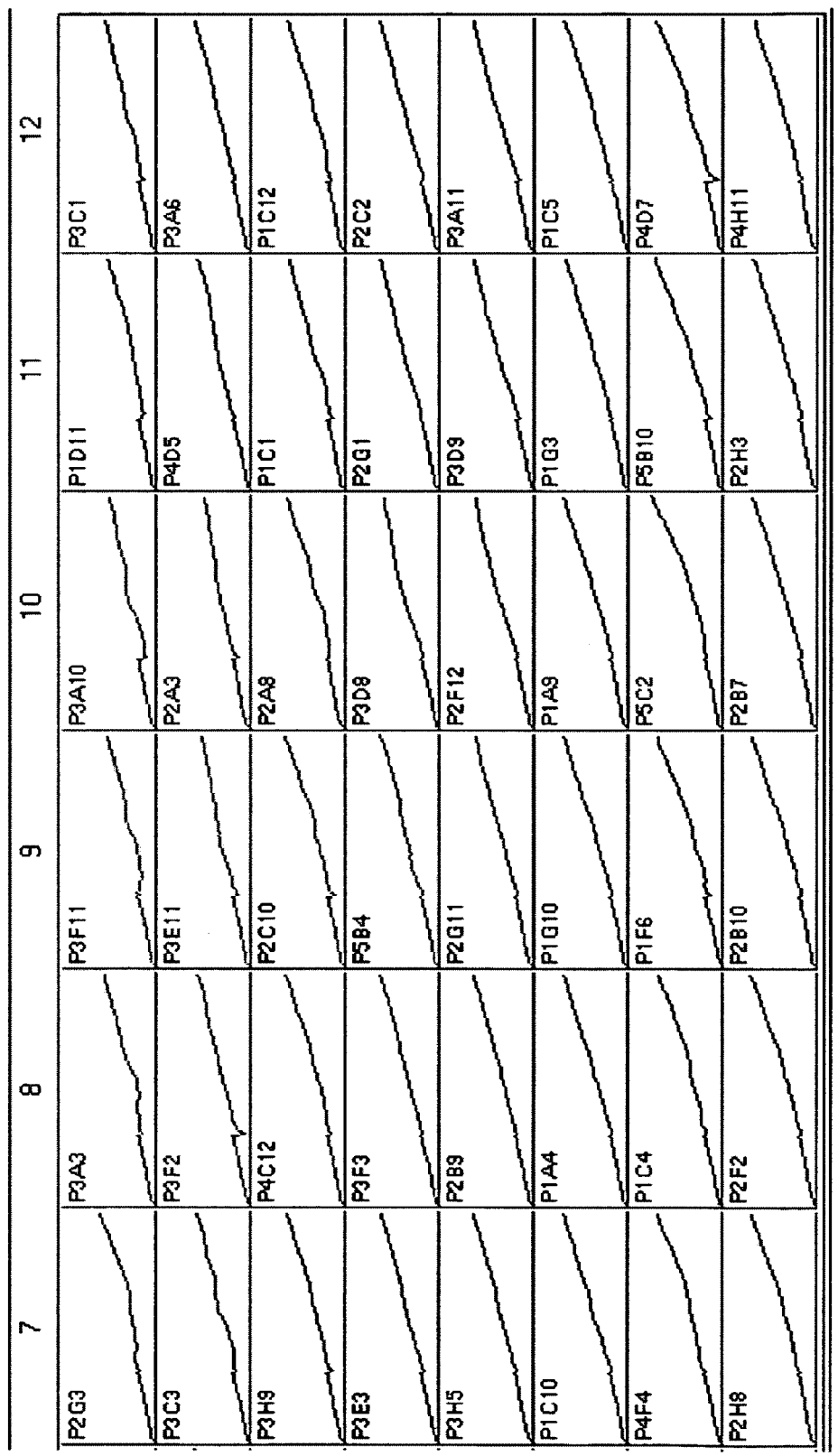
FIG. 19D: Panel 4

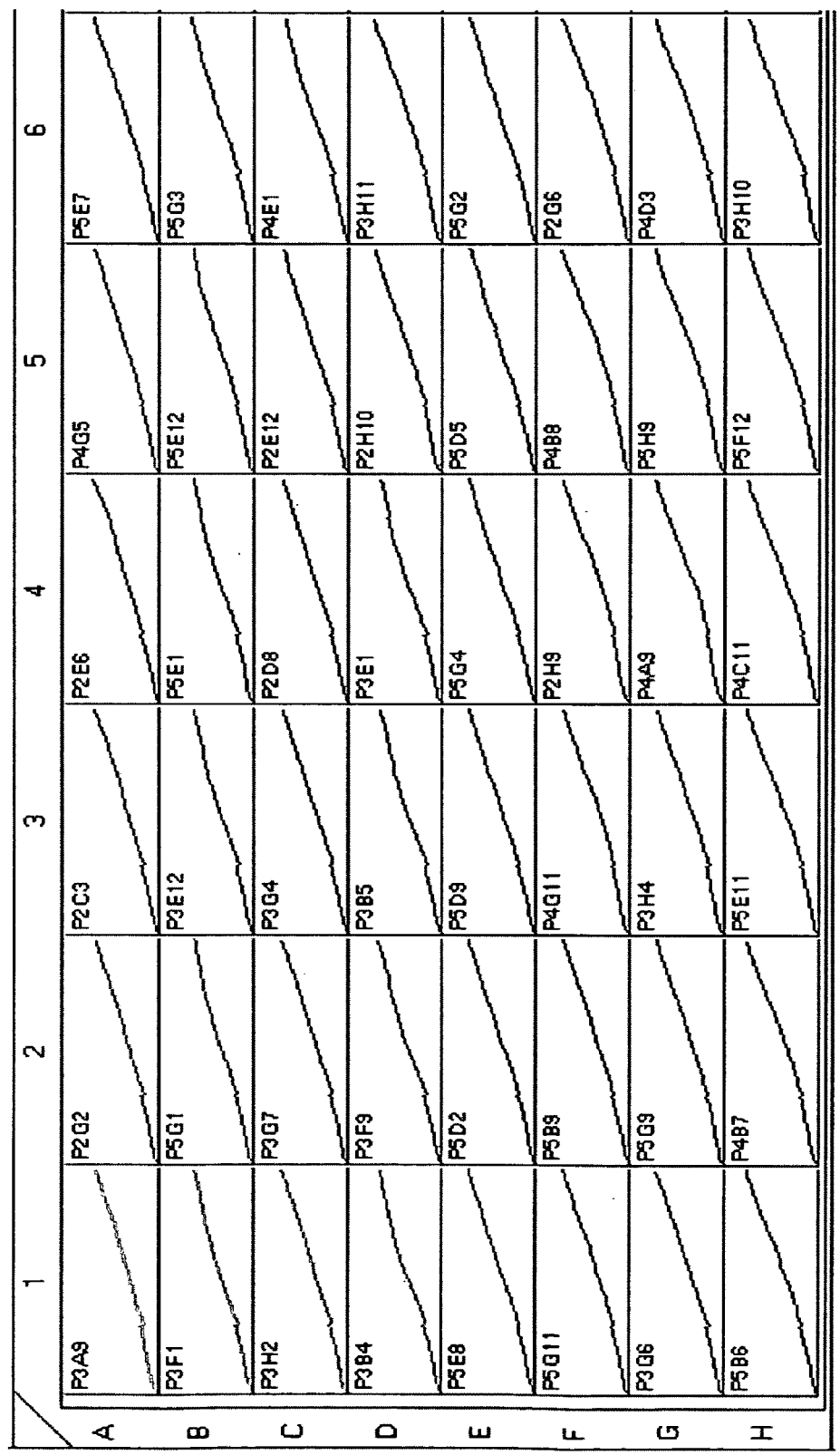
FIG. 19E: Panel 5

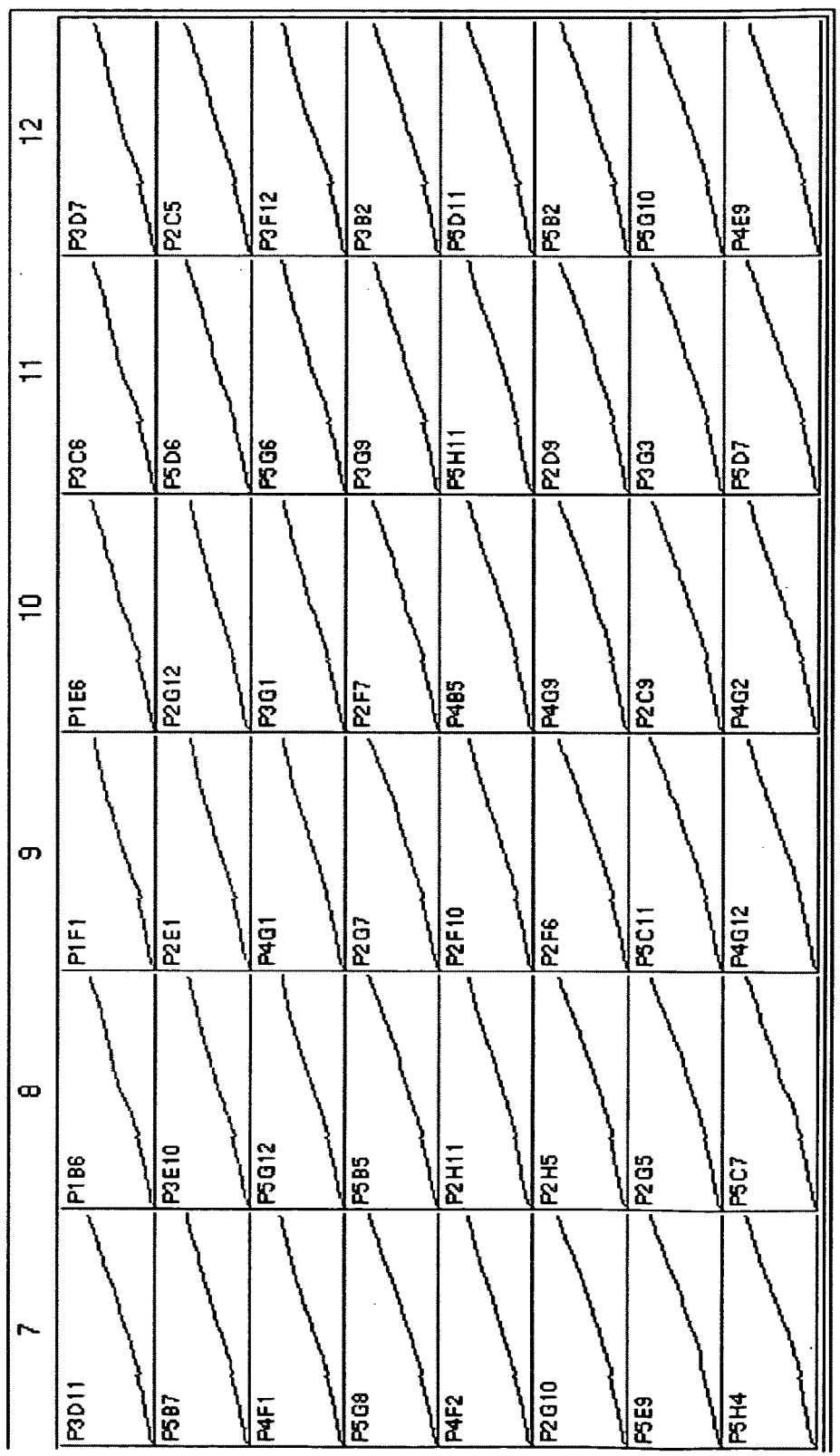
FIG. 19F: Panel 6

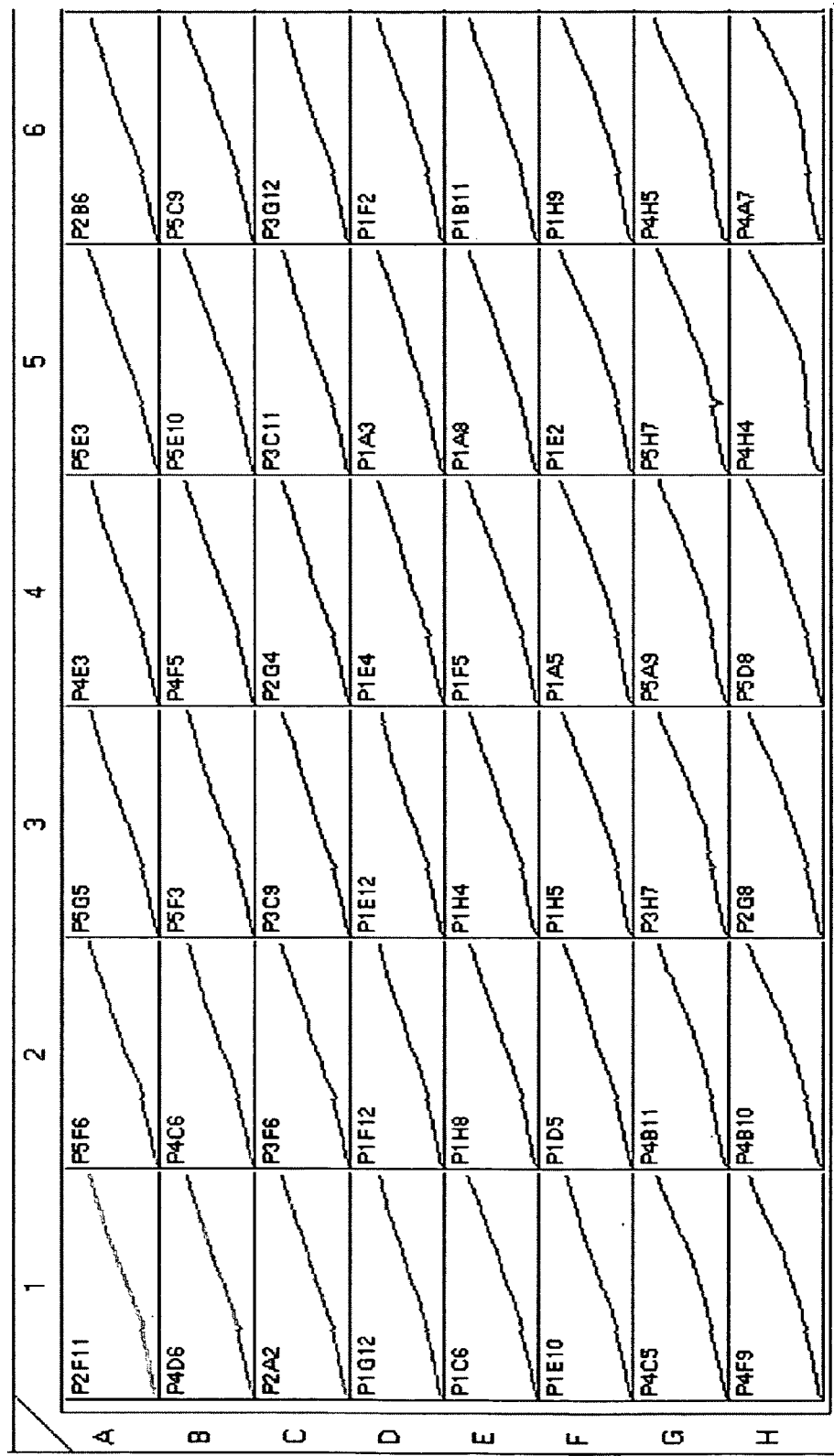
FIG. 19G: Panel 7

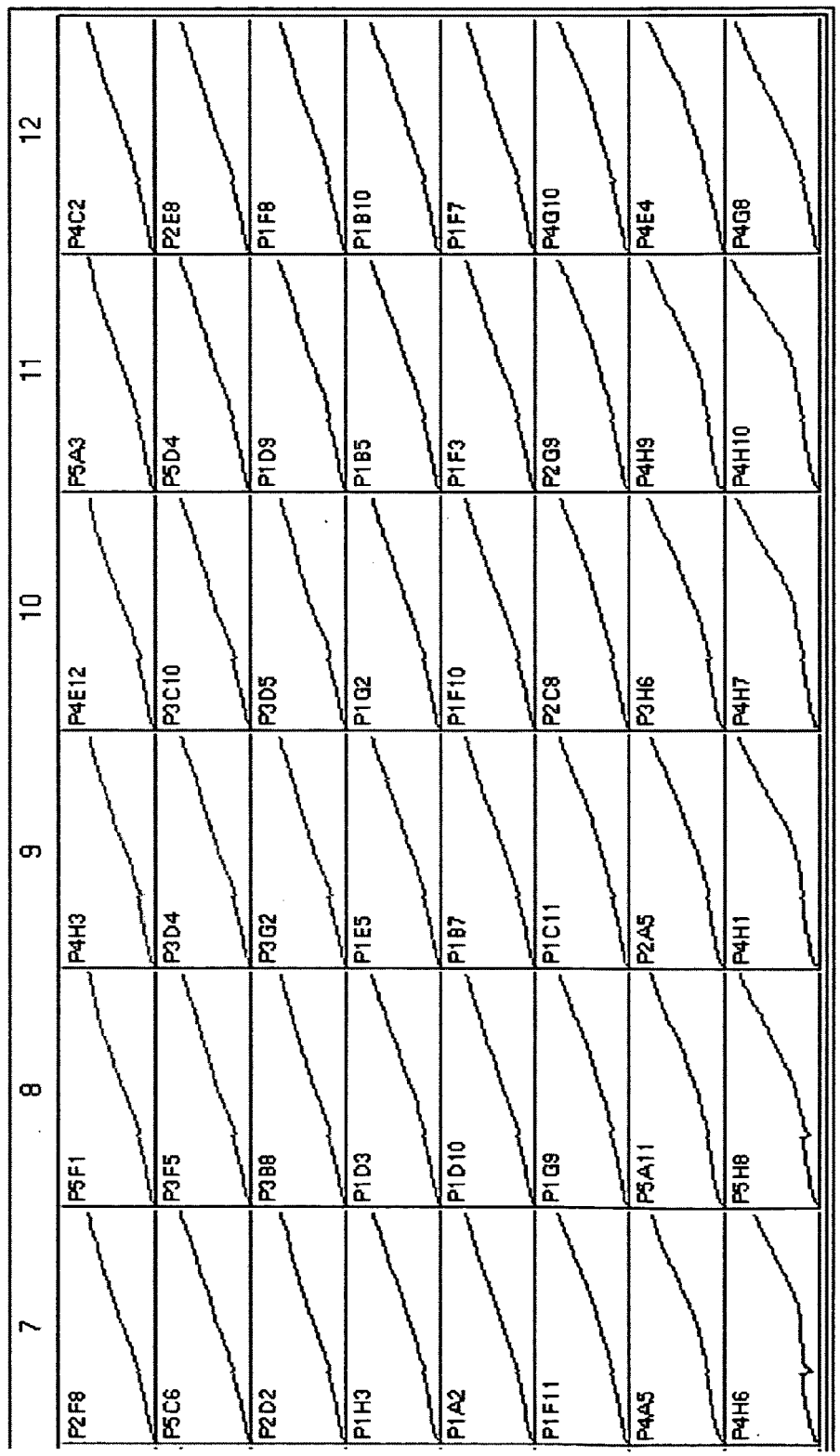
FIG. 19H: Panel 8

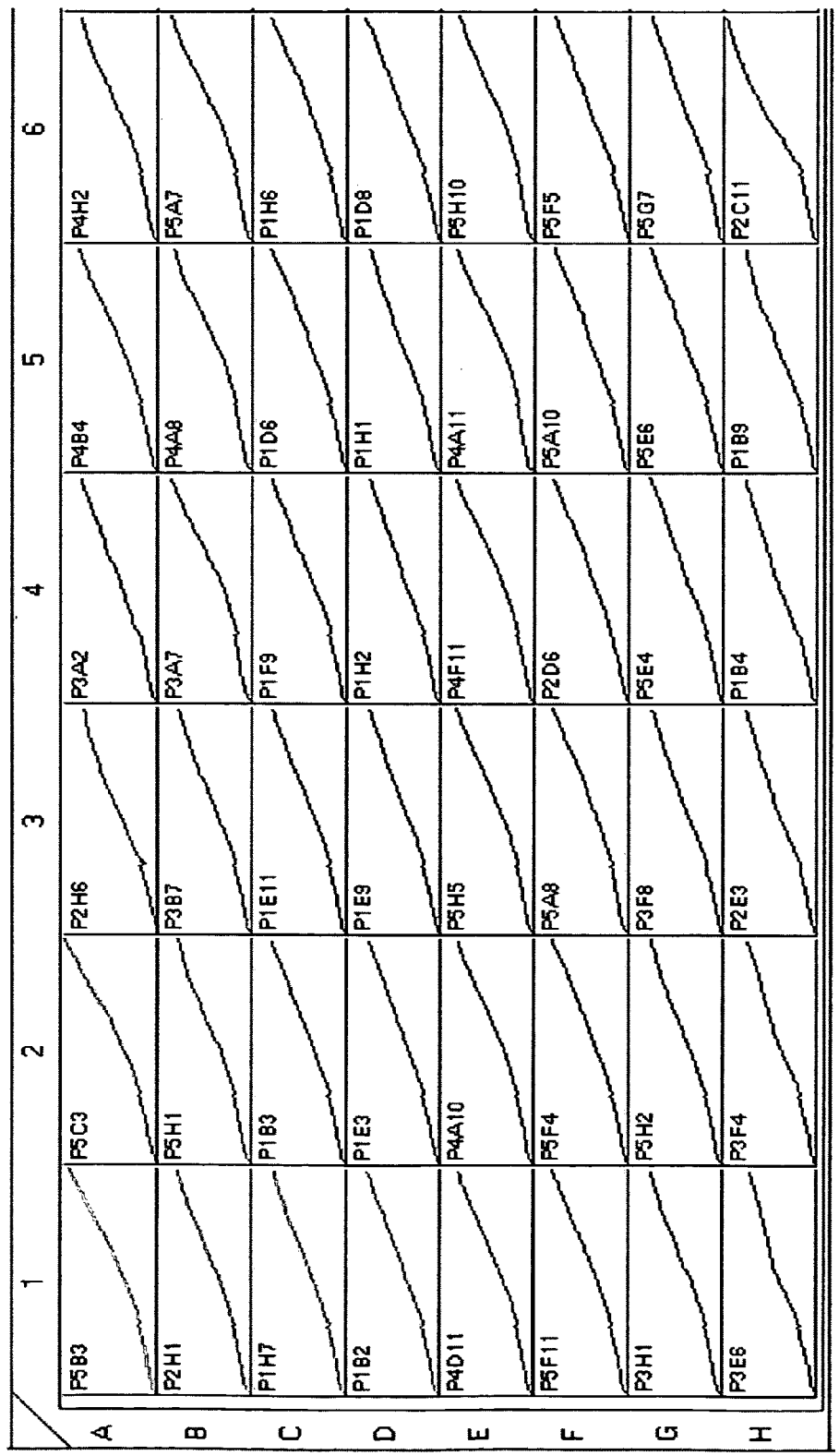
FIG. 19I: Panel 9

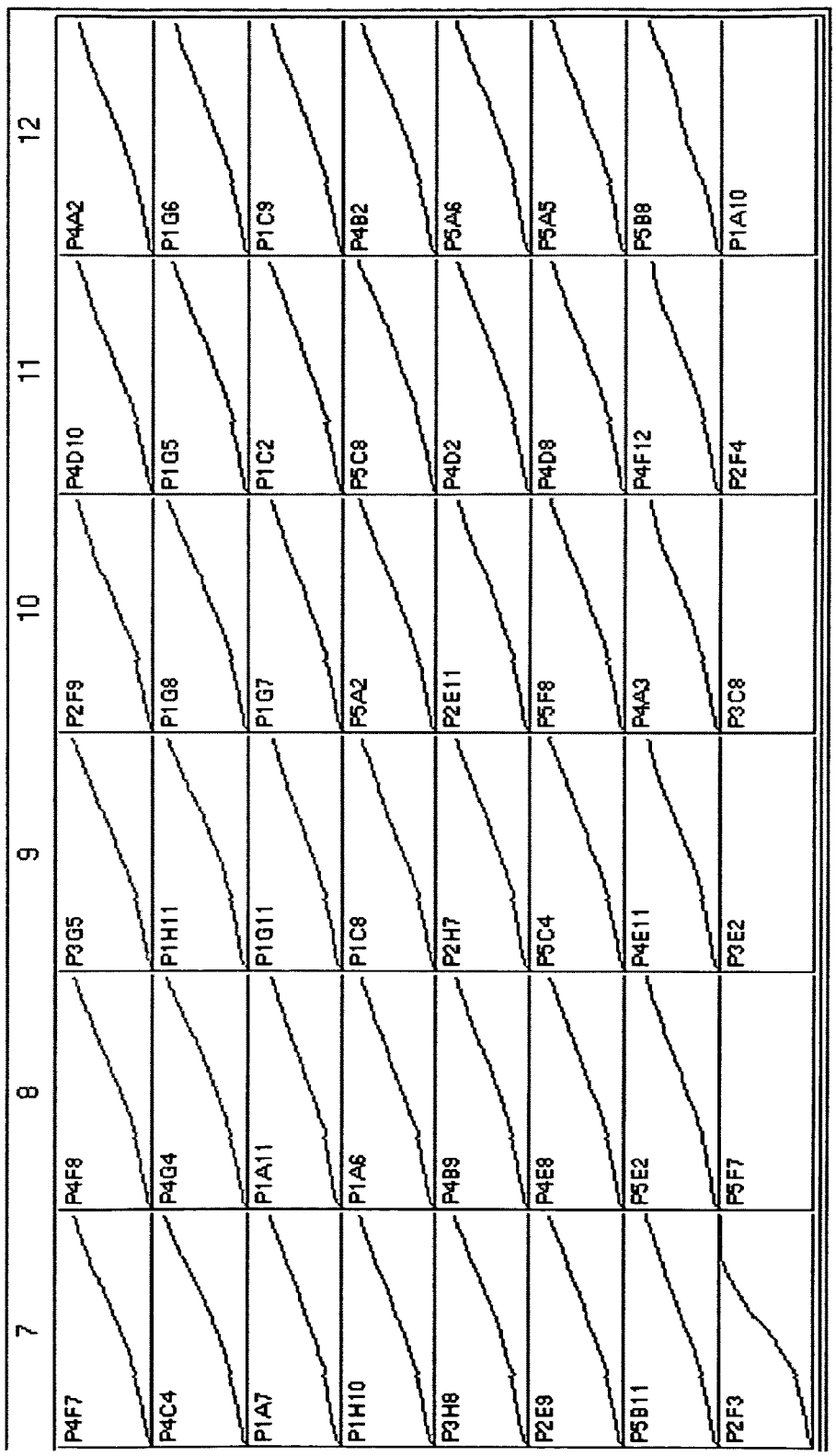
FIG. 19J: Panel 10

USE OF IMPEDANCE-BASED CYTOLOGICAL PROFILING TO CLASSIFY CELLULAR RESPONSE PROFILES UPON EXPOSURE TO BIOLOGICALLY ACTIVE AGENTS

CROSS REFERENCE TO RELATED APPLICATIONS

This application claims benefit of priority to U.S. patent application Ser. No. 60/846,067, filed on Sep. 20, 2006, and is herein incorporated by reference in its entirety.

TECHNICAL FIELD OF THE INVENTION

The present invention relates generally to methods of determining effects on biological systems upon exposure to biologically active molecules and more specifically to the categorization of mechanism specific cellular response profile groups and their association with biologically active agents.

BACKGROUND OF THE INVENTION

The advent of combinatorial chemistry and high throughput screening techniques has revolutionized the drug discovery process allowing for screening and generation of small molecule lead compounds against molecular targets at an unprecedented rate. Most screening assays for small molecule compounds are target driven and it is often difficult to control for off-target interactions. However, the potential interaction of drugs with unintended targets or pathways could prove fatal leading to toxicity or side effects. Additionally, in phenotype-based screening where the target is not readily apparent, identification of the target can prove elusive. Therefore, there is an increasing need in drug discovery, and chemical biology for technologies that can predict or provide information allowing for testable hypotheses regarding the underlying mechanism of action of small molecule compounds.

A number of multi-dimensional profiling technologies including gene expression profiling, proteomic profiling, protein-fragment complementation profiling, high content microscopy-based profiling and cell line cytotoxicity based profiling approaches have been described to measure both the interaction of compounds on intended targets and also generate testable hypotheses concerning mechanism of action and off-target effects. In all cases a very large information-rich data set is generated which can be used to cluster compounds based on activity patterns. Each data point in such a data set corresponds to the measured value for one particular assay target, with all the data in the set being measured at the same time point. These information-rich data sets can be mined with the help of specially designed algorithms to look for specific patterns of activity amongst the compounds being screened and to formulate hypothesis concerning the mechanism of action of compounds. Indeed, all the profiling approaches have had various degrees of success not only in elucidating mechanism of action of unknown compounds, but also unraveling new and novel mechanisms for existing drugs. The challenge in implementing multi-dimensional profiling technologies in a drug discovery setting is to formulate a method that is practical, simple to use and easy to analyze and can be used on routine basis.

SUMMARY OF THE INVENTION

The present invention provides methods of multi-dimensional profiling of biologically active agents and determining their effects on biological systems. The methods of the present invention include real-time impedance monitoring of cellular responses to biologically active agents and categorization of cellular kinetic profiles into mechanism specific cellular response profile groups. The grouping of similar cellular response profiles allows the correlation between agent and mechanism, thus allowing for the identification of potential therapeutic applications of agents or further study of cellular responses or mechanisms.

The impedance-based system of the present invention provides numerous benefits over the currently used techniques. First, the signature activity profiles are derived from a single well without any extensive manipulations such as washing, fixation, lysing and staining. Second, impedance measurements are based on the inherent cellular response to compounds such as modulation of cell viability, morphology and or adhesion, and therefore precludes the need for engineering the cell with reporter proteins such as GFP or luciferase. Thirdly, impedance-based technology can monitor both short and long term responses and therefore can better predict off target effects or mechanisms that may be kinetically distinct and isolated. This is a key difference between impedance-based technology and previous multi-dimensional profiling technologies. In impedance-based technology, the multi-dimensional nature of the data relates to the impedance measurement being conducted at multiple time points after cells are exposed to biologically active agents. Thus, the impedance-based technology can monitor entire process of cellular response to a treatment by biologically active agents. This is in contrast with conventional multi-dimensional profiling technologies where multi-assay targets are analyzed and monitored at a given time after cells are treated with biologically active agents. Therefore, there is generally no kinetic information about cellular response processes in these conventional multi-dimensional profiling technologies. Indeed, the present invention includes monitoring kinetic cell-electrode impedance response curves to biologically active agents and classifying these response curves to different groups.

In one aspect of the present invention a method of categorizing a cell response to a known biologically active agent into a mechanism-specific response profile group is disclosed. The method includes providing a device for measuring cell-substrate impedance operably connected to an impedance analyzer, wherein the device includes at least two wells; adding cells to the at least two wells; monitoring impedance of the at least two wells at time intervals over a period of time and optionally determining cell indices from impedance values; introducing at least one known biologically active agent to at least one and a control to another of the at least two wells, the introduction occurring during the time period such that at least one of the impedance values is obtained prior to the introduction; generating an impedance-based curve or optionally a cell index curve for each of the at least one known biologically active agent and the control; comparing the impedance-based curves or optionally the cell index curves between the at least one known biologically active agent well and the control well; and if significantly different, categorizing the impedance-based curve or optionally the cell index curve of the at least one known biologically active agent to a group. The group defines a mechanism-specific cellular response profile corresponding to the at least one known biologically active agent.

In another aspect of the present invention, a method of categorizing a cell response to an unknown biologically active agent is disclosed. The method including providing a device for measuring cell-substrate impedance operably connected to an impedance analyzer, the device including at least two wells; adding cells to the at least two wells; monitoring impedance of the at least two wells over a time period and optionally determining cell indices from impedance values; introducing at least one unknown biologically active agent to at least one and a control to another of the at least two wells, the introduction occurring during the time period such that at least one of the impedance values is obtained prior to the introduction; generating an impedance-based curve and/or optionally a cell index curve for the unknown biologically active agent and the control; comparing the impedance-based curves or optionally said cell index curves between the unknown biologically active agent and the control; and if significantly different, comparing the impedance-based curve or optionally the cell index curve of the unknown biologically active agent to at least one predetermined mechanism-specific cellular response profile group. The impedance-based curve or cell index curve is categorized into the group if sufficiently similar and into a different group if not sufficiently similar.

In another aspect of the present invention, a method of categorizing responses to biologically active agents into groups is disclosed. The methods include providing a device for measuring cell-substrate impedance operably connected to an impedance analyzer, the device including at least three wells; adding cells to the at least three wells; monitoring impedance of the at least three wells over a time period and optionally determining cell indices from impedance values; introducing at least two biologically active agents, each to a different well of the at least three wells and introducing a control to another different well, the introduction occurring during the time period such that at least one of the impedance values is obtained prior to the introduction; generating an impedance-based curve and/or optionally a cell index curve for each known biologically active agent and the control; comparing the impedance-based curves or optionally the cell index curves to one another and categorizing the impedance-based curves or optionally cell index curves into one or more groups according to the presence or absence of at least one sufficient similarity.

BRIEF DESCRIPTION OF THE DRAWINGS

FIGS. 3A and 3B depict a series of graphs depicting kinetic signature profiles, represented as cell index over time, of different cell lines (H460, NIH3T3, HT1080, HepG2) seeded at two different densities. The kinetic signature profiles are characteristic of each specific cell line and can be used for quality control assessment of cell behavior.

FIG. 4 is a graphical representation of the effect of curve normalization or normalizing cell index curves. FIG. 4A is a non-normalized curve, whereas

FIGS. 5A through 5D provide a graphical representation cell response profiles, shown as normalized cell index values over time, of A549 cells treated (at time ~20 hr) with compounds having different mechanisms of action. The cell response profile is a manifestation of the mechanism of action of each compound.

FIGS. 6A-1 through 6A-3 provide a graphical representation of cell response profiles, shown as normalized cell index values over time, of A549 cells treated (at time ~20 hr) with different anti-mitotic agents. The response profiles of the cells are similar for compounds with similar mechanism.

FIG. 13 is a graphical representation of two curves before and after shifting for more accurate alignment of curves.

FIG. 14 is a cartoon demonstrating multiple objects or curves may be categorized or clustered such that the most similar objects or curves are grouped nearest to one another.

FIGS. 17A and 17B provide charts depicting the classification, grouping and reordering of clusters such that the most similar objects or curves are positioned nearest to one another. For simplicity, in this example, each curve is represented by a letter A, B, C, D, E, F, G, H, I and J. The distance between each curve pair is given and as shown.

FIGS. 19A through 19J depict results of curve classification and categorizing of 480-curves from a five 96-well microplate experiment. In this case, there are initially five 96-well micro-plates. The arrangement of 480-curves in the five 96-curve graphs is based on classification and reordering results of these curves so that the classified curves, when arranged along an one-dimension, have the feature that curves with smaller distances are located near to each other.

DETAILED DESCRIPTION OF THE INVENTION

Figure 1A:
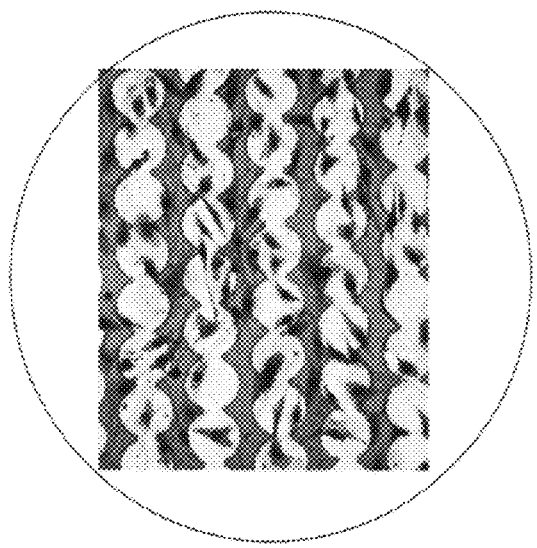
FIG. 1A is photograph depicting mammalian cells interacting with gold microelectrodes, which are laid down in the bottom of the wells of microtiter plates (also referred to as "E-Plates").

The present patent application incorporates by reference herein the following U.S. patent applications in their entirety: 60/397,749 filed on Jul. 20, 2002; 60/435,400 filed on Dec. 20, 2002; 60/469,572 filed on May 9, 2003; Ser. No. 10/705,447 filed on Nov. 10, 2003; Ser. No. 10/705,615 filed on Nov. 10, 2003; 60/519,567 filed on Nov. 12, 2003; Ser. No. 10/987,732 filed on Nov. 12, 2004; Ser. No. 11/725,040 filed on Mar. 15, 2007; 60/542,927 filed on Feb. 9, 2004; Ser. No. 11/055,639 filed on Feb. 9, 2005; 60/548,713 filed on Feb. 27, 2004; 60/598,609 filed on Aug. 4, 2004; Ser. No. 11/198,831 filed on Aug. 4, 2005; 60/598,608 filed on Aug. 4, 2004; Ser. No. 11/197,994 filed on Aug. 4, 2005; 60/613,872 filed on Sep. 27, 2004; 60/613,749 filed on Sep. 27, 2004; 60/614,601 filed on Sep. 29, 2004; 60/630,131 filed on Nov. 22, 2004; Ser. No. 11/235,938 filed on Sep. 27, 2005; 60/630,071 filed on Nov. 22, 2004; 60/630,809 filed on Nov. 24, 2004; Ser. No. 11/286,882 filed on Nov. 23, 2005; 60/633,019 filed on Dec. 3, 2004; 60/647,159 filed on Jan. 26, 2005; 60/647,189 filed on Jan. 26, 2005; 60/647,075 filed on Jan. 26, 2005; 60/653,904 filed on Feb. 17, 2005; 60/660,829 filed on Mar. 10, 2005; 60/660,898 filed on Mar. 10, 2005; 60/673,678 filed on Apr. 21, 2005; 60/689,422 filed on Jun. 10, 2005; 60/819,240 filed on Jul. 7, 2006; 60/831,409 filed on Jul. 17, 2006; and 60/851,737 filed on Oct. 14, 2006.

Definitions

For clarity of disclosure, and not by way of limitation, the detailed description of the invention is divided into the subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "biocompatible substrate" means a substrate that does not have deleterious effects on cells, including the viability, attachment, spreading, motility, growth, or cell division.

A "biomolecular coating" or a "biological molecule coating" is a coating on a surface that comprises a molecule that is a naturally occurring biological molecule or biochemical, or a biochemical derived from or based on one or more naturally occurring biomolecules or biochemicals. For example, a biological molecule coating can include an extracellular matrix component (e.g., fibronectin, collagens), or a derivative thereof, or can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occurring biochemicals.

An "organic compound coating" is a coating on a surface that includes an organic compound. For example an organic compound may include a natural ligand or an agonist or an antagonist for a cell surface receptor.

An "extracellular matrix component" is a molecule that occurs in the extracellular matrix of an animal. It can be a component of an extracellular matrix from any species and from any tissue type. Nonlimiting examples of extracellular matrix components include laminins, collagens fibronectins, other glycoproteins, peptides, glycosaminoglycans, proteoglycans, etc. Extracellular matrix components can also include growth factors.

An "electrode" is a structure having a high electrical conductivity, that is, an electrical conductivity much higher than the electrical conductivity of the surrounding materials.

As used herein, an "electrode structure" refers to a single electrode, particularly one with a complex structure (as, for example, a spiral electrode structure), or a collection of at least two electrode elements that are electrically connected together. All the electrode elements within an "electrode structure" are electrically connected.

As used herein, "electrode element" refers to a single structural feature of an electrode structure, such as, for example, a fingerlike projection of an interdigitated electrode structure.

As used herein, an "electrode array" or "electrode structure unit" is two or more electrode structures that are constructed to have dimensions and spacing such that they can, when connected to a signal source, operate as a unit to generate an electrical field in the region of spaces around the electrode structures. Preferred electrode structure units of the present invention can measure impedance changes due to cell attachment to an electrode surface. Non-limiting examples of electrode structure units are interdigitated electrode structure units and concentric electrode structure units.

An "electrode bus" is a portion of an electrode that connects individual electrode elements or substructures. An electrode bus provides a common conduction path from individual electrode elements or individual electrode substructures to another electrical connection. In the devices of the present invention, an electrode bus can contact each electrode element of an electrode structure and provide an electrical connection path to electrical traces that lead to a connection pad.

"Electrode traces" or "electrically conductive traces" or "electrical traces", are electrically conductive paths that extend from electrodes or electrode elements or electrode structures toward one end or boundary of a device or apparatus for connecting the electrodes or electrode elements or electrode structures to an impedance analyzer. The end or boundary of a device may correspond to the connection pads on the device or apparatus.

A "connection pad" is an area on an apparatus or a device of the present invention which is electrically connected to at least one electrode or all electrode elements within at least one electrode structure on an apparatus or a device and which can be operatively connected to external electrical circuits (e.g., an impedance measurement circuit or a signal source). The electrical connection between a connection pad and an impedance measurement circuit or a signal source can be direct or indirect, through any appropriate electrical conduction means such as leads or wires. Such electrical conduction means may also go through electrode or electrical conduction paths located on other regions of the apparatus or device.

"Interdigitated" means having projections coming one direction that interlace with projections coming from a different direction in the manner of the fingers of folded hands (with the caveat that interdigitated electrode elements preferably do not contact one another).

As used herein, a "high probability of contacting an electrode element" means that, if a cell is randomly positioned within the sensor area of a device or apparatus of the present invention, the probability of a cell (or particle) contacting on an electrode element, calculated from the average diameter of a cell used on or in a device or apparatus of the present invention, the sizes of the electrode elements, and the size of the gaps between electrode elements, is greater than about 50%, more preferably greater than about 60%, yet more preferably greater than about 70%, and even more preferably greater than about 80%, greater than about 90%, or greater than about 95%.

As used herein, "at least two electrodes fabricated on said substrate" means that the at least two electrodes are fabricated or made or produced on the substrate. The at least two electrodes can be on the same side of the substrate or on the different side of the substrate. The substrate may have multiple layers, the at least two electrodes can be either on the same or on the different layers of the substrate.

As used herein, "at least two electrodes fabricated to a same side of said substrate" means that the at least two electrodes are fabricated on the same side of the substrate.

As used herein, "at least two electrodes fabricated to a same plane of said substrate" means that, if the nonconducting substrate has multiple layers, the at least two electrodes are fabricated to the same layer of the substrate.

As used herein, "said . . . electrodes (or electrode structures) have substantially the same surface area" means that the surface areas of the electrodes referred to are not substantially different from each other, so that the impedance change due to cell attachment or growth on any one of the electrodes (or electrode structures) referred to will contribute to the overall detectable change in impedance to a same or similar degree as the impedance change due to cell attachment or growth on any other of the electrodes (or electrode structures) referred to. In other words, where electrodes (or electrode structures) have substantially the same surface area, any one of the electrodes can contribute to overall change in impedance upon cell attachment or growth on the electrode. In most cases, the ratio of surface area between the largest electrode and the smallest electrode that have "substantially the same surface area" is less than 10. Preferably, the ratio of surface area between the largest electrode and the smallest electrode of an electrode array is less than 5, 4, 3, 2, 1.5, 1.2 or 1.1. More preferably, the at least two electrodes of an electrode structure have nearly identical or identical surface area.

As used herein, "said device has a surface suitable for cell attachment or growth" means that the electrode and/or non-electrode area of the apparatus has appropriate physical, chemical or biological properties such that cells of interest can viably attach on the surface and new cells can continue to attach, while the cell culture grows, on the surface of the apparatus. However, it is not necessary that the device, or the surface thereof, contain substances necessary for cell viability or growth. These necessary substances, e.g., nutrients or growth factors, can be supplied in a medium. Preferably, when a suspension of viable, unimpaired, epithelial or endothelial cells is added to the "surface suitable for cell attachment" when at least 50% of the cells are adhering to the surface within twelve hours. More preferably, a surface that is suitable for cell attachment has surface properties so that at least 70% of the cells are adhering to the surface within twelve hours of plating (i.e., adding cells to the chamber or well that comprises the said device). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating.

As used herein, "detectable change in impedance between or among said electrodes" (or "detectable change in impedance between or among said electrode structures") means that the impedance between or among said electrodes (or electrode structures) would have a significant change that can be detected by an impedance analyzer or impedance measurement circuit when molecule binding reaction occurs on the electrode surfaces. The impedance change refers to the difference in impedance values when molecule binding reaction occurs on the electrode surface of the apparatus and when no molecular reaction occurs on the electrode surface. Alternatively, the impedance change refers to the difference in impedance values when cells are attached to the electrode surface and when cells are not attached to the electrode surface, or when the number, type, activity, adhesiveness, or morphology of cells attached to the electrode-comprising surface of the apparatus changes. In most cases, the change in impedance is larger than 0.1% to be detectable. Preferably, the detectable change in impedance is larger than 1%, 2%, 5%, or 8%. More preferably, the detectable change in impedance is larger than 10%. Impedance between or among electrodes is typically a function of the frequency of the applied electric field for measurement. "Detectable change in impedance between or among said electrodes" does not require the impedance change at all frequencies being detectable. "Detectable change in impedance between or among said electrodes" only requires a detectable change in impedance at any single frequency (or multiple frequencies). In addition, impedance has two components, resistance and reactance (reactance can be divided into two categories, capacitive reactance and inductive reactance). "Detectable change in impedance between or among said electrodes" requires only that either one of resistance and reactance has a detectable change at any single frequency or multiple frequencies. In the present application, impedance is the electrical or electronic impedance. The method for the measurement of such impedance is achieved by, (1) applying a voltage between or among said electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. Measurement of such electric impedance is an electronic or electrical process that does not involve the use of any reagents.

As used herein, "said at least two electrodes have substantially different surface area" means that the surface areas of any electrodes are not similar to each other so that the impedance change due to cell attachment or growth on the larger electrode will not contribute to the overall detectable impedance to a same or similar degree as the impedance change due to cell attachment or growth on the smaller electrodes. Preferably, any impedance change due to cell attachment or growth on the larger electrode is significantly smaller than the impedance change due to cell attachment or growth on the smaller electrode. Ordinarily, the ratio of surface area between the largest electrode and the smallest electrode is more than 10. Preferably, the ratio of surface area between the largest electrode and the smallest electrode is more than 20, 30, 40, 50 or 100.

As used herein, "multiple pairs of electrodes or electrode structures spatially arranged according to wells of a multi-well microplate" means that the multiple pairs of electrodes or electrode structures of a device or apparatus are spatially arranged to match the spatial configuration of wells of a multi-well microplate so that, when desirable, the device can be inserted into, joined with, or attached to a multiwell plate (for example, a bottomless multiwell plate) such that multiple wells of the multi-well microplate will comprise electrodes or electrode structures.

As used herein, "arranged in a row-column configuration" means that, in terms of electric connection, the position of an electrode, an electrode array or a switching circuit is identified by both a row position number and a column position number.

As used herein, "each well contains substantially same number . . . of cells" means that the lowest number of cells in a well is at least 50% of the highest number of cells in a well. Preferably, the lowest number of cells in a well is at least 60%, 70%, 80%, 90%, 95% or 99% of the highest number of cells in a well. More preferably, each well contains an identical number of cells.

As used herein, "each well contains . . . same type of cells" means that, for the intended purpose, each well contains same type of cells; it is not necessary that each well contains exactly identical type of cells. For example, if the intended purpose is that each well contains mammalian cells, it is permissible if each well contains same type of mammalian cells, e.g., human cells, or different mammalian cells, e.g., human cells as well as other non-human mammalian cells such as mice, goat or monkey cells, etc.

As used herein, "each well contains . . . serially different concentration of a biologically active agent" means that each well contains a biologically active agent with a serially diluted concentrations, e.g., an one-tenth serially diluted concentrations of 1 M, 0.1 M, 0.01 M, etc.

As used herein, "dose-response curve" means the dependent relationship of response of cells on the dose concentration of a biologically active agent. The response of cells can be measured by many different parameters. For example, a biologically active agent is suspected to have cytotoxicity and cause cell death. Then the response of cells can be measured by percentage of non-viable (or viable) cells after the cells are treated by the biologically active agent. Plotting this percentage of non-viable (or viable) cells as a function of the dose concentration of the biologically active agent constructs a dose response curve. In the present application, the percentage of non-viable (or viable) cells can be expressed in terms of measured impedance values, or in terms of cell index derived from impedance measurement, or in terms of cell change indexes. For example, for a give cell type and under specific cellular physiological condition (e.g., a particular cell culture medium), cell index can be shown to have a linear correlation or positive correlation with the number of viable cells in a well from which cell index was derived from the impedance measurement. Thus, in the present application, one can plot cell index as a function of the dose concentration of the biologically active agent to construct a "dose-response curve". Note that, generally, cell index not only correlate with the number of viable cells in the wells but also relate to the cell morphology and cell attachment. Thus plotting cell index versus doss concentration provides information not only about number of cells but also about their physiological status (e.g. cell morphology and cell adhesion). Furthermore, an important advantage offered by the system and devices of the present invention is that in a single experiment, one can obtain "dose-response curves" at multiple time points since the system allows for the continuous monitoring of cells and provides impedance measurement at many time points over a time range as short as a few minutes to as long as days or weeks.

As used herein, "the electrodes have, along the length of the microchannel, a length that is substantially less than the largest single-dimension of a particle to be analyzed" means that the electrodes have, along the length of the microchannel, a length that is at least less than 90% of the largest single-dimension of a particle to be analyzed. Preferably, the electrodes have, along the length of the microchannel, a length that is at least less than 80%, 70%, 60%, 50%, 40%, 30%, 20%, 10%, 5% of the largest single-dimension of a particle to be analyzed.

As used herein, "the microelectrodes span the entire height of the microchannel" means that the microelectrodes span at least 70% of the entire height of the microchannel. Preferably, microelectrodes span at least 80%, 90%, 95% of the entire height of the microchannel. More preferably, microelectrodes span at least 100% of the entire height of the microchannel.

As used herein, "microelectrode strip or electrode strip" means that a non-conducting substrate strip on which electrodes or electrode structure units are fabricated or incorporated. The non-limiting examples of the non-conducting substrate strips include polymer membrane, glass, plastic sheets, ceramics, insulator-on-semiconductor, fiber glass (like those for manufacturing printed-circuits-board). Electrode structure units having different geometries can be fabricated or made on the substrate strip by any suitable microfabrication, micromachining, or other methods. Non-limiting examples of electrode geometries include interdigitated electrodes, circle-on-line electrodes, diamond-on-line electrodes, castellated electrodes, or sinusoidal electrodes. Characteristic dimensions of these electrode geometries may vary from as small as less than 5 micron, or less than 10 micron, to as large as over 200 micron, over 500 micron, over 1 mm. The characteristic dimensions of the electrode geometries refer to the smallest width of the electrode elements, or smallest gaps between the adjacent electrode elements, or size of a repeating feature on the electrode geometries. The microelectrode strip can be of any geometry for the present invention. One exemplary geometry for the microelectrode strips is rectangular shape—having the width of the strip between less than 50 micron to over 10 mm, and having the length of the strip between less than 60 micron to over 15 mm. An exemplary geometry of the microelectrode strips may have a geometry having a width of 200 micron and a length of 20 mm. A single microelectrode strip may have two electrodes serving as a measurement unit, or multiple such two-electrodes serving as multiple measurement units, or a single electrode structure unit as a measurement unit, or multiple electrode structure units serving as multiple electrode structure units. In one exemplary embodiment, when multiple electrode structure units are fabricated on a single microelectrode strip, these electrode structure units are positioned along the length direction of the strip. The electrode structure units may be of squared-shape, or rectangular-shape, or circle shapes. Each of electrode structure units may occupy size from less than 50 micron by 50 micron, to larger than 2 mm×2 mm.

As used herein, "sample" refers to anything which may contain a moiety to be isolated, manipulated, measured, quantified, detected or analyzed using apparatuses, microplates or methods in the present application. The sample may be a biological sample, such as a biological fluid or a biological tissue. Examples of biological fluids include suspension of cells in a medium such as cell culture medium, urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples may further include cell suspensions, solutions containing biological molecules (e.g. proteins, enzymes, nucleic acids, carbohydrates, chemical molecules binding to biological molecules).

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

A "biologically active agent" or "biologically active agent" is any agent which has an effect on the physiology of the cell. The non-limiting examples of such direct or indirect effect or effects are effects on cells viability, cell adhesion, apoptosis, cell differentiation, cell proliferation, cell morphology, cell cycle, IgE-mediated cell activation or stimulation, receptor-ligand binding, receptor-activation, cellular signaling pathways, cell number, cell quality, cell cycling, cell spreading. A biologically active agent can be any agent, including, but not limited to, a small molecule, a large molecule, a molecular complex, an organic molecule, an inorganic molecule, a biomolecule or biological molecule such as but not limited to a lipid, a steroid, a carbohydrate, a fatty acid, an amino acid, a peptide, a protein, a nucleic acid, or any combination thereof. A biologically active agent can be a synthetic compound, a naturally occurring compound, a derivative of a naturally-occurring compound, etc. The structure of a biologically active agent can be known or unknown.

A "known biologically active agent" is a compound or agent for which at least one activity is known. In the present invention, a known biologically active agent preferably is a compound or agent for which one or more direct or indirect effects on cells is known. Preferably, the structure of a known biologically active agent is known, but this need not be the case. Preferably, the mechanism of action of a known biologically active agent on cells is known, for example, the effect or effects of a known biologically active agent on cells can be, as nonlimiting examples, effects on cell viability, cell adhesion, apoptosis, cell differentiation, cell proliferation, cell morphology, cell cycle, IgE-mediated cell activation or stimulation, receptor-ligand binding, G-protein coupled receptor activation, receptor tyrosine kinase activation, cell number, cell quality, cell cycling, cell spreading, cell signaling, etc.

An "unknown biologically active agent" is a biologically active agent which has or may have the capacity to induce changes in cellular physiology or to exert direct or indirect effects on cells by an unknown mechanism or yet to be defined mechanism.

An "impedance value" is the impedance measured for electrodes in a well with or without cell present. Impedance is generally a function of the frequency, i.e., impedance values depend on frequencies at which the measurement was conducted. For the present application, impedance value refers to impedance measured at either single frequency or multiple frequencies. Furthermore, impedance has two components, one resistance component and one reactance component. Impedance value in the present application refers to resistance component, or reactance component, or both resistance and reactance component. Thus, when "impedance value" was measured or monitored, we are referring to that, resistance, or reactance, or both resistance and reactance were measured or monitored. In many embodiments of the methods of the present application, impedance values also refer to parameter values that are derived from raw, measured impedance data. For example, cell index, or normalized cell index, or delta cell index could be used to represent impedance values.

A "Cell Index" or "CI" is a parameter that can derived from measured impedance values and that can be used to reflect the change in impedance values. There are a number of methods to derive or calculate Cell Index. Description of "cell index", "normalized cell index", "delta cell-index" and "cell change index" can be found in U.S. patent application Ser. Nos. 10/705,447, 10/987,732 and 11/055,639, and in U.S. Pat. No. 7,192,752, herein incorporated by reference for all description and disclosure regarding these parameters including "cell index", "normalized cell index", "delta cell-index" and "cell change index".

A "Normalized Cell Index" at a given time point is calculated by dividing the Cell Index at the time point by the Cell Index at a reference time point. Thus, the Normalized Cell Index is 1 at the reference time point. Generally, the reference time point is the last time point of measurement just prior to treatment of cells with biologically active agents.

A "delta cell index" at a given time point is calculated by subtracting the cell index at a standard time point from the cell index at the given time point. Thus, the delta cell index is the absolute change in the cell index from an initial time (the standard time point) to the measurement time. Generally, the standard time point is the last time point of measurement just prior to treatment of cells with biologically active agents.

A "Cell Change Index" or "CCI" is a parameter derived from Cell Index and "CCI" at a time point is equal to the $1^{st}$ order derive of the Cell Index with respect to time, divided by the Cell Index at the time point. In other words, CCI is calculated as $$CCI(t) = \frac{dCI(t)}{CI(t) \cdot dt}.$$

As used herein, "target cell" or "target cells" refers to any cell that is to be monitored for its response to one or more biologically active agents. Generally, the reference time point is the last time point of measurement just prior to treatment of cells with biologically active agents. Non-limiting examples of target cells include eukaryotic or prokaryotic cells of interest. Eukaryotic cells of particular interest may be human cells, a human cell population or a human cell line. Immune cells may be utilized such as B-lymphocytes, T-lymphocytes Natural Killer (NK) cells, Cytotoxic T-Lymphocytes (CTLs), neutrophils, easonophils, macrophages, Natural Killer T (NKT) cells, PBMCs and the like.

As used herein, "primary cell" or "primary cells" refers to any non-immortalized cell that has been derived from various tissues and organs of a patient or an animal.

As used herein "a mechanism-specific type or group" refers to a group of impedance-based or cell index-based curves that display similar response profiles to biologically active agents with a known mechanism; for example all anti-mitotic agents display similar response profile and therefore are referred to as an anti-mitotic (mechanism-specific) type of curves. The impedance-based curves or cell-index curves in a mechanism-specific response profile group have sufficient similarities in the curve profiles. In the present invention, biologically active agents having the same mechanism (of action on cells) would result in sufficient similar response profiles displayed by cells treated with these biologically active agents. A mechanism-specific response profile group or type may be defined by one impedance-based or cell index-based curve for cells treated with a known biologically active agent. Alternatively, a mechanism-specific response profile group or type may be defined by more than one impedance-based or cell index-based curves that display similar response profiles to multiple biologically active agents with a known mechanism.

As used herein "response profile" refers to a time-dependent change in impedance or cell index as a result of cell treatment with biologically active agents.

As used herein, "significant difference between impedance- or cell index-based curves" is a difference being defined as any changes relative to control that are greater or equal to 2% of impedance value or Cell Index value at any given time point. Preferably, impedance-based or cell index-based curves for a biologically active agent being "significantly different" from that of the control means that at least one time point in the curves, there are greater than 2%, greater than 3%, greater than 5%, greater than 10%, greater than 15%, or greater than 20% differences between impedance values or cell index values for biologically active agents and the control. Even more preferably, impedance-based or cell index-based curves for a biologically active agent being "significantly different" from that of the control refers to that at multiple time points in the curves, there are greater than 2%, greater than 3%, greater than 5%, greater than 10%, greater than 15%, or greater than 20% differences between impedance values or cell index values for biologically active agents and the control. There are other ways to determine whether impedance-based or cell index-based curves for a biologically active agent is "significantly different" from that of the control. For example, if the "correlation coefficient" between two curves is less than a pre-determined value (for example, 0.7 or 70%), then the two curves under comparison are termed "significantly different". In this example, this pre-determined value for "having the significance difference" may be different for different applications. In another example, if the values for "a single characteristic parameter" for two curves differ by more than a pre-determined value (for example, 10%), then the two curves under comparison are termed "significantly different". Similar to the example above, this pre-determined value for "having the significance difference" may be different for different applications. In yet another example, if the distance between two curves is larger than a pre-determined value, then the two curves under comparison are termed "significantly different". Like the above two examples, the pre-determined value for "having the significance difference" may be different for different applications. One aspect of the present invention is directed to a method for comparing and categorizing cell responses to biologically active agents. Thus, the time periods used for comparing impedance-based curves or cell index curves to determine whether "significant difference" exists are generally time periods after cells being treated with biologically active agents or the control.

As used herein, "predetermined mechanism-specific cellular response profile group" is an impedance or cell index-based cellular response profile group that has previously been shown to represent a specific mechanism.

As used herein, "correlation coefficient" is a parameter describing the relative similarity between any two curves. For two given curves, one being $C_1(t_i); \{i=1, 2, 3, \ldots N\}$, and another being $C_2(t_i); \{i=1, 2, 3, \ldots N\}$, The correlation coefficient between these two curves is calculated using this approach, $$CC(1,2) = \frac{N\sum_i [C_1(t_i)C_2(t_i)] - \sum_i C_1(t_i) \cdot \sum_i C_2(t_i)}{\sqrt{[N\sum_i [C_1(t_i)]^2 - (\sum_i C_1(t_i))^2] \cdot [N\sum_i [C_2(t_i)]^2 - (\sum_i C_2(t_i))^2]}}.$$

One aspect of the present invention is directed to a method for comparing and categorizing cell responses to biologically active agents. Thus, time periods used for calculating correlation coefficients above (for either impedance-based curves or cell index curves) are generally a time period after cells being treated with biologically active agents.

As used herein, "curve classification" is the process of comparing at least two curves and categorizing or classifying these curves into one or more groups. Since the curve classification is for comparing and categorizing cell responses to biologically active agents, the curves used in these analyses refer to portions of curves after cells being treated with biologically active agents.

As used herein, "curve classification algorithm" is an algorithm that performs curve classification. Curve classification algorithms may be programmed into a computer with appropriate software.

As used herein, "two impedance-based or cell index-based curves are 'sufficiently similar'" means that when comparing these curves for their similarity using a mathematical calculation method, the calculated result meets a "similarity threshold". For example, when "correlation coefficient" is used to calculate the similarity between two curves, the two curves are "sufficiently similar" if the correlation coefficient between the two curves is more than 0.9 (90%). Here, 0.9 (90%) is a "similarity threshold". The similarity threshold may attain different values (for example, 0.95 or 0.87), depending on specific application conditions of the invention. In another example, "single characteristic parameter" is used to calculate the similarity between two curves. Two curves are "sufficiently similar" if values for such characteristic parameter for the two curves differ less than 10%. Here, 10% is a similarity threshold. The similar threshold may have other values (for example, 5% or 12%), depending on specific application conditions of the invention. In still another example, "distance between curves" is calculated for comparing two curves and for determining similarity between curves. In this case, two curves are "sufficiently similar" if distance between the two curves is smaller than a "similarity threshold value". Like the above two example, the similarity threshold may have different values, depending on specific application conditions of the invention. Since the determination of whether two curves are sufficiently similar is for the purpose of comparing and categorizing cell responses to biologically active agents, the time periods used for comparing impedance-based curves or cell index curves to determine whether "sufficient similarity" exists are generally time periods after cells being treated with biologically active agents or the control.

As used herein, "an impedance-based or cell index-based curve is 'sufficiently similar' to one predetermined mechanism-specific cellular response profile group" means that said impedance-based or cell index-based curve is sufficiently similar to at least one cell response profile in the said predetermined mechanism-specific cellular response profile group. In the case of "distance between curves" being used to determine whether "sufficient similarity" exists between two curves, "distance between a curve and a curve group" can be used to determine whether an impedance-based or cell index-based curve is 'sufficiently similar' to one predetermined mechanism-specific cellular response profile group. In this case, if the distance between an impedance-based or cell index-based curve and a predetermined mechanism-specific cellular response profile group is smaller than a "similarity threshold", then this impedance-based or cell index-based curve is sufficiently similar to the predetermined mechanism-specific cellular response profile group. Since the determination of whether a curve is "sufficiently similar" to a predetermined mechanism-specific cellular response profile group is for the purpose of categorizing cell responses to biologically active agents, the time periods used for comparing impedance-based curve or cell index curve with those of a mechanism-specific cellular response profile group to determine whether "sufficient similarity" exists are generally time periods after cells being treated with biologically active agents or the control.

As used herein, an impedance-based or cell index-based curve is 'sufficiently similar' to a curve group means that said impedance-based or cell index-based curve is sufficiently similar to at least one curve in the said curve group. In the case of "distance between curves" being used to determine whether "sufficient similarity" exists between two curves, "distance between a curve and a curve group" can be used to determine whether an impedance-based or cell index-based curve is 'sufficiently similar' to a curve group. In this case, if the distance between an impedance-based or cell index-based curve and the curve group is smaller than a "similarity threshold", then this impedance-based or cell index-based curve is sufficiently similar to the existing curve group. Since the determination of whether a curve is "sufficiently similar" to a curve group is for the purpose of categorizing cell responses to biologically active agents, the time periods used for comparing impedance-based curves or cell index curves with curve groups to determine whether "sufficient similarity" exists are generally time periods after cells being treated with biologically active agents or the control.

As used herein, "two curves have 'sufficient similarity'" means that the two curves are sufficiently similar.

As used herein, "single characteristic parameters" is single parameter that is calculated from a curve and can reflect overall characteristics or properties of the curve. There may be more than one methods to define such "single characteristic parameter". For example, single characteristic parameter may be a peak value in a time range along an impedance-based or cell index-based curve. In another example, single characteristic parameter may be an area-under-the-curve in a time range along an impedance-based or cell index based curve. Since the determination of single characteristic parameter is for the purpose of comparing and categorizing cell responses to biologically active agents, the time period used for calculating single characteristic parameters is generally a time period after cells being treated with biologically active agents or the control.

As used herein, "distance between curves" refers to a "distance" parameter calculated for two curves. There may be more than one method to define "distance between curves". In one example, the distance is the sum of square of the difference of the two curves at a set of given time points. For two given curves, one being $C_1(t_i); \{i=1, 2, 3, \ldots N\}$, and another being $C_2(t_i); \{i=1, 2, 3, \ldots N\}$, the distance between the two curves can be defined as $$d_{C_1 C_2} = \sum_{i=1}^{N} (C_1(t_i) - C_2(t_i))^2.$$

The distance between curves is calculated to determine the similarity between curves and thus determines which mechanism specific cellular response profile group is associated with the curve. Further details about "distance between curves" can be found in later sections of the present invention. Since the determination of "distance between curves" is for the purpose of comparing and categorizing cell responses to biologically active agents, the time period used for calculating "distance between curves" is generally a time period after cells being treated with biologically active agents or the control.

Overview of the Systems and Methods

The present invention provides a cell-based phenotypic profiling approach for dynamic monitoring, profiling, and categorizing the effects of biologically active agents on live cells. The approach is based on impedance monitoring, or impedance measurement over time, of cells growing on microelectronic sensors integrated in wells of microtiter plates. The impedance of cells is a function of the number of cells seeded on the electrodes, the morphology of the cells and the quality of adhesion. Because all of these three parameters can be differentially modulated temporally in a manner that is dependent on the biological mechanism of biologically active agents, impedance-based monitoring, or impedance measurements taken over time, before and after treatment with biologically active agents results in kinetic signature profiling of live cells, which is reflective and predictive of biological activity of biologically active agent. Such kinetic signature profiles can be categorized into different mechanism specific cellular response profile groups, each of which associated with a specific mechanism resulting from biologically active agents acting on the cells.

In one aspect of the present invention cell responses to known biologically active agents are categorized into mechanism-specific cell response profile groups. These groups are defined by generating curves obtained or derived from impedance measurements of cells, over time, treated with known biologically active agents and comparing the curves to one or more curves obtained from control samples. Mechanism specific cellular response profile groups are established or defined when impedance derived curves generated from cells treated with biologically active agents are significantly different from control. Significant difference may depend on a threshold identified by a user and may vary from experiment to experiment or data set to data set. Groups can be further defined or established by comparing multiple curves generated from cells treated with one or more biologically active agents having similar mechanisms.

In another aspect of the present invention, cell responses to unknown biologically active agents are categorized into predetermined mechanism-specific response profile groups. The methods include generating impedance-based curves, cell-index curves or normalized cell index curves from cells treated with unknown biologically active agents and comparing the curves to pre-determined, mechanism-specific cellular response profile groups. The degree of similarity between impedance-based curves generated from treated cells with the pre-determined mechanism-specific response groups determines whether the biologically active agent is categorized into the corresponding group. Thus, cellular responses to unknown biologically active agents can be categorized into at least one of the particular pre-determined mechanism-specific cellular response profile groups if the curves of the cell response to unknown biologically active agents and pre-determined mechanism-specific response groups, whether impedance-based curves, cell-index curves or normalized cell index curves, are sufficiently similar. The categorization of curves obtained from cells treated with unknown biologically active agents into pre-determined groups allows for the identification of a potential or likely response mechanism or phenotype.

In yet another aspect of the present invention, cell responses to biologically active agents are categorized into different groups. The methods include generating impedance-based curves, cell-index curves or normalized cell index curves from cells treated with multiple biologically active agents and comparing the curves between each other. The degree of similarity between impedance-based curves generated from cells treated with different biologically active agents determines how different biologically active agents are categorized into one or more groups. Thus, cellular responses to two biologically active agents can be categorized into one group if the curves of the cell responses to these two biologically active agents, whether impedance-based curves, cell-index curves or normalized cell index curves, are sufficiently similar. Furthermore, cellular response to one biologically active agent can be categorized into one existing curve group if the cell response curves to said biologically active agent, whether impedance-based curve, cell-index curve or normalized cell index curve, is sufficiently similar to the curves in the existing group. Thus, "comparing impedance-based curves or cell index curves to one another and categorizing said impedance-based or cell index curves into one or more groups according to the presence or absence of at least sufficient similarity" refers to a process of comparing any two curves (impedance-based curves or cell index curves) and classifying two curves into one group if the two curves are "sufficiently similar". Furthermore, if a curve is sufficiently similar to an existing curve group, then this curve is classified into this existing group.

Devices for Monitoring or Measuring Cell-Substrate Impedance

The systems and methods of the present invention utilize impedance-based systems for monitoring or detecting changes in impedance in response to the exposure or introduction of one or more biologically active agents to cells. Suitable impedance-based devices are those that are capable of detecting changes in impedance of a cell population. Detecting changes in impedance of cells requires the cells to attach to the electrode array during at least partial time in the experiment test. For example, cells may attach to the electrode array before the treatment with biologically active agents and its attachment status may or may not be affected by biologically active agents. In another example, cells do not attach to the electrode array before the treatment with biologically active agents and cells become attached to the electrode array after being exposed to biologically active agents. Thus, the substrate must be biocompatible with the cell or cell population.

Generally, impedance-based devices include a conductive electrode array fabricated on a non-conductive substrate and operably connected to an impedance analyzer. A computer loaded with appropriate software may be used to operate the system and may also be used in analysis of impedance measurements, such as in the generation or comparison of impedance-based or derived curves. More specifically, the impedance-based device may include a nonconducting substrate; two or more electrode arrays fabricated on the substrate, where each of the two or more electrode arrays comprises two electrode structures; and at least two connection pads, each of which may be located on an edge of the substrate. In preferred embodiments the electrode array is planar or substantially planar.

Preferably, each electrode array of the device has approximately uniform electrode resistance across the entire array. In some embodiments, the substrate of the device has a surface suitable for attaching a biological molecule or organic compound (such as covalently or noncovelently bonding). The substrate may also be suitable for a attaching a cell where cell attachment or spreading on the substrate can result in a detectable change in impedance between or among the electrode structures within each electrode array.

An electrode array may be two or more electrode structures that are constructed to have dimensions and spacing such that they can, when connected to a signal source, operate as a unit to generate an electrical field in the region of spaces around the electrode structures. An electrode structure refers to a single electrode, particularly one with a complex structure (for example, an electrode structure can comprise two or more electrode elements that are electrically connected together). In devices utilized with the present invention, an electrode array comprises two electrode structures, each of which comprises multiple electrode elements, or substructures. In preferred embodiments of the present invention, the electrode structures of each of the two or more electrode arrays of a device have substantially the same surface area. In preferred embodiments of a device of the present invention, each of the two or more electrode arrays of a device comprise two electrode structures, and each electrode structure comprises multiple electrode elements. Each of the two electrode structures of an electrode array is connected to a separate connection pad that may be located at the edge of the substrate.

Thus, in devices of the present invention, for each of the two or more electrode arrays of the device, the first of the two electrode structures is connected to one of the two or more connection pads, and the second of the two electrode structures is connected to another of the two or more connection pads. Preferably, each array of a device is individually addressed, meaning that the electrical traces and connection pads of the arrays are configured such that an array can be connected to an impedance analyzer in such a way that a measuring voltage can be applied across a single array at a given time by using switches (such as electronic switches).

Each electrode array of the device has an approximately uniform electrode resistance distribution across the entire array. By "uniform resistance distribution across the array" is meant that when a measurement voltage is applied across the electrode structures of the array, the electrode resistance at any given location of the array is approximately equal to the electrode resistance at any other location on the array. Preferably, the electrode resistance at a first location on an array of the device and the electrode resistance at a second location on the same array does not differ by more than 30%. More preferably, the electrode resistance at a first location on an array of the device and the electrode resistance at a second location on the same array does not differ by more than 15%. Even more preferably, the electrode resistance at a first location on an array of the device and a second location on the same array does not differ by more than 5%. More preferably yet, the electrode resistance at a first location on an array of the device and a second location on the same array does not differ by more than 2%.

For a device utilized with the present invention, preferred arrangements for the electrode elements, gaps between the electrodes and electrode buses in a given electrode array are used to allow all cells, no matter where they land and attach to the electrode surfaces, to contribute similarly to the total impedance change measured for the electrode array. Thus, it is desirable to have similar electric field strengths at any two locations within any given array of the device when a measurement voltage is applied to the electrode array. At any given location of the array, the field strength is related to the potential difference between the nearest point on a first electrode structure of the array and the nearest point on a second electrode structure of the array. It is therefore desirable to have similar electric potential drops across the electrode elements and across the electrode buses of a given array. Based on this requirement, it is preferred to have an approximately uniform electrode resistance distribution across the whole array where the electrode resistance at a location of interest is equal to the sum of the electrode resistance between the nearest point on a first electrode structure (that is the point on the first electrode structure nearest the location of interest) and a first connection pad connected to the first electrode structure and the electrode resistance between the nearest point on a second electrode structure (that is the point on the first electrode structure nearest the location of interest) and a second connection pad connected to the second electrode structure.

Devices of the present invention are designed such that the arrays of the device have an approximately uniform distribution across the whole array. This can be achieved, for example, by having electrode structures and electrode buses of particular spacing and dimensions (lengths, widths, thicknesses and geometrical shapes) such that the resistance at any single location on the array is approximately equal to the resistance at any single other location on the array. In most embodiments, the electrode elements (or electrode structures) of a given array will have even spacing and be of similar thicknesses and widths, the electrode buses of a given array will be of similar thicknesses and widths, and the electrode traces leading from a given array to a connection pad will be of closely similar thicknesses and widths. Thus, in these preferred embodiments, an array is designed such that the lengths and geometrical shapes of electrode elements or structures, the lengths and geometrical shapes of electrode traces, and the lengths and geometrical shapes of buses allow for approximately uniform electrode resistance distribution across the array.

In some preferred embodiments of cell-substrate impedance measurement devices, electrode structures comprise multiple electrode elements, and each electrode element connects directly to an electrode bus. Electrode elements of a first electrode structure connect to a first electrode bus, and electrode elements of a second electrode structure connect to a second electrode bus. In these embodiments, each of the two electrode buses connects to a separate connection pad via an electrical trace. Although the resistances of the traces contribute to the resistance at a location on the array, for any two locations on the array the trace connections from the first bus to a first connection pad and from the second bus to a second connection pad are identical. Thus, in these preferred embodiments trace resistances do not need to be taken into account in designing the geometry of the array to provide for uniform resistances across the array.

In preferred embodiments of the present invention, a device for monitoring cell-substrate impedance has two or more electrode arrays that share a connection pad. Preferably one of the electrode structures of at least one of the electrode arrays of the device is connected to a connection pad that also connects to an electrode structure of at least one other of the electrode arrays of the device. Preferably for at least two arrays of the device, each of the two or more arrays has a first electrode structure connected to a connection pad that connects with an electrode structure of at least one other electrode array, and each of the two or more arrays has a second electrode structure that connects to a connection pad that does not connect with any other electrode structures or arrays of the device. Thus, in preferred designs of a device there are at least two electrode arrays each of which has a first electrode structure that is connected to a common connection pad and a second electrode structure that is connected to an independent connection pad.

In some preferred embodiments of the present invention, each of the electrode structures of an array is connected to an electrode bus that is connected to one of the two or more connection pads of the device via an electrically conductive trace. In preferred embodiments, each of the two electrode structures is connected to a single bus, such that each array connects to two buses, one for each electrode structures. In this arrangement, each of the two buses connects to a separate connection pad of the substrate.

The electrically conductive traces that connect a bus with a connection can be fabricated of any electrically conductive material. The traces can be localized to the surface of the substrate, and can be optionally covered with an insulating layer. Alternatively the traces can be disposed in a second plane of the substrate. Description of arrangements and design of electrically conductive traces on impedance measurement devices can be found in parent U.S. patent application Ser. No. 10/705,447, herein incorporated by reference for all disclosure on fabrication and design of electrically conductive trace on substrates.

Appropriate electronic connection means such as metal clips engaged onto the connection pads on the substrate and connected printed-circuit-boards can be used for leading the electronic connections from the connection pads on the devices to external electronic circuitry (e.g. an impedance analyzer). Description of the design of cell-substrate impedance devices and their manufacture can be found in U.S. patent application Ser. No. 10/705,447, herein incorporated by reference for all description and disclosure of the design, features, and manufacture of impedance device comprising electrode arrays.

Preferably the nonconducting substrate is planar, and is flat or approximately flat. Exemplary substrates can comprise many materials, including, but not limited to, silicon dioxide on silicon, silicon-on-insulator (SOI) wafer, glass (e.g., quartz glass, lead glass or borosilicate glass), sapphire, ceramics, polymer, fiber glass, plastics, e.g., polyimide (e.g. Kapton, polyimide film supplied by DuPont), polystyrene, polycarbonate, polyvinyl chloride, polyester, polypropylene and urea resin. Preferably, the substrate and the surface of the substrate are not going to interfere with molecular binding reactions that will occur at the substrate surface. For cell-substrate impedance monitoring, any surface of the nonconducting substrate that can be exposed to cells during the use of a device of the present invention is preferably biocompatible. Substrate materials that are not biocompatible can be made biocompatible by coating with another material, such as polymer or biomolecular coating.

All or a portion of the surface of a substrate can be chemically treated, including but not limited to, modifying the surface such as by addition of functional groups, or addition of charged or hydrophobic groups.

In some embodiments a portion of the surface of the substrate is modified to include some coated molecules. Example of coated molecules that may be desired include those that are involved or may be involved in cell adhesion or cell spreading. The present invention includes a variety of coated molecules including a DNA molecule, an RNA molecule, a protein, a polypeptide and oligopeptide and the like. Molecules of particular interest may include an antibody, a ligand, a peptide, a receptor, one or more proteins or compounds present in the extracellular matrix (ECM), a molecule or compound capable of binding an integrin, a cell surface receptor and the like. In some embodiments a peptide such as an arginine-glycine-aspartic acid (RGD) motif or some form thereof is the coated molecule. The present invention also includes coated molecules that are agonists or antagonists for a cell surface receptor involved in cell adhesion, including integrins, growth factor receptors, E-cadherins, N-cadherins, PECAMS and ICAMS.

The modification may ultimately result in a coated surface or a surface that is coated at least in part with a coated molecule. The coated portion may represent a first portion, a second portion and the like. The region may also be referred to as a test portion or a control portion depending on the assay. When utilizing wells with the present invention, an inner surface of the wells may be coated at least in part with a coated molecule. The coated molecules may interact with the substrate in any suitable fashion. For example, the coated molecules may be covalently bound, ionically bound, bound by Van der Waals forces and the like to the substrate or electrode. The coated molecules may be attached directly to the substrate or electrode or may be attached via an intermediate structure. As a nonlimiting example, coated molecules may be bound by incubating the coated molecule in a suitable medium such as phosphate buffered saline (PBS), borate buffered saline (BBS) and the like. Alternatively, an intermediate such as poly-L-lysine may be applied to the substrate then attached to the coated molecules.

Descriptions of electrode arrays used for impedance measurement that apply to the devices of the present invention are described in U.S. patent application Ser. No. 10/705,447, herein incorporated by reference for all disclosure relating to electrode arrays (or structural units), electrode structures, electrode materials, electrode dimensions, and methods of manufacturing electrodes on substrates.

Preferred electrode arrays for devices of the present invention include arrays comprising two electrode structures, such as, for example, spiral electrode arrays and interdigitated arrays. In some preferred devices of the present invention, electrode arrays are fabricated on a substrate, in which the arrays comprises two electrode structures, each of which comprises multiple circle-on-line electrode elements, in which the electrode elements of one structure alternate with the electrode elements of the opposite electrode structure. In a preferred embodiment the electrical circuitry includes gold-coated interdigitated microelectrodes (or electrode structures) in a circle-on-line geometry. Although, additional electrode geometries are possible, the circle-on-line geometry maximizes the coverage area in a single microtiter well with maximal sensitivity.

Preferably, the electrode elements (or electrode structures) of an array of the present device of the present invention are of approximately equal widths. Preferably the electrode elements (or electrode structures) of an array of the present device of the present invention are greater than 30 microns in width, more preferably from about 50 to about 300 microns in width, and more preferably yet about 90 microns in width.

Preferably, the electrode elements (or electrode structures) of an array of the present device of the present invention are approximately evenly spaced. Preferably, the gap between electrode elements (or electrode structures) of an array of the present device of the present invention is less than 50 microns in width, more preferably from about 5 to about 30 microns in width, and more preferably yet about 20 microns in width.

A device of the present invention can include one or more fluid-impermeable receptacles, which serve as fluid containers. Such receptacles may be reversibly or irreversibly attached to or formed within the substrate or portions thereof (such as, for example, wells formed as in a microtiter plate). In another example, the device of the present invention includes microelectrode strips reversibly or irreversibly attached to plastic housings that have openings that correspond to electrode structure units located on the microelectrode strips. Suitable fluid container materials comprise plastics, glass, or plastic coated materials such as ceramics, glass, metal, etc. Descriptions and disclosure of devices that comprise fluid containers can be found in parent U.S. patent application Ser. No. 10/705,447, herein incorporated by reference for all disclosure of fluid containers and fluid container structures that can engage a substrate comprising electrodes for impedance measurements, including their dimensions, design, composition, and methods of manufacture.

In preferred embodiments, each electrode array on the substrate of a device of the present invention is associated with a fluid-impermeable container or receptacle, such as, for example, a well. Preferably, the device of the present invention is assembled to a bottomless, multiwell plastic plate or strip with a fluid tight seal. The device is assembled such that a single array of the substrate is at the bottom of a receptacle or well. Preferably, each array of a device is associated with a well of a multiwell plate. In some preferred embodiments, a multiwell device for cell-substrate impedance measurement has "non-array" wells that are attached to the substrate but not associated with arrays. Such wells can optionally be used for performing non-impedance based assays, or for viewing cells microscopically.

The design and assembly of multiwell impedance measurement devices is described in U.S. patent application Ser. Nos. 10/705,447, 10/987,732, 11/055,639, and U.S. Pat. No. 7,192,752, all herein incorporated by reference for disclosure of multiwell impedance measurement devices, including their design, composition, and manufacture. A device of the present invention preferably has between 2 and 1,536 wells, more preferably between 4 and 384 wells, and even more preferably, between 16 and 96 wells, all or less than all or which are associated with electrode arrays. In the preferred embodiments cells are added to 16, 24, 96, 384 or 1536 wells since these are commonly available well configurations.

In some preferred embodiments, commercial tissue culture plates can be adapted to fit a device of the present invention. Bottomless plates may also be custom-made to preferred dimensions. Preferably, well diameters are from about 1 millimeter to about 20 millimeters, more preferably from about 2 millimeters to about 8 millimeters at the bottom of the well (the end disposed on the substrate). The wells can have a uniform diameter or can taper toward the bottom so that the diameter of the container at the end in contact with the substrate is smaller than the diameter of the opposing end.

Introducing Cells to the Device

Cells are typically added to the wells of the device by transferring a cell suspension into the desired well. Cells may be added to at least two, at least three or more of the wells. Thus, cells may be added to all wells or less than all wells. In various embodiments, cells are added to 2, 4, 16, 96, 384 or 1,586 wells. Cells may be incubated within the wells, such as to allow the cells sufficient time to settle down to the electrode array. In other embodiments incubation permits a cell population to stabilize and thus provide a baseline impedance value that does not significantly vary. Cells may be incubated or cultivated in the wells overnight, over multiple nights or over weeks depending on the desired experiment. Cells, such as those derived from a cell line, may be seeded in one or more wells then incubated until a desired population is reached. Alternatively, cells such as those isolated from a human may be added to wells upon isolation and incubated less than one 24 hour day, 6 hours, 2 hours, 1 hour or less than 1 hour prior to beginning an experiment.

Figure 1B:
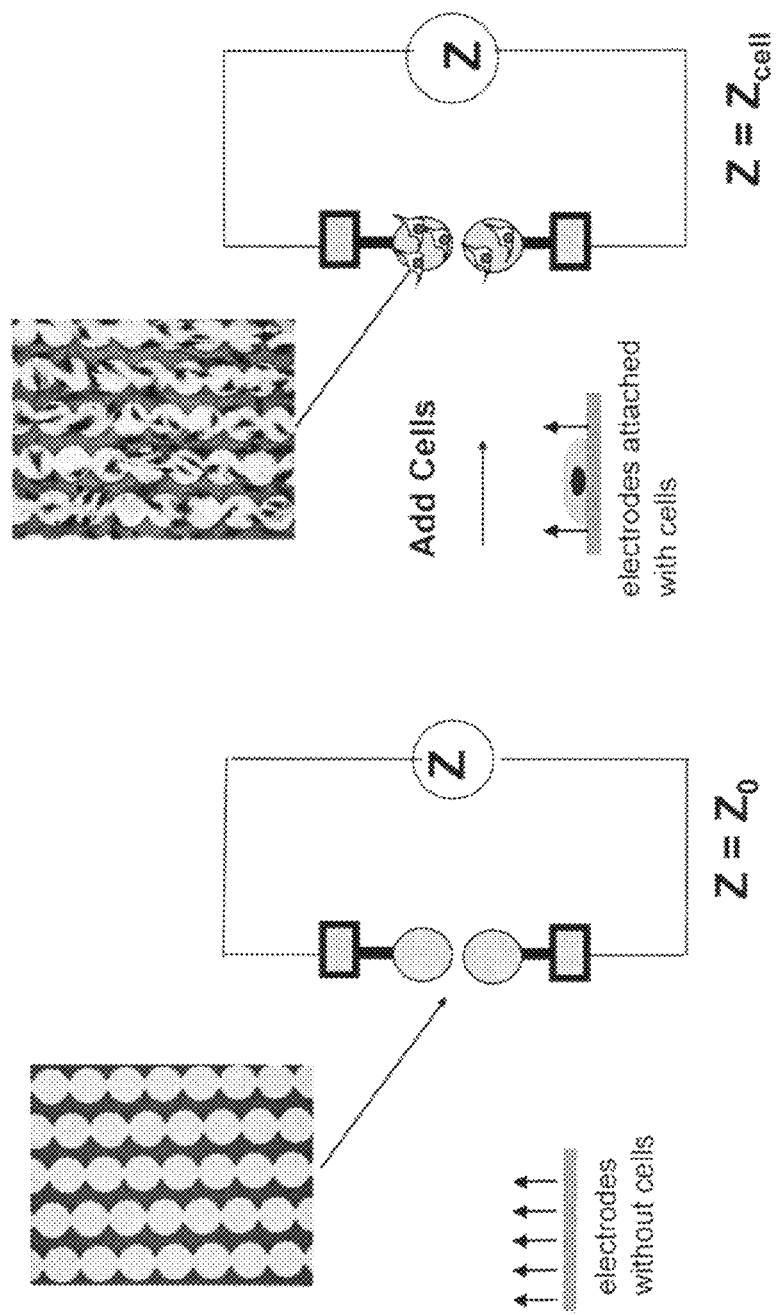
FIG. 1B demonstrates the interaction of mammalian cells with the electrode leads to an increase in cell substrate impedance response.

With respect to the cells themselves, the present systems, methods and devices may be used with any desired cell or cell type. Cells may be the same or different. Examples include prokaryotic or eukaryotic cells. In preferred embodiments, the cells are mammalian and more preferably human. Cells may be isolated from a tissue such as from an organ, blood and the like. Cells may be primary cells, a cell line or derived from a cell line, engineered cells expressing a specific protein or sets of proteins and the like. Cells may be cultured prior to addition to the wells, such as to remove biological moieties bound or associated with the cell. Thus, cell type is intended to be nonlimiting. FIG. 1 is a micrograph of mammalian cells seeded on circle-on-line gold microelectrodes integrated in the bottom of a single microtiter well. The impedance readout is generated by application of 20 mV AC current and the resulting impedance is measured at three frequencies; 10 kHz, 25 kHz and 50 kHz. An arbitrary unit called Cell Index is derived by taking the ratio of resistance (an impedance component) of the electrodes with the cells (in the presence of growth media) to electrodes with media alone (background impedance). Description of "cell index", "normalized cell index", "delta cell-index" and "cell change index" can be found in U.S. patent application Ser. Nos. 10/705,447, 10/987,732 and 11/055,639, and in U.S. Pat. No. 7,192,752, herein incorporated by reference for all description and disclosure regarding these parameters including "cell index", "normalized cell index", "delta cell-index" and "cell change index".

Monitoring Impedance Over Time

Impedance may be monitored over a predetermined or variable period of time. Preferably impedance monitoring begins prior to the addition of a biologically active agent and may begin prior to the addition of a cell suspension to the well. Impedance monitoring may assist in determining the point in which cells are suited for the introduction of a biologically active agent. In the preferred embodiment impedance is monitored continuously over time and does not require specific time point measurements. Impedance is preferably measured in real time. Suitable time periods may be predetermined such as over a desired number of seconds, minutes, hours, days, weeks and the like or impedance may be monitored until the user decides to stop impedance monitoring, such as at some time after treatment of cells with biologically active agents when no change or no significant change in impedance value occurs.

Figure 2:
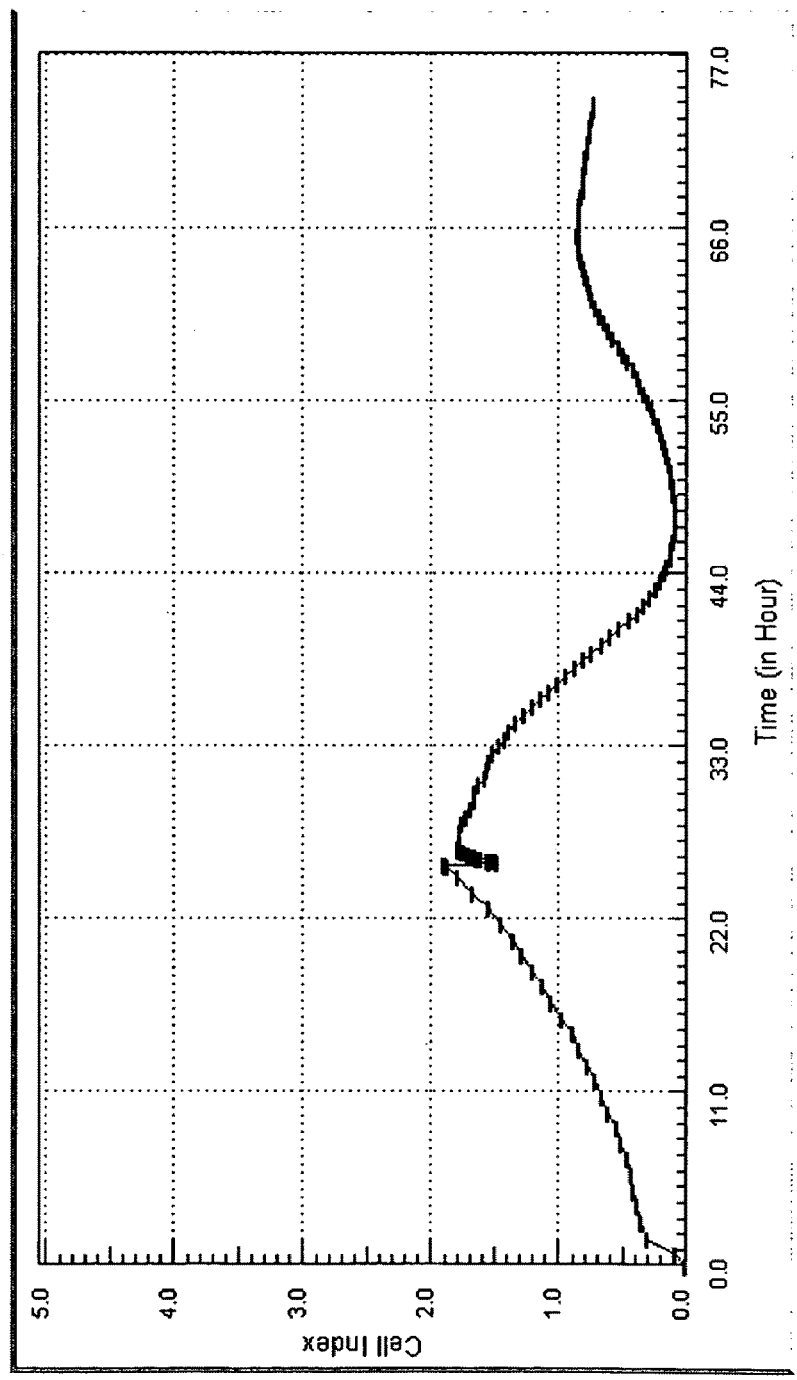
FIG. 2 is a graphical representation of a cell index curve over a time period depicted by plotting Cell Index (Y-axis) vs. Time (X-axis), where cells were treated with a biologically active agent at a time point ~21 hr.
Figure 4A:
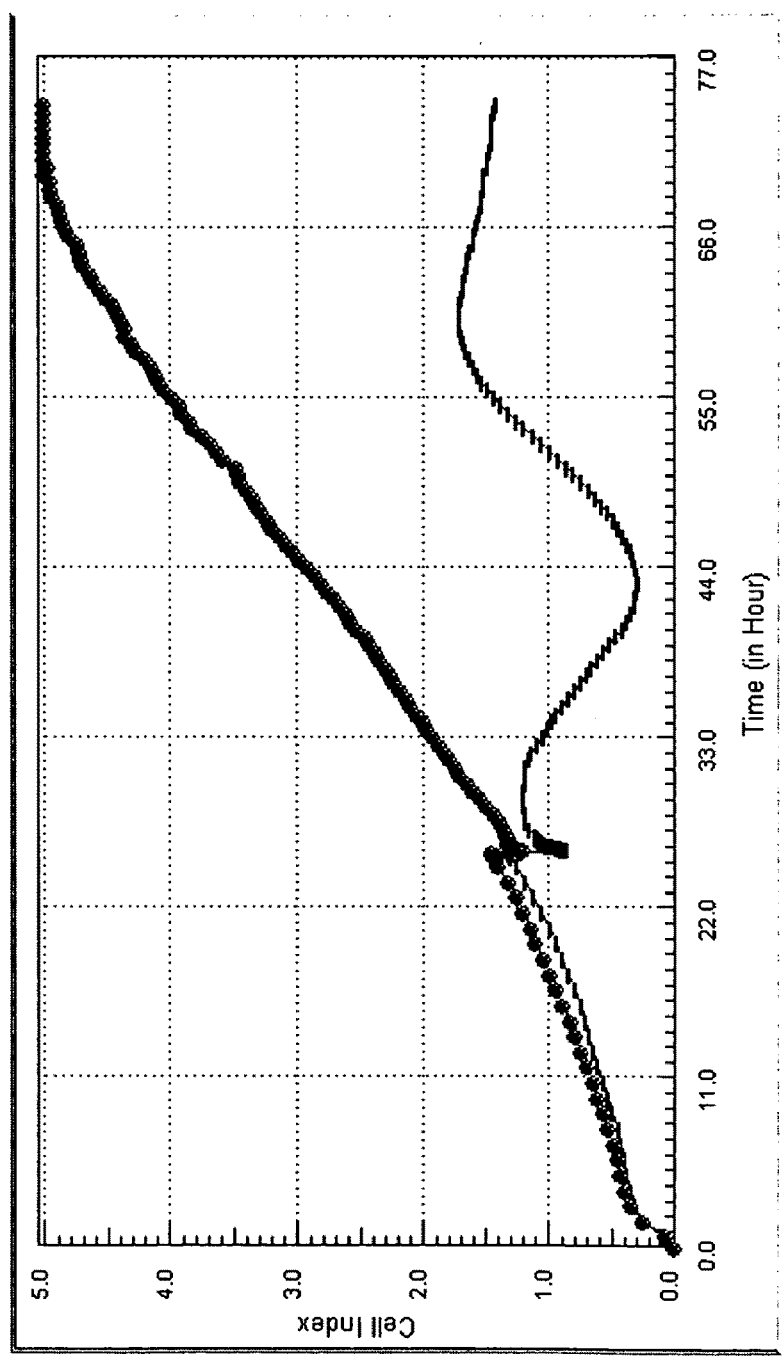
Figure 4B:
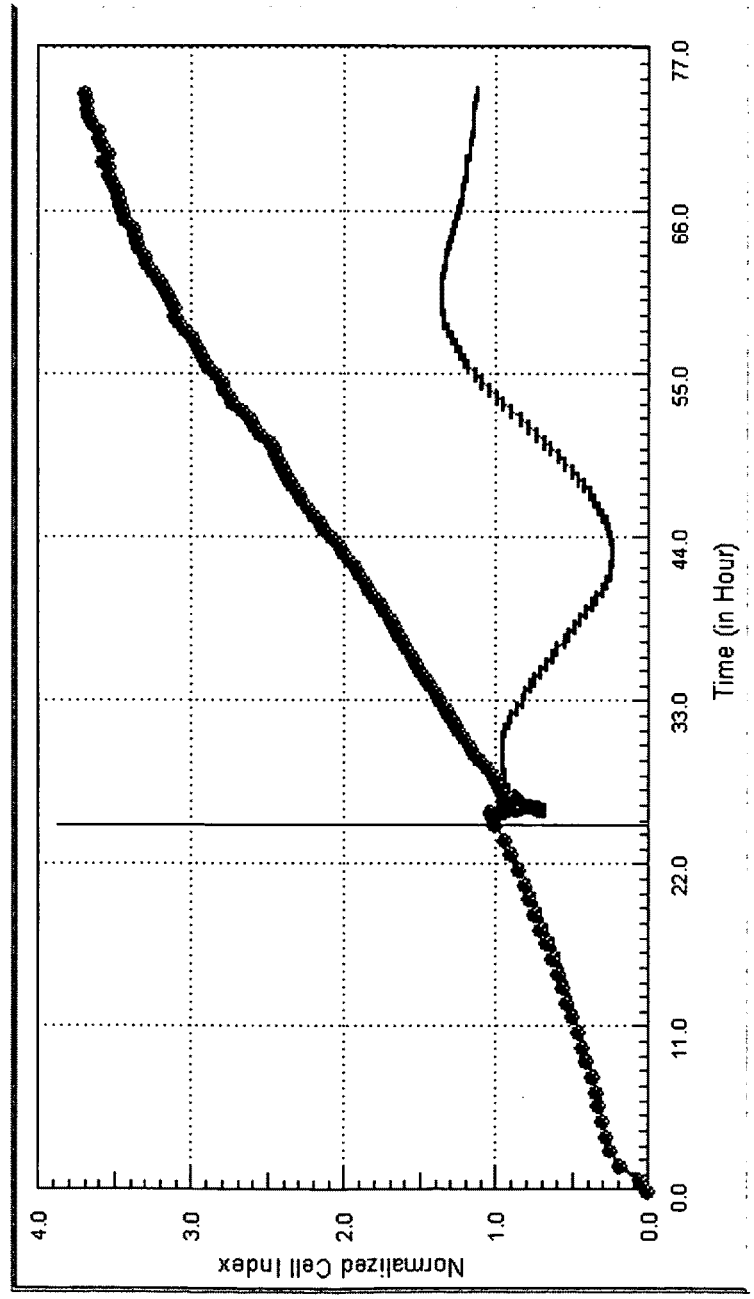
FIG. 4B is normalized and thus provides a more comparable and accurate distance between the curves. The normalized cell index curve in FIG. 4B is obtained by normalizing cell index curve in FIG. 4A at a reference time point of ~21 hr, i.e., dividing cell index value at any time point on FIG. 4A by the cell index value at the reference time point (~21 hr). The reference time point is typically the last time point of impedance measurement prior to treatment of cells with a biologically active agent.

In an exemplary embodiment, cell culture medium is first added to the wells of microtiter plate, which are integrated with the gold microelectrodes in each well (also referred to as an "E-Plate") to measure background or baseline impedance and calculate the Cell Index. The cells are then added to the wells of the E-Plate at pre-determined density and are continuously monitored to observe initial cell attachment and cell proliferation for any time period, for example, about 16-24 hours, prior to addition of biologically active agents to cells. The stage of cell attachment and growth prior to biologically active agent addition serves as cell type specific cell growth profile, which is informative for quality control purposes. This information can be used to assess cell health and ensure consistency between cells in different wells in the same E-Plate or across different E-Plates in different experiments. FIG. 2 shows a representative cell index curve obtained using the RT-CES system, where cells were treated with a biologically active agent at ~22 hour. Because cells have different morphological and adhesion characteristics, cells may have impedance-based curves. FIG. 3 shows the growth kinetic profile of 4 different mammalian cell lines with distinctive profiles. FIG. 4A demonstrates a comparison of curve alignment prior to normalization and FIG. 4B demonstrates a comparison after normalization. It has been found that normalizing curves to the last time point of impedance measurement prior to biologically active agent introduction allows for better comparison of cell index curves. Thus, at the last time pint of impedance measurement prior to biologically active agent introduction, normalized cell index values for all the wells is one, irrespective of exact number of cells in any wells. Any difference in changes in normalized cell index values after introduction of biologically active agents between different wells are associated only with differences in cells responding to the treatment of biologically active agents.

Introducing Biologically Active Agents

In preferred embodiments, impedance monitoring begins before the addition of a biologically active agent. Although nonlimiting, once the cells reach a predetermined or desired Cell Index, one or more biologically active agents are added to one or more wells and preferably a control is added to a second well. The time between cell seeding to introduction of biologically active agents may vary depending on the health of the cell(s), proliferation rate of the cells, lineage and the like. Typically about 16-24 hours for time between cell seeding to introduction of biologically active agents is sufficient, with increased or decreased times also within the scope of the present invention. After introduction of biologically active agents, the interaction between biologically active agents with cells cultivated on the microelectrodes may result in modulation of cell number, cell adhesion quality and cell morphology and therefore may result in changes in the Cell Index.

Biologically active agents are those that have a biological effect or suspected of having a biological effect on cells. Biological effects may be any known to those skilled in the cellular, biological or chemical arts. Biological effects include activation or inactivation of a cellular pathway, a cell signaling pathway, a stimulatory effect such as stimulating cell growth or cell to cell interaction, and the like. Non-limiting examples of biological effects include effects on cell viability, cell adhesion, apoptosis, cell differentiation, cell proliferation, cell morphology, cell cycle, IgE-mediated cell activation or stimulation, receptor-ligand binding, G-protein coupled receptor activation, receptor tyrosine kinase activation, cell number, cell quality, cell cycling, cell spreading. A biological effect may cause a change in cell size, shape, granularity, morphology and the like. A biological affect may induce, cause or enhance cell death. The biologically active agents may act on the cellular proteins, membrane associated molecules, RNA, DNA or the like. A biologically active agent may be a compound, a peptide, a protein, an antibody or antibody fragment, an apatmer, a ribozyme, a siRNA, a miRNA, a nucleotide, an anti-sense oligo, a virus, a bacteria, a yeast, a mammalian cell, a non-mammalian cell and a combination thereof. A biologically active agent may be a compound such as a DNA damaging agent, a protein tyrosine kinase inhibitor, a protein synthesis inhibitor, a nuclear receptor agonist and/or antagonist, a G-protein coupled receptor agonist and/or antagonist, a HDAC inhibitor, a proteasome inhibitor, a calcium pathway modulator, an anti-mitotic agent, a herbicide, a fungicide, an environmental toxicant, and an inhibitor or modulator of an enzyme or protein required for cell viability, cell adhesion, cell proliferation, apoptosis and cell morphology. Biologically active compounds may be added in combination or separate. Biologically active compounds may be added at a single concentration, at multiple concentrations, at serial dilutions and the like. In one example, multiple biologically active compounds having the same or similar mechanism may be added to an E-Plate. In another example, multiple biologically active compounds having different mechanisms may be added to an E-Plate at the same or different times. In yet another example, multiple known biologically active compounds having known mechanisms may be added to an E-Plate at the same or different times. In yet another example, multiple unknown biologically active compounds having unknown mechanisms may be added to an E-Plate at the same or different times. In yet another example, multiple unknown biologically active compounds with some having known mechanisms and some others having unknown mechanisms may be added to an E-Plate at the same or different times.

While the biologically active agent is introduced into the well, the cells are continuously monitored for changes in impedance or Cell Index and compared to untreated or control treated wells. The continuous monitoring of Cell Index changes over time in response to biologically active agents results in very specific cell response profiles, which is a manifestation of the mechanism of action of the biologically active agents within the cell. FIG. 5 shows the cell response profile of A549 cells treated with compounds with different mechanisms of action including anti-mitotic agents, DNA damaging agents, nuclear receptor modulators, protein synthesis inhibitors, histone deacetylase inhibitors, and calcium pathway modulators. Biologically active agents were added at variable concentrations. The cell response profile for a particular biologically active agent with a specific mechanism may vary from cell type to cell type. However, biologically active agents with similar mechanism will preferably display similar cell response profiles.

Due to the kinetic nature of the profiling approach both short term and long term biologically active agent activity can be monitored, allowing for detection of temporally isolated but distinct activities of small molecules and potentially off-target effects. These findings indicate that using impedance-based monitoring and profiling of cellular response upon exposure to biologically active compounds can provide incisive and quantitative information and novel mechanisms for existing drugs as well as experimental biological compounds. Short term refers to any short time period after introduction of biologically active agents to cells. Non-limiting examples of short term includes a time period of 3 hrs, 2 hrs, 1 hr, 30 minutes, 15 minutes, 10 minutes, 5 minutes after introduction of biologically active agents to cells. Short term period here would start at the moment of introduction of biologically active agents to cells and end within a short time range after that. Long term typically refers to a time period that is many hours after introduction of biologically active agents to cells. Long term period would start from several hours after and ends at many hours after introduction of biologically active agents to cells. Non-limiting long term period would start at 1 hr, 1.3 hr, 2 hr, 3 hr, 5 hr, 7 hr and end at 24 hr, 36 hr, 40 hr, 48 hr, 72 hr, or even longer after introduction of biologically active agents to cells. Here, both short term and long term are relative terms, and depending on different activities of biologically active agents, a short term in one experiment for one biologically active agent may be a long term in another experiment for another biologically active agent.

From the impedance measurements, an impedance-based curve may be generated or in the alternative a curve corresponding to cell index may be generated. Cell Index, being reflective of cell-electrode impedance is primarily dependent on three main factors; number of cells cultivated inside the wells, the inherent morphology of the cells and the adhesive interaction of the cells with the electrode array.

In the preferred embodiments, curves generated from wells treated with one or more biologically active agents are compared to curves generated from control wells, having no biologically active agent, but having media or a control vehicle or the like. Comparisons are preferably performed by analyzing curves that correspond to the impedance measurements or Cell Index, which is derived from impedance measurements or impedance-based curves and the difference is calculated, such as by algorithm. Furthermore, normalized cell index curves may be generated, which correspond to cell index curves normalized to the last time point of impedance measurement prior to adding a biologically active agent.

Impedance-based curves or Cell Index curves generated from wells having cells treated with a biologically active agent may initially be compared to those generated from control. If the difference between a curve generated from a treated and control well is insignificant, then the no mechanism specific cell response is deemed to have occurred in response to the biologically active agent. That is, if curves generated from wells treated with biologically active agents and control wells are sufficiently similar or have a sufficient degree of similarity, no mechanism specific response is deemed to have occurred. However, if the difference between curves generated from treated and control wells is significant over a short term or long term, a mechanism specific response is deemed to have occurred, the response and biologically active agent is categorized accordingly. That is if the impedance-based curves or Cell Index curves generated from treated and control wells are significantly different, a mechanism specific response is deemed to have occurred and the response may be categorized.

Figure 6B:
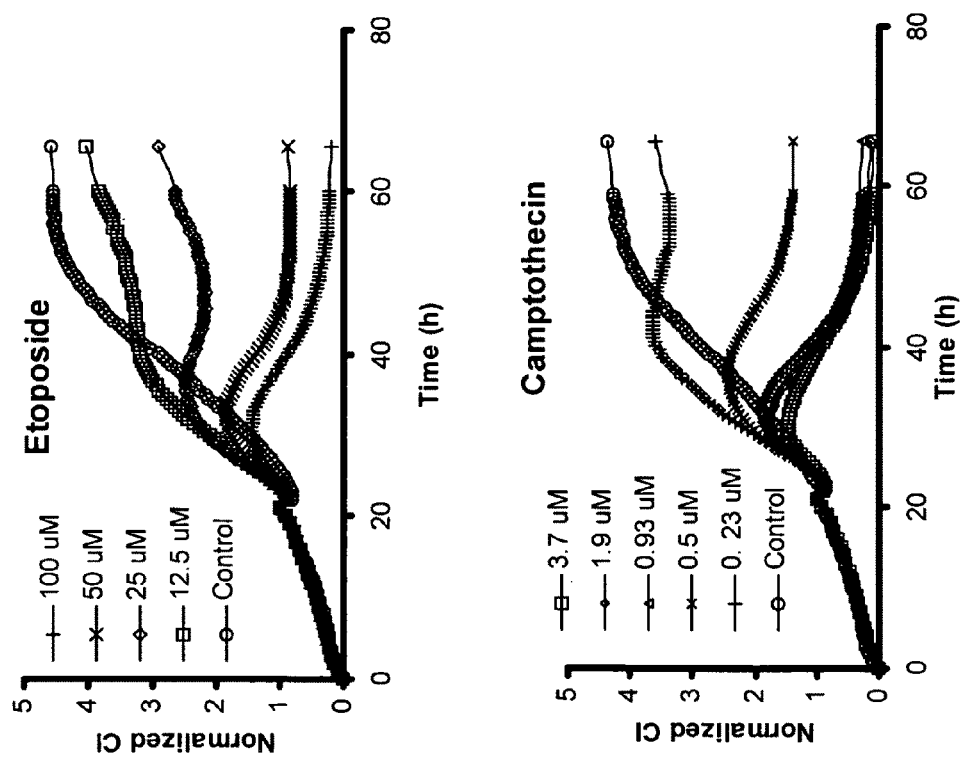
FIG. 6B is a graphical representation of cell response profiles of A549 cells treated with different topoisomerase inhibitors at varying concentrations.

The present systems demonstrate that biologically active agents with similar known mechanism display similar impedance-based cell response profiles. Thus, an impedance based cell response profile is predictive of mechanism of action of biologically active agents. In support, mammalian cells were cultivated in wells of the E-Plate and continuously monitored for 16 to 24 hours followed by treatment with biologically active agents with the same mechanism. The cells were continuously monitored for an additional 48-72 hours after treatment. The cell response profiles of the different biologically active (or bioactive) agents were compiled and compared. FIG. 6A shows the cell response profiles of A549 cells that have been treated with different anti-mitotic agents. Even though the compounds are structurally different, they have the same mechanism in that they induce mitotic arrest. Likewise the impedance-based cell response profiles for the compounds are very similar. FIG. 6B shows the cell response profiles for DNA damaging agents such as topoisomerase inhibitors, which are very similar.

Cell responses to biologically active agents are compared and categorized into mechanism specific cell response groups by generating cell impedance curves or cell-index curves for cells treated with the unknown biologically active agents, comparing the impedance-based curve or optionally cell-index curve to predetermined mechanism specific cellular response profile type and categorizing the impedance-based curves or optionally cell index curves into at two or more groups based on the similarities of the impedance-based curves or optionally cell-index curves.

Mechanism specific cellular response profile groups can be clustered or arranged such that groups having similarities are positioned nearest one another. Thus, like the grouping of curves, a cluster permits curves to be analyzed in close association. Clustering may assist in the determination of threshold or cutoff values to determine specific grouping.

Figure 7:
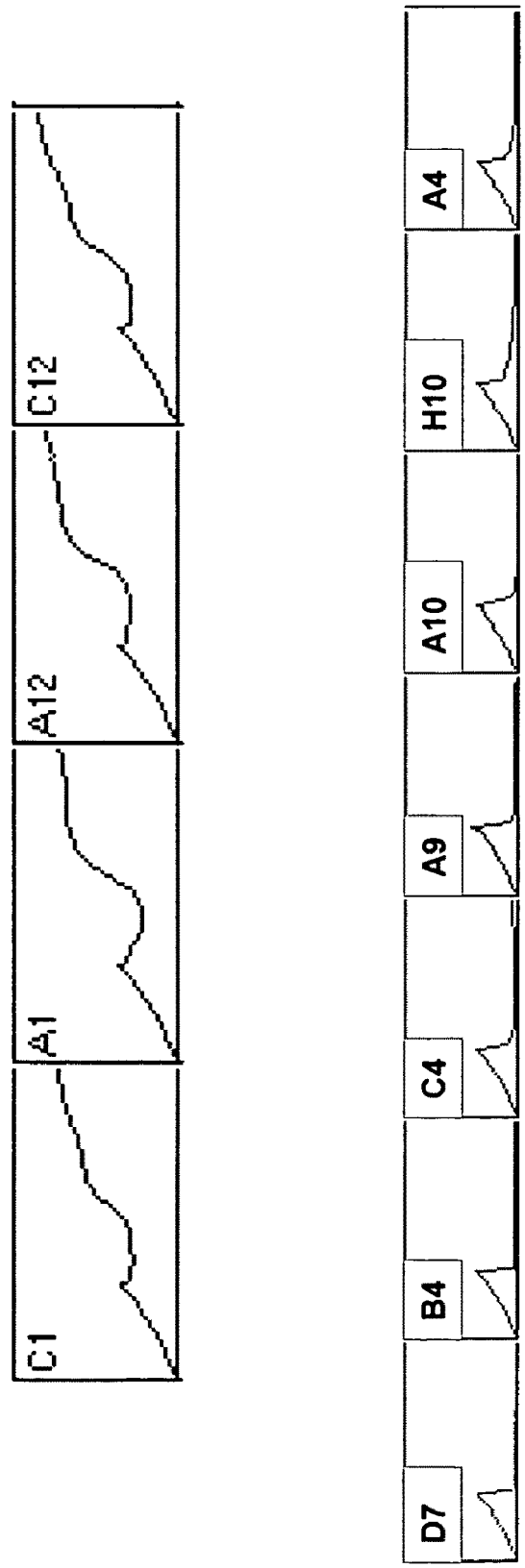
FIG. 7 is a graphical representation of categorizing cellular response profiles into mechanism specific groups. One group including cell index curves C1, A1, A12 and C12. A second group includes cell index curves D7, B4, C4, A9, A10, H10, A4.
Figure 8A:
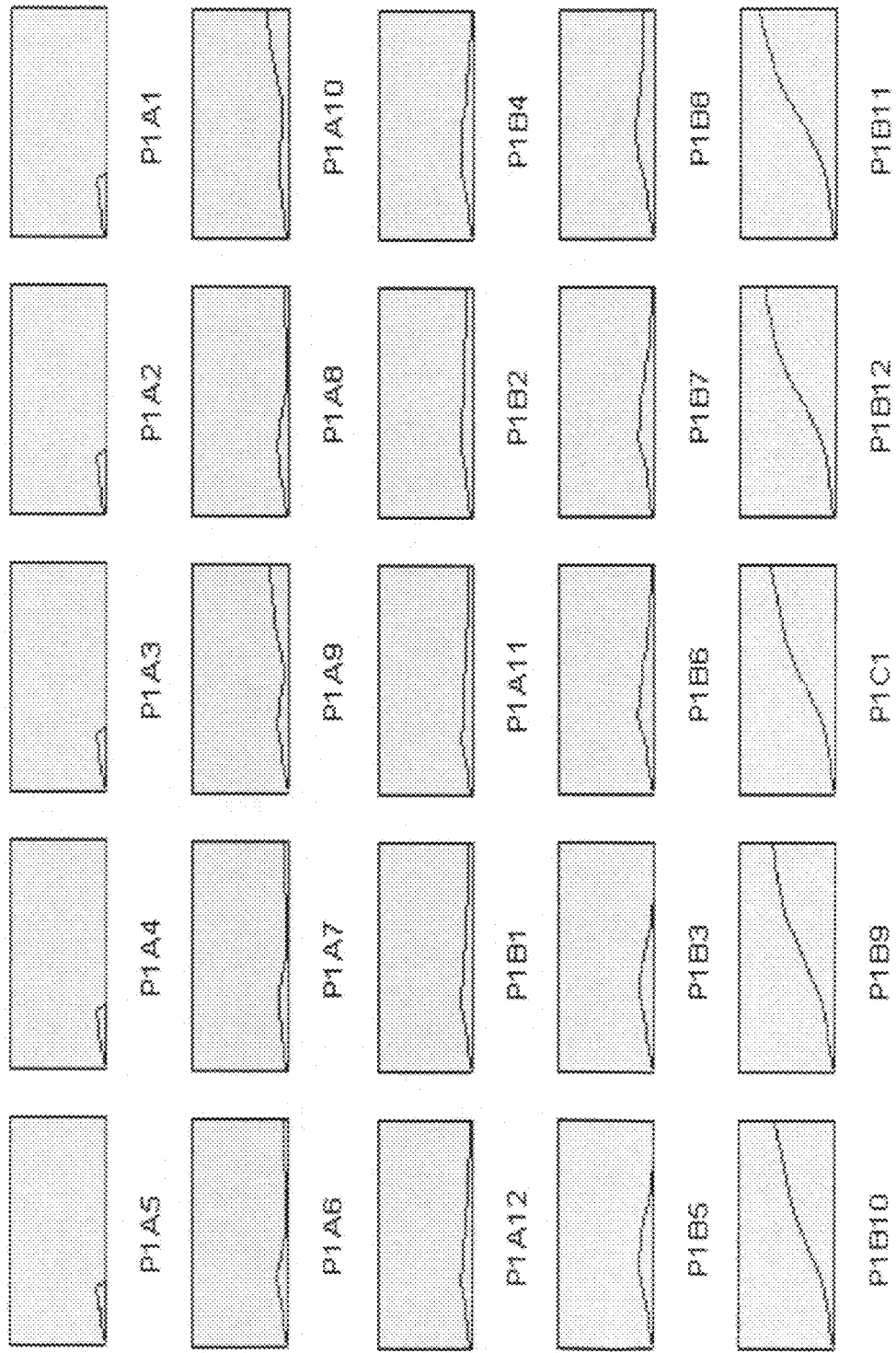
FIG. 8A depicts clustering of compounds with similar mechanism of action displayed as impedance-based kinetic profiles.
Figure 8B:
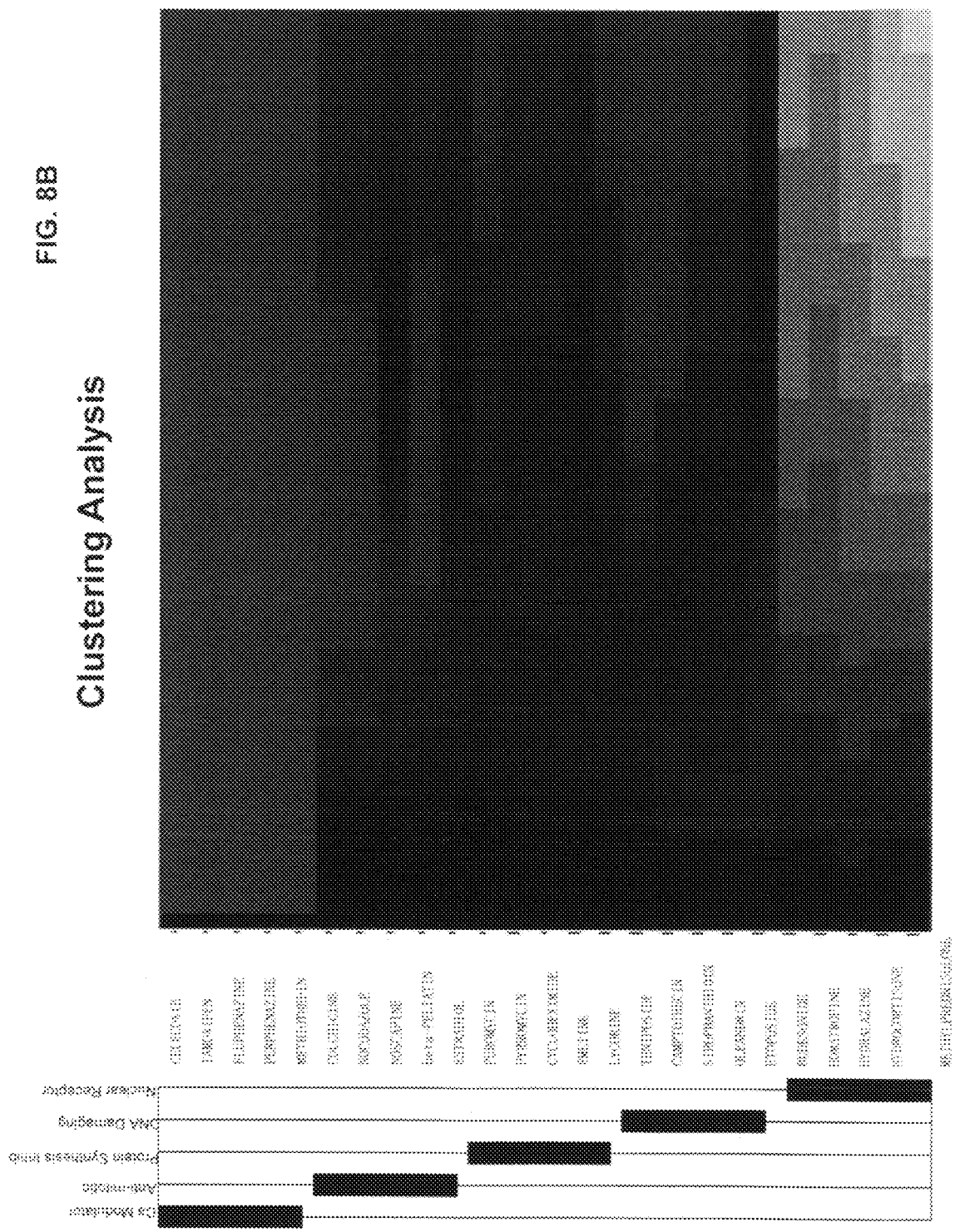
FIG. 8B depicts the clustering of cellular response profiles from biologically active agents with similar mechanism of action displayed as a heat map.

FIG. 7 depicts two groups of mechanism specific cellular response profiles categorized according to their similarities. In one embodiment, a clustering of impedance-based cell response profiles for compounds is used and in another embodiment, heat map is used to represent impedance-based cell response profiles, where different cell index values are represented by different colors in the map. FIG. 8A demonstrates a representative grouping of impedance-based cell response profiles for compounds with different mechanisms of action. FIG. 8B shows a heat map display of the same data.

The present invention provides many useful applications. Impedance-based cell response profiles can be used to assign mechanism to biologically active agents with previously unknown mechanism. In one representative embodiment of the invention, impedance-based cell response profiles are used to assign function or mechanism to biologically active agents with previously unknown mechanism. In such as case a library of biologically active agents with unknown mechanism can be screened against cells growing on E-Plates. The cell response profiles of the biologically active agents can then be compared to those of reference biologically active agents with known mechanism, based on the presence or absence of sufficient similarity. In another embodiment of the present invention, a library of biologically active agents with unknown mechanism can be screened against cells growing on E-Plates and the cell response profiles of the biologically active agents can be compiled, clustered (classified) to different groups, based on the presence or absence of sufficient similarity between all the response profiles.

Figure 9:
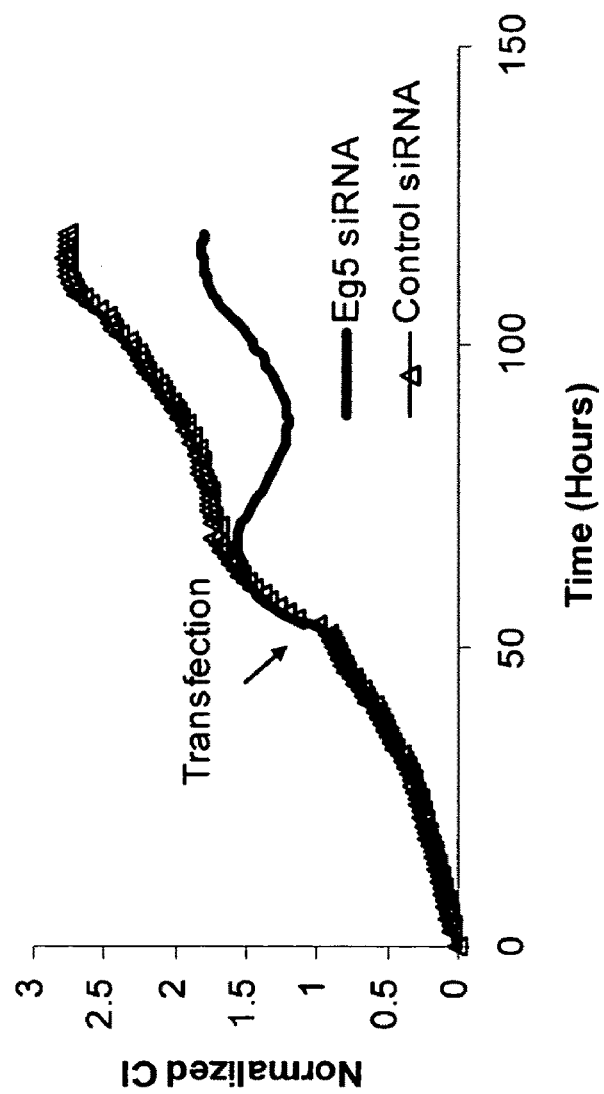
FIG. 9 is a graphical representation of a cell response profile obtained from A549 cells transfected with either a control siRNA or an siRNA targeting the mitotic kinesin Eg5 at approximately 50 hr. The profile is similar to cell response profiles obtained with anti-mitotic agents.

Impedance-based cell response profiles can also be used to assign mechanism or function to proteins with previously unknown mechanism. Proteins whose functions have remained elusive can potentially be assigned a specific mechanism or function using impedance-based cell response profiling approach. The method may include seeding mammalian cells, which express the protein target of interest, in the wells of the E-Plate. The cells can be continually monitored for a given length of time and then transfected with siRNA or any other biologically active agent that will selectively reduce or knock out the expression of the protein inside the cell. The cells can be continually monitored and an impedance-based cell response profile can be obtained. The cell response profile can then be compared against the group profile of other biologically active agents and if there is sufficient similarity, then it can be hypothesized that the absence of the protein with unknown function maybe involved in the same pathway or may have the same mechanism as that of a reference biologically active agent. FIG. 9 shows that the profile of A549 cells which were transfected either with a control siRNA or an siRNA specific for Eg5 kinesin motor protein. The profile obtained for knock-down of Eg5 matches that of compounds which induce mitotic arrest, indicating that Eg5 is involved in some aspect of mitosis. Indeed, Eg5 is a mitotic kinesin, which is involved in the orientation and separation of chrosmosomes during mitosis.

The activity of combinatorial libraries can be assessed using the described system. Compound libraries are typically a collection of diverse or focused compounds with uncharacterized activity. The cell response profiling approach described here can be used to characterize the different kinds of activities associated with a specific compound library and also cluster or group compounds that have similar cell response profiles. In this case any mammalian or non-mammalian cell line of interest can be seeded in E-Plates followed by screening and profiling of the compound library. The cell response profiles can then be analyzed by the curve classification and clustering software. The unique profiles obtained for the compounds can then be matched against a library of reference compounds with known mechanisms to assign potential mechanism of action for the compounds. In addition, the clustering or grouping function can be used to identify other compounds with similar activity profiles in the library. Alternatively, the kinetic profiling approach can also provide information regarding potential kinetically isolated and distinct mechanisms for the same compound.

The profiling approach for compound libraries can be a very powerful and time and resource saving approach in the drug discovery arena. Armed with very useful information about their compound libraries, the scientist in drug discovery arena could potentially only screen a subset of their compound library to look for specific kinds of activity and avoid compounds which have unrelated mechanisms or no activity at all. Furthermore, even though we have focused our discussion on compound libraries, this sort of an approach can also be applied to peptide libraries, protein libraries, antibody libraries, apatmer libraries, ribozyme libraries, siRNA, SHRNA, miRNA libraries and libraries of other potentially biologically active agents.

Similarly, a drug discovery company is potentially interested in anti-mitotic agents, then they can screen their compound library against a certain cell line of interest as discussed above and identify only those compounds that result in a cell response profile which is indicative of mitotic arrest. The advantage of this approach is that it readily affords a functional cell-based screen for anti-mitotic agents and at the same time only identifies those compounds that can cross the cell membrane bilayer and interact with the target inside the cell. The identified compounds can then be screened against targets of interest in target-specific biochemical assays. As mentioned above, other biologically active agents other than compounds can also be used.

Figure 10:
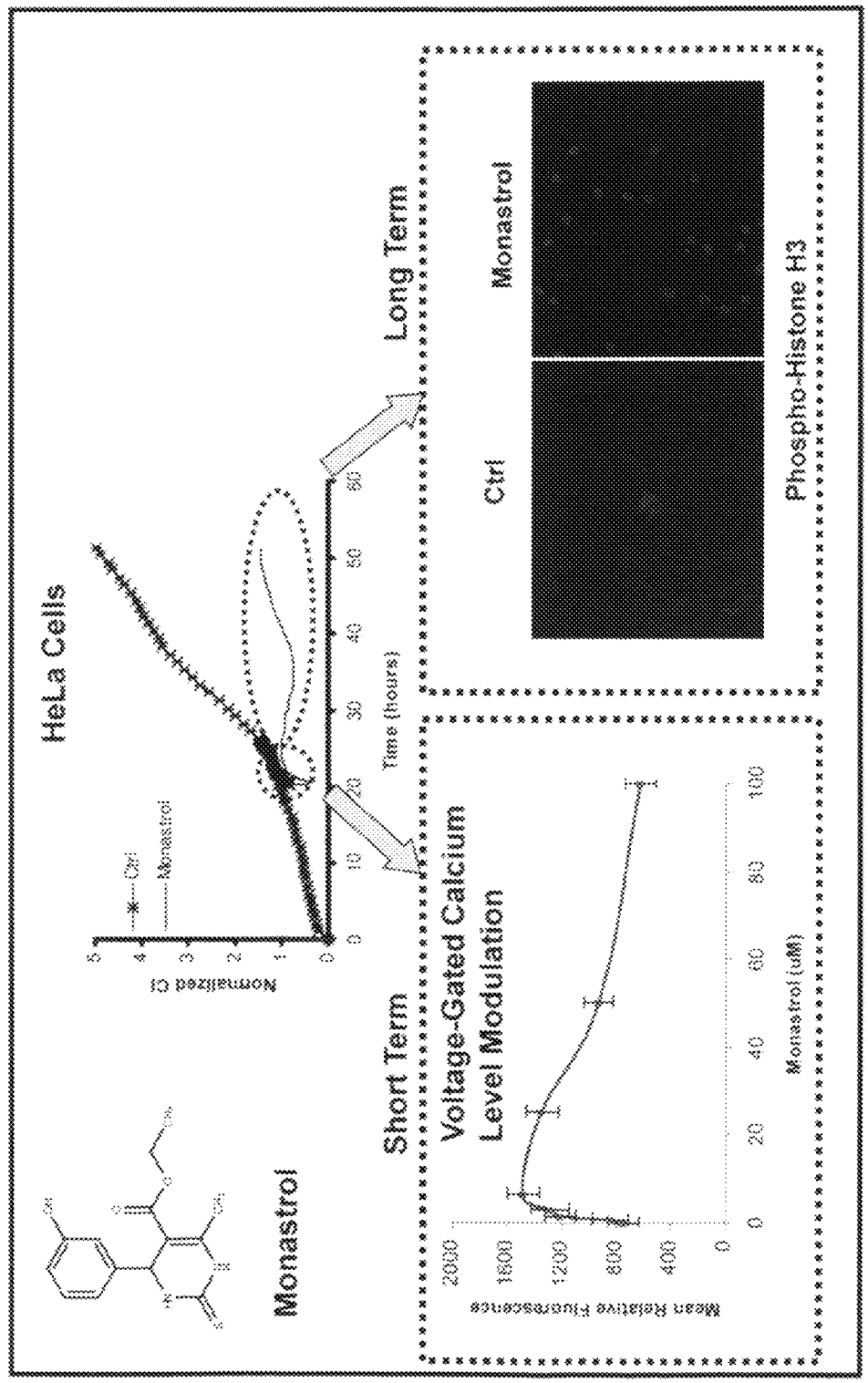
FIG. 10 demonstrates the cell response profile of Monastrol which displays two kinetically isolated and distinct profiles. The long term response profile (also referred to as the long term curve) is indicative of mitotic arrest, which is consistent with Monastrol being an anti-mitotic agent. The short term response profile (also referred to as the short term curve) is indicative of modulation of a calcium pathway. The lower panel demonstrates modulation of voltage-gated calcium channels measured by detection of mean relative fluorescence of a calcium dye in response to varying amounts of Manastrol. Phospho-Histone H3 staining is also depicted demonstrating staining of mitotically arrested cells which correlates with the long-term response.

In addition, identification of potential off-target effects may be identified. There are currently no effective approaches to identifying potential off-target effect of compounds in a systematic way. Off-target effects can potentially be toxic any may lead to attrition of the compound in animal studies or clinical trials. One of the key features of impedance-based cell response profile is that it is a kinetic based profile and therefore both short term and long term cell responses to compounds or biologically active reagents can be monitored and profiled. FIG. 10 shows the cell response profile of the compound Monastrol, which is an inhibitor of the mitotic motor kinesin. The cell response profile leads to two distinguishable kinetically isolated profiles. The long term response is indicative of anti-mitotic signature which is consistent with its biological function. However, the short term response is indicative a calcium pathway modulator, based on comparison to known reference compounds. Subsequent analysis by us has demonstrated that Monastrol can modulated voltage-gated calcium channel activity in an assay designed to assess calcium uptake through voltage-gated calcium channels. This attribute of impedance-based cell response profiling approach is very powerful and can potentially provide important information on off-target effects of compounds.

EXAMPLES

The following examples demonstrate various methods of comparing curves, their categorization and classification into groups.

Example 1

Comparing Curves

A variety of nonlimiting approaches may be used to identify similarities between curves and thus correlate biologically active agents to specific mechanisms. In one approach, the correlation coefficient between the two curves is used to define the similarity degree between the two curves. For example, give a curve one being $C_1(t_i); \{i=1, 2, 3, \ldots N\}$, and another curve being $C_2(t_i); \{i=1, 2, 3, \ldots N\}$, where curve one attains a value $C_1(t_i)$ at a time point $t_i$ and curve two has a value of $C_1(t_i)$ at the time point $t_i$.

The correlation coefficient between these two curves is calculated using this approach, $$CC(1,2) = \frac{N \sum_i [C_1(t_i)C_2(t_i)] - \sum_i C_1(t_i) \cdot \sum_i C_2(t_i)}{\sqrt{\left[N \sum_i [C_1(t_i)]^2 - \left(\sum_i C_1(t_i)\right)^2\right] \left[N \sum_i [C_2(t_i)]^2 - \left(\sum_i C_2(t_i)\right)^2\right]}}.$$

The larger the correlation coefficient, the more similar the two curves are. Since calculation of correlation coefficients is for comparing and categorizing cell responses to biologically active agents, thus, the time points used for calculation of correlation coefficients between curves are generally time points in a time period after cells being treated with biologically active agents or the control.

One could define a threshold for such "similarity". For example, a threshold value could be 0.9, meaning that if two curves having a correlation coefficient being more than 0.9, then these two curves are termed "similar".

In one embodiment of the present application, the methods of the invention are directed to categorize the cell response curves to unknown biologically active agents into one mechanism-specific cellular response profile group (out of multiple such profile groups). For each mechanism-specific cellular response profile group, assume that there is one corresponding response profile curve. First, let us assume that there are M-sets of such mechanism-specific response profile groups, each group being defined by a reference curve $RC_1(t_i); RC_2(t_i); \ldots RC_M(t_i), \{i=1, 2, 3, \ldots N\}$.

Then, with the cell response curves to one unknown biologically active agent being, $UC(t_i), \{i=1, 2, 3, \ldots N\}$, the goal is to categorize and classify this curve t into one of the response profile types by determining which response profiles has the largest correlation coefficient with the cell response curve of interest. The correlation coefficient between the k-th reference curve $C_k$ and the curve of interest is calculated using this approach, $$CC(k) = \frac{N \sum_i [RC_k(t_i)UC(t_i)] - \sum_i RC_k(t_i) \cdot \sum_i UC(t_i)}{\sqrt{\left[N \sum_i [UC(t_i)]^2 - \left(\sum_i UC(t_i)\right)^2\right] \left[N \sum_i [RC_k(t_i)]^2 - \left(\sum_i RC_k(t_i)\right)^2\right]}}$$

The cell response curve to the unknown biologically active agent is categorized into type $RC_n$ if n-th reference profile curve gives the largest correlation coefficient such that $$CC(n) = \max_{k=1,2,\ldots M} (CC(k)), \text{ and } CC(n) \text{ is larger than } 0.9.$$

If none of the correlation coefficients is more than 0.9, then the given response curve to the unknown biologically active agent is not classified as any one of the mechanism-specific response profile groups.

In another approach, a single characteristic parameter describing a cell response curve is determined and the differenced between two such parameters is used to define the degree of similarity between the two curves. In this approach, a single parameter having a positive value is derived for each curve by appropriate calculation formulas with the value for no-compound treatment (control) curves being set to 1. Then, for two given curves, the difference between parameters can be calculated. The smaller the absolute value of such difference, the more similar the two curves are.

One could define a threshold for such "similarity" if desired. Therefore similarity may vary depending on the user's needs or desires. For example, a threshold value could be 0.1, meaning that if two curves having a difference being less than 0.1, then these two curves are termed "similar".

As an example, the parameter is defined as the total area under the cell response curve for the monitored time period. Mathematically, for a given curve treated with a biologically-active agents and no-compound control curve, $$C(t_i), \{i=1, 2, 3, \ldots N\}$$

and $$C_{control}(t_i), \{i=1, 2, 3, \ldots N\}$$

the single parameter for the response curves to the biologically-active agents is defined as $$P = \frac{\sum_i [C(t_i) \cdot (t_i - t_{i-1})]}{\sum_i [C_{control}(t_i) \cdot (t_i - t_{i-1})]}.$$

Since calculation of single characteristic parameter is for comparing and categorizing cell responses to biologically active agents, thus, the time points used for calculation of single characteristic parameter for a curve are generally time points in a time period after cells being treated with biologically active agents or the control.

In one embodiment of the present application, the methods of the present invention categorize cell response curves from unknown biologically active agents into one mechanism-specific cellular response profile group (out of multiple such profile groups). For each mechanism-specific cellular response profile group, assume that there is one corresponding response profile curve. For example, first assume that there are M-sets of such mechanism-specific response profile groups, each group being defined by a reference curve $$RC_1(t_i); RC_2(t_i); \ldots RC_M(t_i), \{i=1, 2, 3, \ldots N\}.$$

The corresponding single parameter P for each curve is calculated using the formula above, being $P_1, P_2, \ldots, P_M$.

Then, with the cell response curve to one unknown biologically active agent being, $$UC(t_i), \{i=1, 2, 3, \ldots N\},$$

its corresponding single parameter P is calculated using the formula above, being $P_{UC}$.

The goal is to categorize and classify this curve into one of the response profile groups (or types) by determining which response profiles has the smallest difference in value from the curve of interest. The cell response curve to the unknown biologically active agents is categorized into group $RC_n$ if the absolute value of the difference between parameter $P_{UC}$ and parameter $P(n)$ such that $$P(n): \min_{k=1,2,\ldots M} |P(k) - P_{UC}|.$$

In another embodiment, the distance between two curves is determined to define the degree of similarity between two curves. There are various ways to define the distance between two curves, each of which may be used by the present invention and incorporated herein in their entirety. In one example, the distance is the sum of square of the difference of the two curves (dY) at a set of given time points.

Assuming a and b are two single curves, define the distance between curve a and curve b ($d_{a,b}$) as:

$$d_{ab} = \sum_{i=0}^{n} (Y_{ai} - Y_{bi})^2$$

Figure 11:
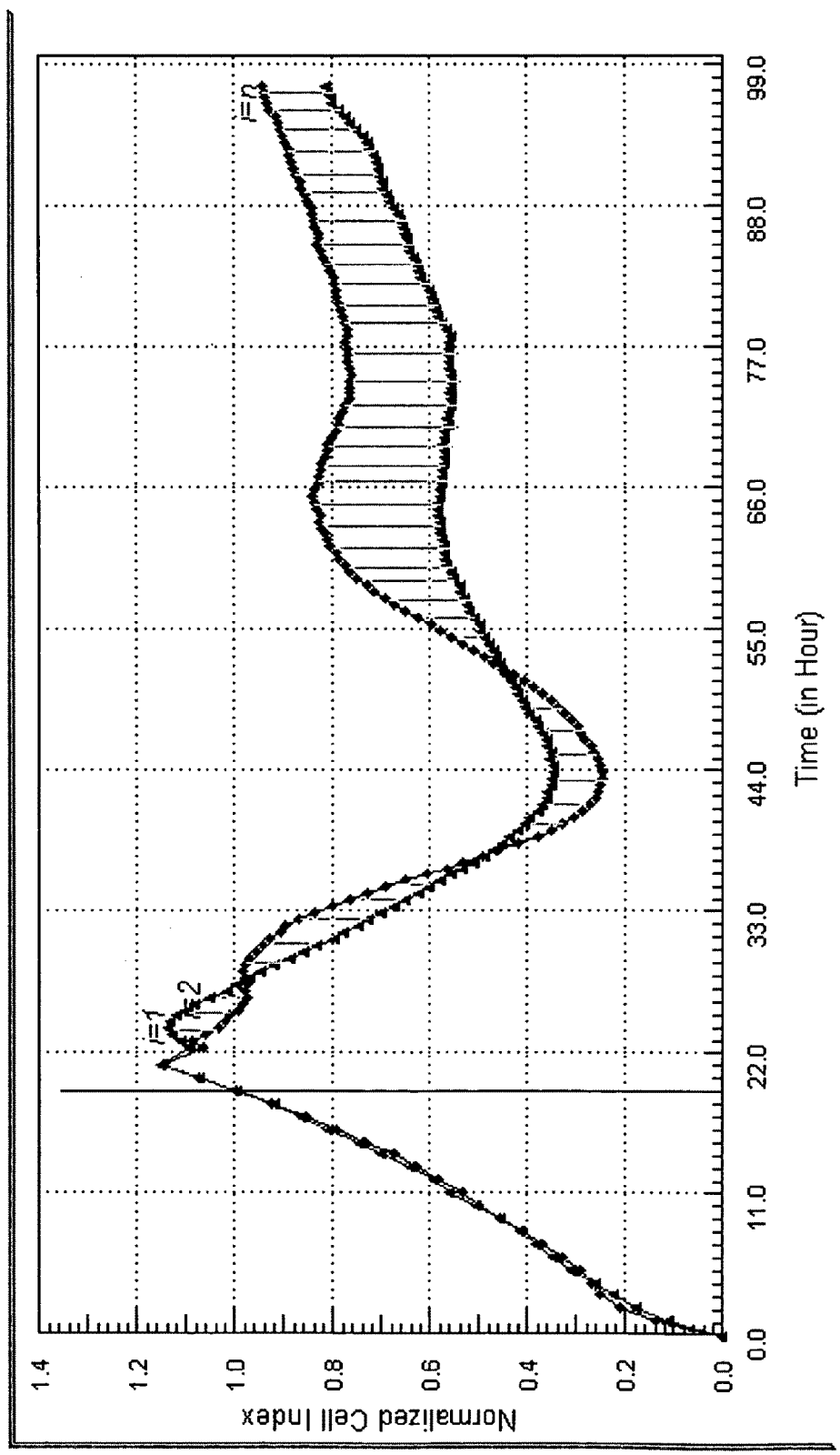
FIG. 11 is a graphical representation of two normalized cell index curves and the distance between curves for comparison. The time points i=1, i=2 and i=n are shown, which may be used for determining similarities between the curves.

Here, $Y_{ai}$ is the y value of curve a at ith-time point i, $Y_{bi}$ is the y value of curve b at ith time point. Since calculation of distance between curves is for comparing and categorizing cell responses to biologically active agents, thus, the time points used for calculation distance between curves are generally time points in a time period after cells being treated with biologically active agents or the control. The smaller the distance, the more similar the two curves are. FIG. 11 depicts a two curves having regions of close similarity and regions of difference.

In another embodiment of the present application, the methods of the present invention categorize the cell response curves to unknown biologically active agents into one mechanism-specific cellular response profile group (out of multiple such profile groups). For each mechanism-specific cellular response profile group, assume that there is one corresponding response profile curve. First, assume that there are M-sets of such mechanism-specific response profile groups, each group being defined by a reference curve $$RC_1(t_i); RC_2(t_i); \ldots RC_M(t_i), \{i=1, 2, 3, \ldots N\}.$$

Then, with the cell response curves to one unknown biologically active agent being, $$UC(t_i), \{i=1, 2, 3, \ldots N\},$$

The distance between this curve of interest and a reference curve can be calculated using the above formula and recorded as $d_{Rck,UC}$.

The goal is to categorize and classify this curve into one of the response profile groups by determining response profile from which mechanism-specific response profile group has the smallest distance in value from the curve of interest. The cell response curve to the unknown biologically active agents is categorized into type $RC_n$ if n-th reference profile curve has the smallest distance from curve of interest such that $$d(n) = \min_{k=1,2,\ldots M} \{d_{RCk,UC}\}.$$

Example 2

Determining the Distance Between a Curve and Curve Group

Assuming a is a single curve, B is a curve group which contains M curves, there are several ways to define the distance between a curve a and a curve group B. The curve group B contains M curves, being curve $b_1, b_2, b_3, \ldots b_M$. One distance between curve a and curve group B is the average distance, defined as follows:

$$d_{(ave)aB} = \frac{1}{M} \sum_{k=1}^{M} d_{ab_k}$$

Here $d_{ab_k}$ is defined as $d_{ab_k} = \sum_{i=1}^{n} (Y_{ai} - Y_{b_k i})^2$ Here, $Y_{ai}$ is the y value of curve a at ith-time point i, $Y_{b_ki}$ is the y value of curve $b_k$ at ith time point.

The minimum distance between curve a and curve group B may be determined by:

$$d_{(min)aB} = \min(d_{ab1}, d_{ab2}, \ldots, d_{abM})$$

The maximum distance between curve a and curve group B may be determined by:

$$d_{(max)aB} = \max(d_{ab1}, d_{ab2}, \ldots, d_{abM})$$

Example 3

Calculating Distances Between Two Curve Groups

In many cases the distance between two curve groups must be determined. Assuming A is a curve group with J curves: being curve $a_1, a_2, a_3, \ldots a_J$, B is another curve group with M curves being curve $b_1, b_2, b_3, \ldots b_M$, the distances between A and B are defined as follows:

The average distance between curve group A and curve group B can be calculated by:

$$d_{(ave)AB} = \frac{1}{JM} \sum_{l=1}^{J} \sum_{k=1}^{M} d_{a_l b_k}$$

The minimum distance between curve group A and curve group B may be the minimum distance between any curve pair, one of the pair from curve group A and another from curve group B, being determined by:

$$d_{(min)AB} = \min_{l=1:J; k=1:M}(d_{a_l b_k})$$

The maximum distance between A and B may be the maximum distance between any curve pair, one of the pair from curve group A and another from curve group B, being determined by:

$$d_{(min)AB} = \min_{l=1:J; k=1:M}(d_{a_l b_k})$$

Example 4

Curve Clustering

Using conventional curve clustering method (see, for example, Cluster analysis, Wikipedia, The free Encyclopedia, http://en.wikipedia.org/wiki/Cluster_analysis), we can classify and cluster N curves to different groups so that the curves in each group preferably share some common patterns. The curve clustering or curve classification is a process that involves continuous calculation of distances between curves, searching for minimum distances, and grouping curves within the given curve set. The group numbers can be from N (the number of curves in the given curve set) down to 1. When group number is N, each curve represents a separate group. Each group has one and only one curve. There are N curves so that there are N groups. When group Number is 1, all N curves are classified into a single group. This single group has N curves. When the group is N−1, then one group has two curves and each of the remaining (N−2) groups has one curve. The curve classification/clustering processes may be as follows:

1) Calculate the distances between every two groups (consider a single curve as a group)
2) Search for the closest two groups and cluster them together to form a new group
3) Repeat 1) and 2) until the desired group number or all curves are in one group Let us consider an example of n curves:

$$c_1, c_2, c_3, \ldots, c_i, \ldots, c_n)$$

The possible number of groups can be n to 1:

| Group number | Curves | |
|---|---|---|
| n | C1 C2 C3 ... Ci ... Cn − 1 Cn | Every curve is a separate group |
| n − 1 | C1 {C2-C3} ... Ci ... Cn − 1 Cn | The distance between C2 and C3 is the smallest among all distances between any two curves |
| n − 2 | {C1-C2-C3} ... Ci ... Cn − 1 Cn | The distance between C1 and group {C2-C3} is the smallest among all the distances between any two curve groups |
| ... | ... | ... |
| ... | ... | ... |
| ... | ... | ... |
| ... | ... | ... |
| ... | ... | ... |
| 1 | {C1-C2-C3- ... Ci ... Cn − 1-Cn} | All curves are clustered into one group |

Figure 17B:
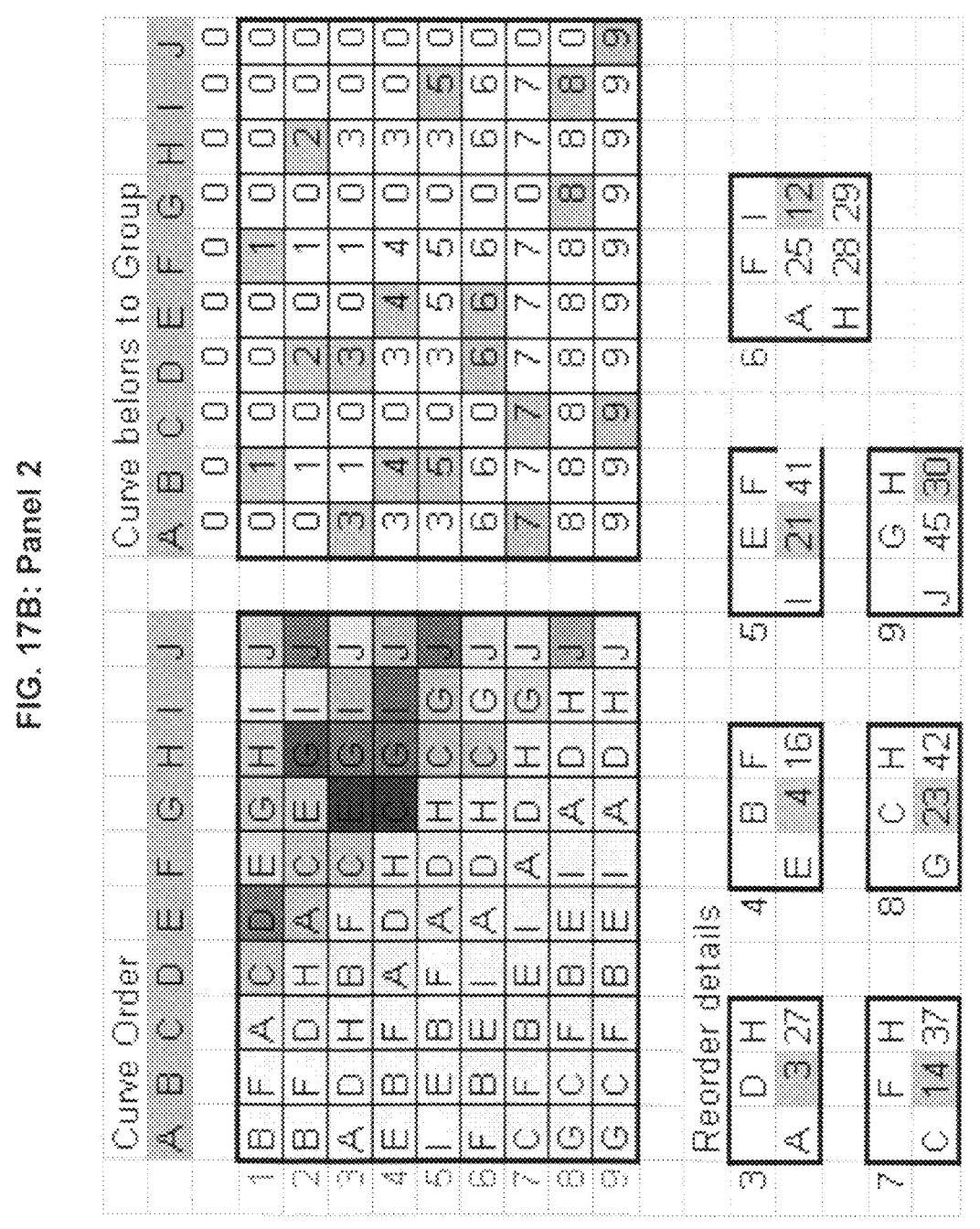

The conventional curve clustering involves in the calculation of the distance between curves, the distance from a curve to curve groups, and distance between a curve group and another curve groups. The distances have been described above. In FIG. 17, an example of curve clustering (curve classification) is shown with each curve being denoted as letter A, B, C, D, E, F, G, H, I and J. In this example, the "minimum distance definition" is used for calculating the distance between a curve and a curve-group.

To improve the curve clustering and classification method for addressing the curve classification of cell index curves from real experiments, we have taken the following approaches: (1) cell index curves are normalized at the last time point prior to introduction of biologically active agents; (2) the normalized cell index curves are projected to a common time coordinate. The curves from different experiments typically may have different impedance-measurement time points and cannot be directly compared. By projecting the normalized cell index curves onto a common time coordinate, the comparison between curves and the calculation of distance between curves from different experiments can be achieved; (3) searching for minimum distance between two curves by fixing one curve and moving another one horizontally and vertically within a small and given region.

Normalized Cell Index Curves. Cell index curves are normalized to the last impedance-measurement point, prior to introduction of biologically active agents to cells. Thus, at the last time pint of impedance measurement prior to biologically active agent introduction, normalized cell index values for all the wells is one, irrespective of exact number of cells in any wells. Any difference in changes in normalized cell index values after introduction of biologically active agents between different wells are associated only with differences in cells responding to the treatment of biologically active agents. Normalized cell index curves are used to calculate the distances between curves. FIG. 4A demonstrates a comparison of curve alignment prior to normalization and FIG. 4B demonstrates a comparison after normalization.

Figure 12B:
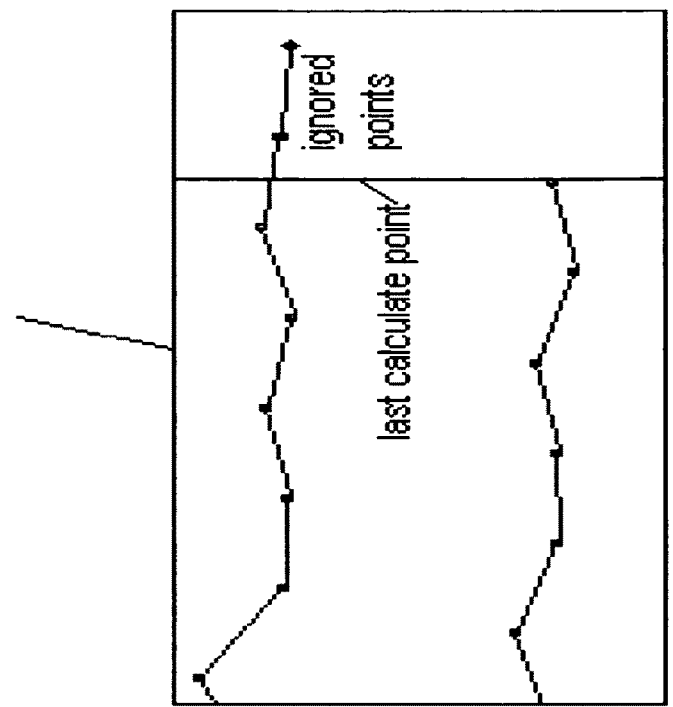
FIGS. 12A and 12B provide a graphical representation of curve points projected to a common coordinate for comparison.
Figure 12A:
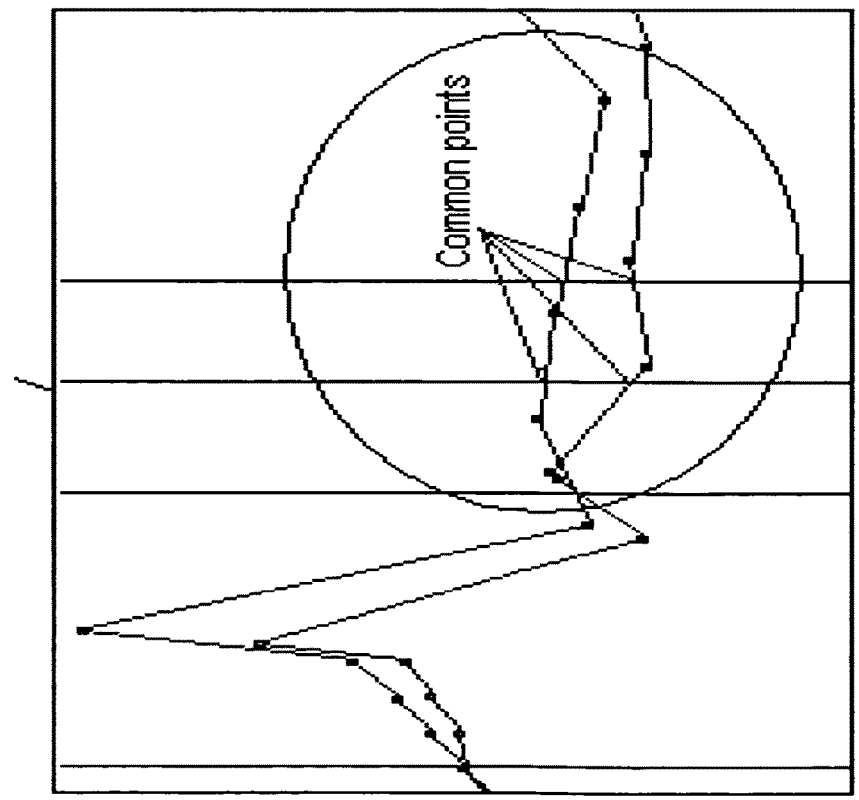

Projecting Curves' Points to a Common Time Coordinate. Referring to FIG. 12, in order to calculate the distance between two curves which may have different time points (for example, such curves may be obtained from different screening experiments), we set up a common time coordinate, which have a given time interval along the time coordinate (i.e., x-coordinate). The normalized cell index values at each given time point along the common time coordinate is "calculated or curve-fitted" based on the normalized cell index values from the original curves with the original time points. Furthermore, if two curves have different time ranges, then the calculation of distance will be based on the shorter time range of the two curves.

Searching Minimum Distance between Two Curves. In many cases, it was noted that the distance between two similar-looking curves is large. Detailed analysis of these cases revealed that the reasons for large distance are that somehow, these similar-looking experimental curves have "undesired" experimental variations in that. For example, two curves from two different wells in two separate experiments may be very similar in the curve shape, yet the time for such curve shapes may be slightly different or shifted because of unavoidable experimental variations. In this case, if we fix one curve and allow the other curve to shift a small time period along the time axis, then the distance between the two curves can be significantly smaller. Another example is shown in FIG. 13. FIG. 13 shows two curves cases: before and after shift. Obviously, the distance between these two curves become much smaller after one curve is shifted along time axis (X-axis) and normalized cell-index axis (Y-axis). Clearly, these two curves can be classified into one group because of the small distance between them.

Clustering Reordering: The conventional clustering is based on the process that at each "grouping" or "clustering" time, the number of groups is reduced by one. At each time, the algorithm searches for the smallest distance between either two curves (these curves do not belong to any group yet), or between one curve (this curve does not belong to any group yet) and one curve group, or between two curve groups among all the distances between any (no-group) curves, between any curve and any curve groups and between any curve groups. If the two curves have the smallest distance, then the two curves are clustered into one new group. If one curve has the smallest distance to a curve group, then this curve is clustered into the curve group to form a new curve group. Furthermore, if two curve groups have the smallest distance, then these two curve groups are clustered together to become a new group. Such process is repeated until at the end, all the curves are clustered into a single curve group.

To judge which curve(s) or group(s) is to be clustered or grouped, there are many methods to calculate distances between curves, between curve groups, between curves and curve groups. Examples of commonly used distances are:
  Minimum distance
  Minimum of average distances
  Minimum of maximum distances With conventional clustering, when a curve and a curves group, or two curve groups, are clustered together, their relevant order when positioned along an one-dimensional line is not considered.

Referring to FIG. 14, assume that there are 4 curves: a, b, c, and d and the distances between them satisfy the following: ab<bc<bd<ad<cd. Thus, first, a and b are clustered together (because of their smallest distance ab) to form a curve group—ab. There are three groups after the first clustering: group one: {a-b}, group two: {c} and group three: {d}. Secondly, c is clustered into the group {a-b} (because of the smallest distance bc) to form a new group {a-b-c}. Thus there are two groups left: group one {abc} and group two {d}. Thirdly, d is clustered into the group {a-b-c} to form the last, single group {a-b-c-d}. When the clustering goes to this last layer (d is being clustered), with conventional clustering method, d could be next to c when shown along the one-dimension on the bottom-left of FIG. 14. If after clustering and the curves a, b, c and d are arranged along the single dimension like those shown on the bottom-left of FIG. 14, we note that curve c and curve d are located next to each other, despite of their largest distance (note the above assumption for distances: ab<bc<bd<ad<cd).

Thus, with cluster reordering, when a curve is added to a group or when two groups are clustered together, where and how to chain them (or arrange them along a single dimension for representation) is very important. Using the rules described below, the curves can be chained or arranged to a single dimensional line with the feature that the curves having smaller distances are located closer to each other than the curves having larger distance. Referring back to the cases in FIG. 14, when curve d is being clustered to the previously clustered group {a-b-c}, its distances to the group's left end {a} and right end {c} are considered. In this case, since distance ad is smaller than the distance cd, the reordered cluster shall be: {d-a-b-c}. (see FIG. 14 bottom-right). Note that although distance bd is smaller than distance ad, curve d should not be inserted to neither b left (because ab<ad), nor b right (because bc<bd).

The Cluster Reordering Rules: The following rules may be used for the cluster reordering:

a) The orientation of a group does not a matter, i.e. its most-left element (curve) and most-right element (curve) are exchangeable. For example, if a group contains 3 curves: a, b, and c, and it has been clustered as {a-b-c}, (here a is the most-left element/curve, and c is the most-right element/curve), then {c-b-a} (c is the most-left element/curve, and a is the most-right element/curve) equals to {a-b-c}.

b) Once a group is formed, the relevant positions of elements/curves within the group cannot be changed. For example, if {a-b-c} is formed as group, the group cannot be changed to either {a-c-b} or {b-c-a}.

c) When two single curves are clustered to a new group, their order does not a matter. For example, if curve a and curve b is forming a group, {a-b} and {b-a} are the same new group.

d) When a single curve is being clustered to a group, the single curve should be chained or arranged into the group to become either the most-left element/curve or the most-right element/curve, depending whether the distance between this single curve and the original most-left element is smaller than the distance between the single curve and the original most-right element. For example, a curve {d} is being clustered to a curve group {egfc}. If distance de is smaller than distance dc, then the new group should be {degfc}. If distance dc is smaller than the distance de, then the new group should be {egfcd}.

When two curve groups are being clustered to a new group, they should be chained or arranged into a new group as illustrated below. Assume two curve groups: {cfga} and {kdbe}. If distance ck is the smallest among distances ck, ce, ak and ae, then the new cluster should be {ebdkcfga}. If distance ce is the smallest among distances ck, ce, ak and ae, then the new cluster should {kdbecfga}. If distance ak is the smallest among ck, ce, ak and ae, then the new cluster should {cfgakdbe}. If distance ae is the smallest among ck, ce, ak and ae, then the new cluster should {cfgaebdk}.

The following parts describe the rules in details.

Two Single Curves Are Clustered to a New Group: Suppose that both curve a and curve b are single curves. Their distance at current clustering step is the smallest, then they should form a new group. When curve a and curve b are clustered to the new group, their order does not a matter, i.e. the new group could be {a-b}, or {b-a}.

Figure 15:
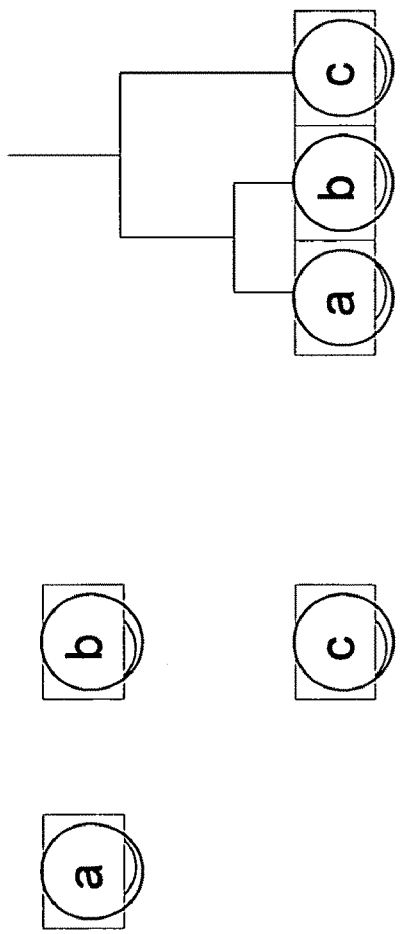
FIG. 15 is a character representation of adding a single curve to a group.

A Single Curve Is Added to a Group: In the following example as shown in FIG. 15, assume that the distances between any two curves are: ab<bc<ca. The clustering process is:
 a) Curve a and curve b grouped first to form a first group {a-b}.
 b) Curve c is going to be added to the group {a-b} to form a new group.
 c) Since distance bc<distance ac, then the new group should be {a-b-c}, not {c-a-b}.

Figure 16:
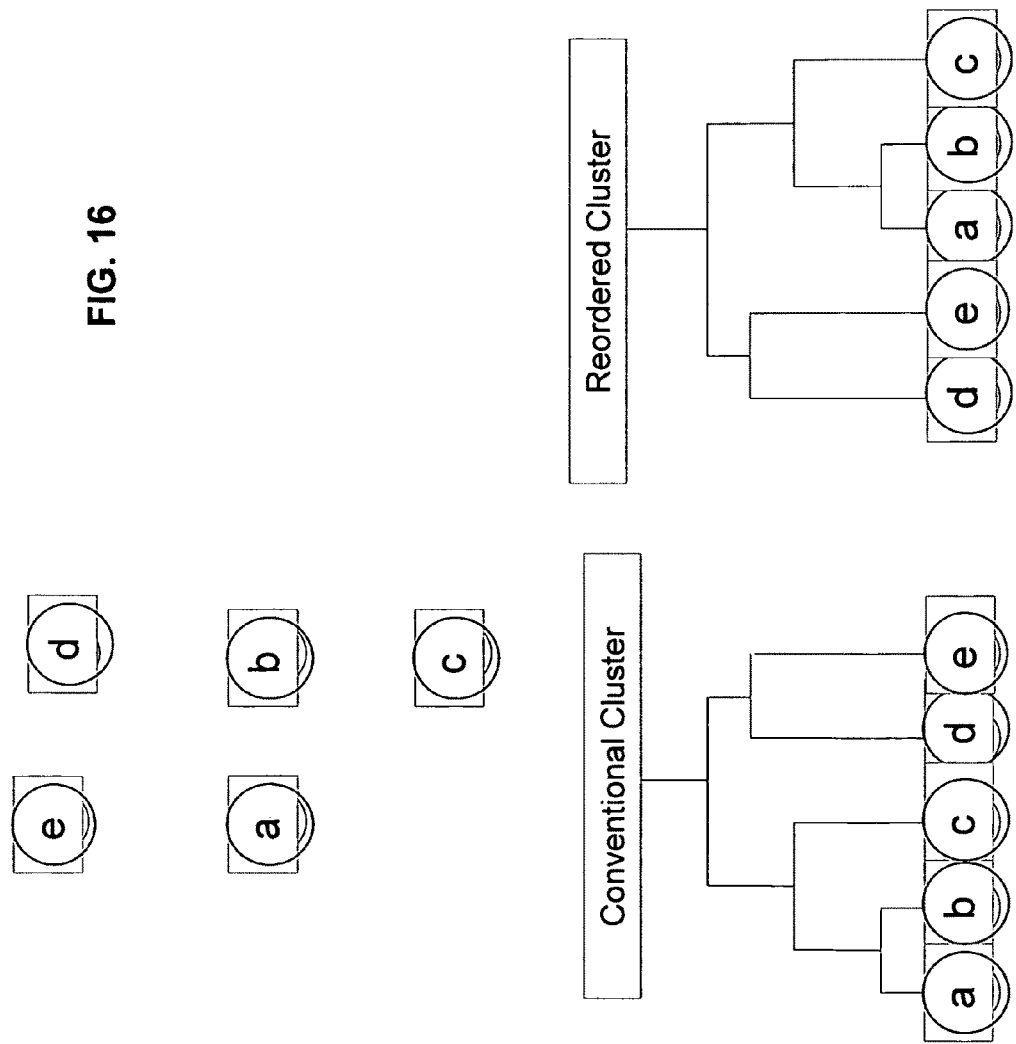
FIG. 16 depicts two groups being clustered into a new group.

Two Groups Are Clustered to a New Group. Assume that there are 5 curves: a, b, c, d, and e, and their distances between any two curves satisfy the following: ab<bc<de<bd<ae<be<cd<ce<ac<ad. The clustering process is shown on FIG. 16.

Initial condition having five (5) groups: {a}, {b}, {c}, {d} and {e};

First grouping/clustering having four (4) groups: {a-b}, {c}, {d}, {e};

Second grouping/clustering having three (3) groups: {a-b-c}, {d}, {e};

Third grouping/clustering having two (2) groups: {a-b-c}, {d-e};

Fourth-grouping/clustering having one (1) group: {e-d-a-b-c}.

A 10-Curves Clustering and Reordering Example:

Referring to FIG. 17, 10 curves (A, B, C, D, E, F, G, H, I and J) are clustered and reordered as an example to illustrate all the reordering rules described above. In this example, "minimum distance" is used to calculate the distance between a curve and a curve group, or between two curve groups. Initially, we have ten curve groups, each having one curve:

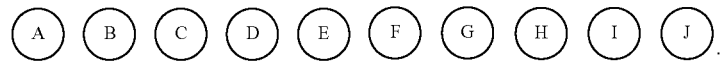

Cluster 1:
{B} and {F} have the smallest distance among distances between any two curves ($d_{bf}=1$), they are clustered. There are now nine groups.

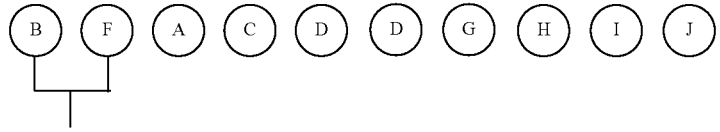

Cluster 2:
{D} and {H} have the smallest distance among distances between any two curve groups ($d_{dh}=2$). {D} and {H} are clustered. There are eight groups.

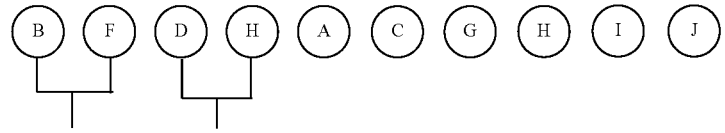

Cluster 3:
{A} and {D-H} have the smallest distance among distances between any two curve groups. ($d_{ad}=3$), so that {A} is added to {D-H} group. There are now seven groups.
Since ($d_{ad}=3$)<($d_{ah}=27$), the new group order is {A-D-H}.

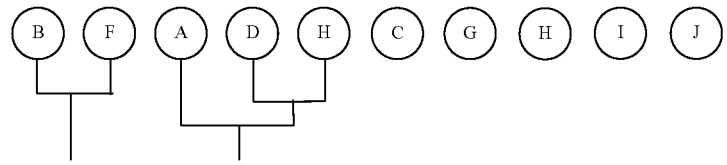

Cluster 4:
{E} and {B-F} have the smallest distance among distances between any two curve groups ($d_{be}=4$), so that {E} is added to {B-F} group. There are now six groups.

Since ($d_{be}=4$)<($d_{ef}=16$), the new group order is {E-B-F}.

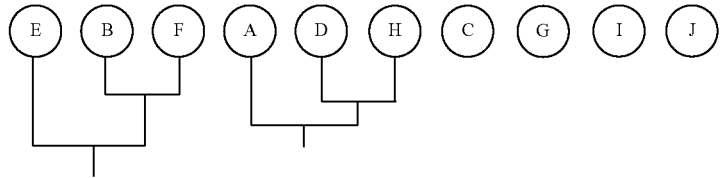

Cluster 5:
{I} and {E-B-F} have the smallest distance among distances between any two curve groups ($d_{ib}=5$) so that {I} is added to {E-B-F} group. There are now five groups.

Since ($d_{ie}=21$)<($d_{if}=41$), the new group order is {I-E-B-F}.

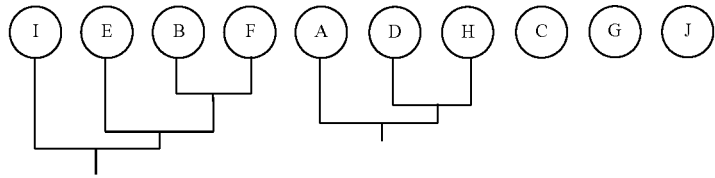

Cluster 6:
{I-E-B-F} and {A-D-H} have the smallest distance among distances between any two curve groups ($d_{ai}=12$) so that {I-E-B-F} is added to {A-D-H} group. There are now four groups.

Since ($d_{ai}=12$)<($d_{af}=25$)<($d_{fh}=28$)<($d_{hi}=29$), the group order is {F-B-E-I-A-D-H}. Note: in order to attach I to A, group {I-E-B-F} is reversed to {F-B-E-I}.

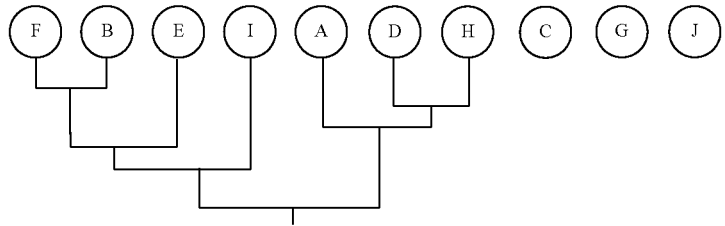

Cluster 7:
{C} and {F-B-E-I-A-D-H} have the smallest distance among distances between any two curve groups ($d_{cf}=14$) so that {C} is added to {F-B-E-I-A-D-H} group. There are now three groups.

Since ($d_{cf}=14$)<($d_{ch}=37$), the group order is {C-F-B-E-I-A-D-H}.

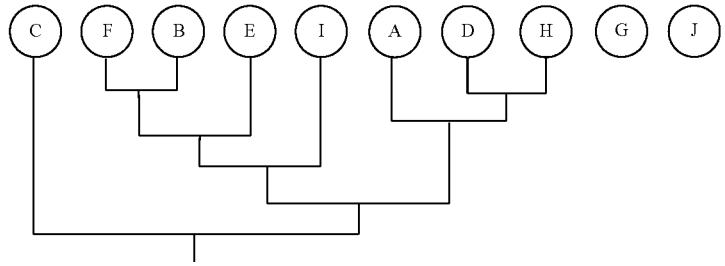

Cluster 8:

{G} and {C-F-B-E-I-A-D-H} have the smallest distance among distances between any two curve groups ($d_{cg}$=23) so that {G} is added to {C-F-B-E-I-A-D-H} group. There are now two groups.

Since ($d_{cg}$=23)<($d_{hg}$=42), the group order is {G-C-F-B-E-I-A-D-H}.

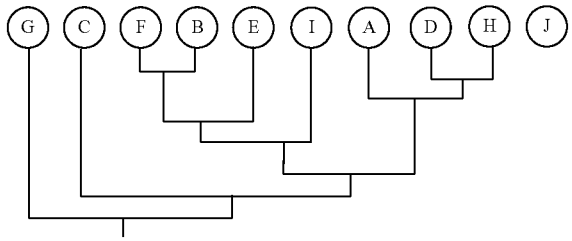

Cluster 9:

{J} and {G-C-F-B-E-I-A-D-H} are the last two groups. Now they are clustered together to form one group. (the end of the clustering)

Since ($d_{jh}$=30)<($d_{gj}$=45), the group order is {G-C-F-B-E-I-A-D-H-J}.

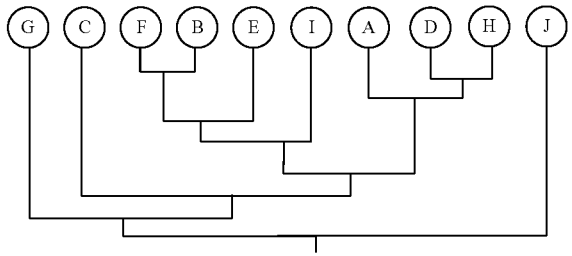

Example 5

Demonstration of Curve Classification and Reordering

Figure 18A:
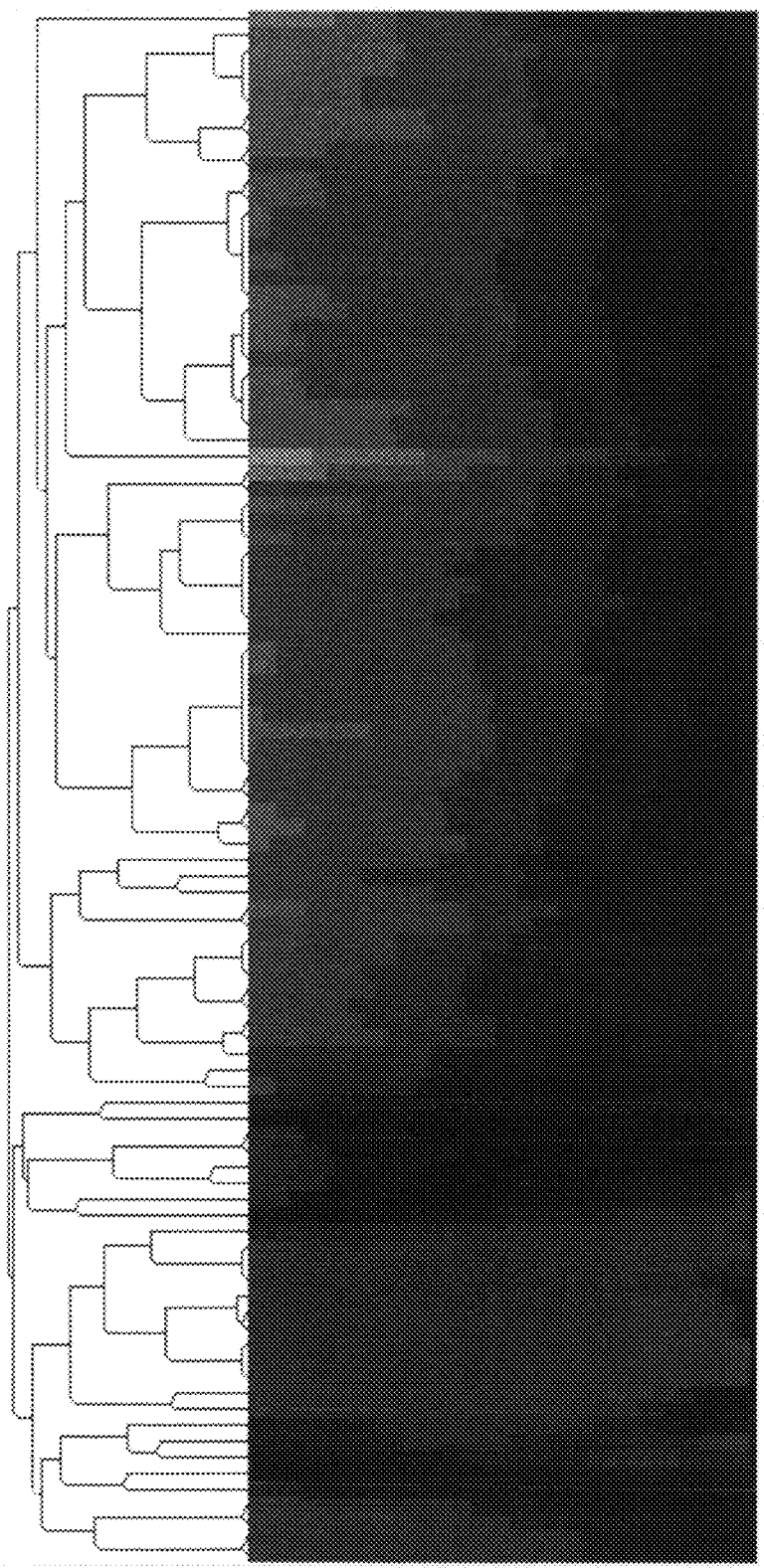
FIG. 18A is a heat map depicting the classification and grouping of 96-curves obtained from a 96 well microplate experiment.
Figure 18B:
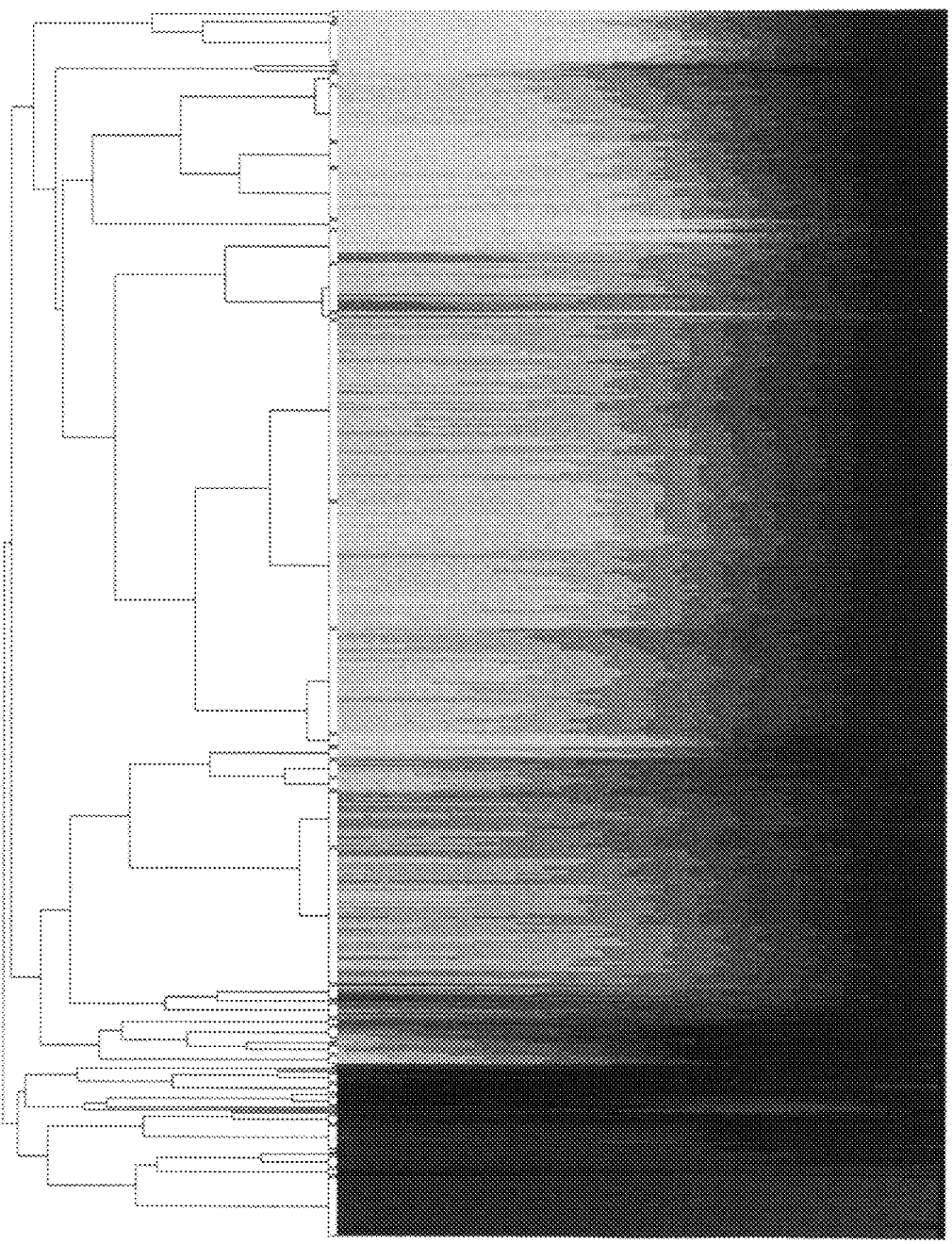
FIG. 18B is a heat map depicting the classification and grouping of 480-curves obtained from a five 96-well microplate experiment. In both FIG. 18A and FIG. 18B, for simplicity, the heat maps are shown for the curves being classified into between 50-groups and one group.

This example demonstrates curve classification and reordering. The original cell index curve data is obtained by using ACEA RT-CES system. They are from different microplates and from different screening experiments. FIG. 18A is a heat map depicting the classification and grouping of 96-curves obtained from a 96 well microplate experiment. FIG. 18B is a heat map depicting the classification and grouping of 480-curves obtained from a five 96-well microplate experiment. In both FIG. 18A and FIG. 18B, for simplicity, the heat maps are shown for the curves being classified into between 50-groups and one group.

FIG. 19 depicts the results of curve classification and categorizing of 480-curves from a five 96-well microplate experiment. In this case, there are initially five 96-well microplates. The arrangement of 480-curves in the five 96-curve graphs is based on classification and reordering results of these curves so that the classified curves, when arranged along an one-dimension, have this feature that curves with smaller distances are located near to each other.

What is claimed is:

1. A method of categorizing a cell response to a biologically active agent into mechanism-specific response profile group, comprising:
   a. providing a device for measuring cell-substrate impedance, wherein said device comprises at least two wells, further wherein said device is operably connected to an impedance analyzer;
   b. adding cells to said at least two wells;
   c. monitoring impedance of said at least two wells at time intervals over a time period and optionally determining cell indices from impedance values;
   d. introducing at least one biologically active agent to at least one and a control to another of said at least two cells, wherein said introduction occurs during said time period such that at least one of said impedance values is obtained prior to said introduction;
   e. generating an impedance-based curve or optionally a cell index curve for each of said at least one biologically active agent and said control;
   f. comparing said impedance-based curves or optionally said cell index curves between said at least one biologically active agent wells and said control well; and if significantly different
   g. categorizing said impedance-based curve or optionally said cell index curve of said at least one biologically active agent to a group, wherein said group defines a mechanism-specific cellular response profile corresponding to said at least one biologically active agent.

2. The method according to claim 1, wherein said device comprises:
   a. a nonconductive substrate; and
   b. a conductive electrode array fabricated on said nonconductive substrate;
   wherein said cell is capable of attaching to said electrode array.

3. The method according to claim 2, wherein said device is in the format of a multi-well plate; wherein each well comprises said conductive electrode array.

4. The method according to claim 3, wherein said multi-well plate is selected from the group consisting of a 16 well plate, a 24 well plate, a 96 well plate, a 384 well plate, and a 1536 well plate.

5. The method according to claim 1, wherein said biologically active agent is selected from the group consisting of a compound, a peptide, a protein, an antibody or antibody fragment, an apatmer, a ribozyme, a siRNA, a miRNA, a nucleotide, an anti-sense oligo, a virus, a bacteria, a yeast, a mammalian cell, a non-mammalian cell, and a combination thereof.

6. The method according to claim 1, wherein said cell is selected from the group consisting of a primary cell, a cell line, and an engineered cell expressing a specific protein or sets of proteins.

7. The method according to claim 5, wherein said compound is selected from the group consisting of a DNA damaging agent, a protein tyrosine kinase inhibitor, a protein synthesis inhibitor, a nuclear receptor agonist and/or antagonist, a HDAC inhibitor, a proteasome inhibitor, a calcium pathway modulator, an anti-mitotic agent, a herbicide, a fungicide, an environmental toxicant, and an inhibitor or modulator of an enzyme or protein required for at least one selected from the group consisting of cell viability, cell adhesion, cell proliferation, apoptosis, and cell morphology.

8. The method according to claim 1, wherein categorizing said impedance-based curve or optionally said cell index curve is based on short term curves.

9. The method according to claim 1, wherein categorizing said impedance-based curve or optionally cell index curve is based on long term curves.

10. The method according to claim 1, wherein categorizing said impedance-based curve or optionally said cell index curve is based on short term and long term curves.

11. A method of categorizing a cell response to a biologically active agent comprising:
   a. providing a device for measuring cell-substrate impedance, wherein said device comprises at least two wells, further wherein said device is operably connected to an impedance analyzer;
   b. adding cells to said at least two wells;
   c. monitoring impedance of said at least two wells at time intervals over a time period and optionally determining cell indices from impedance values;
   d. introducing at least one biologically active agent to at least one and a control to another of said at least two wells, wherein said introduction occurs during said time period such that at least one of said impedance values is obtained prior to said introduction;
   e. generating an impedance-based curve and/or optionally a cell index curve for said biologically active agent and said control;
   f. comparing said impedance-based curves or optionally said cell index curves between said biologically active agent and said control; and if significantly different
   g. comparing said impedance-based curve or optionally said cell index curve of said biologically active agent to at least one predetermined mechanism-specific cellular response profile group, wherein said impedance-based curve or optionally said cell index curve is categorized into said group if sufficiently similar, further wherein said impedance-based curve or optionally said cell index curve is categorized into a different group if not sufficiently similar.

12. The method according to claim 11, wherein said device is in the format of a multi-well plate; wherein each well comprises said conductive electrode array.

13. The method according to claim 12, wherein said multi-well plate is selected from the group consisting of a 16 well plate, a 24 well plate, a 96 well plate, a 384 well plate, and a 1536 well plate.

14. The method according to claim 11, wherein said biologically active agent is selected from the group consisting of a compound, a peptide, a protein, an antibody or antibody fragment, an apatmer, a ribozyme, a siRNA, a miRNA, a nucleotide, an anti-sense oligo, a virus, a bacteria, a yeast, a mammalian cell, a non-mammalian cell, and a combination thereof.

15. The method according to claim 14, wherein said compound is selected from the group consisting of a DNA damaging agent, a protein tyrosine kinase inhibitor, a protein synthesis inhibitor, a nuclear receptor agonist and/or antagonist, a HDAC inhibitor, a proteasome inhibitor, a calcium pathway modulator, an anti-mitotic agent, a herbicide, a fungicide, an environmental toxicant, and an inhibitor or modulator of an enzyme or protein required for at least one selected from the group consisting of cell viability, cell adhesion, cell proliferation, apoptosis, and cell morphology.

16. The method according to claim 11, wherein said biologically active agent is selected from group consisting of an siRNA, an aptamer, an antisense oligo, and a reagent that serves to specifically "knock down" or "knock out" a protein or group of proteins of interest within the cell, further wherein said categorizing the cell responses to said biologically active agent into said at least one predetermined mechanism-specific cellular response profile group is for investigating protein or enzyme function within cells, the method further comprising:
   concluding that said protein or group of proteins of interest within cells may exhibit similar mechanism to a predetermined biologically active agent from which said one pre-determined mechanism-specific cellular response profile group is obtained.

17. The method according to claim 11, wherein said compound is selected from the group consisting of a primary cell, a cell line, and an engineered cell expressing specific proteins or sets of proteins.

18. The method according to claim 11, wherein comparing said impedance-based curve or optionally said cell index curve of said biologically active agent to at least one predetermined mechanism-specific cellular response profile group is based on short teiin curves.

19. The method according to claim 11, wherein comparing said impedance-based curve or optionally said cell index curve of said biologically active agent to at least one predetermined mechanism-specific cellular response profile group is based on long term curves.

20. The method according to claim 11, wherein comparing said impedance-based curve or optionally said cell index curve of said biologically active agent to at least one predetermined mechanism-specific cellular response profile group is based on short term and long term curves.

21. A method of categorizing responses to biologically active agents into groups, comprising:
   a. providing a device for measuring cell-substrate impedance, wherein said device comprises at least three wells, further wherein said device is operably connected to an impedance analyzer;
   b. adding cells to said at least three wells;
   c. monitoring impedance of said at least three wells over a time period and optionally determining cell indices from impedance values;
   d. introducing at least two biologically active agents, each to a different well of said at least three wells and introducing a control to another different well, wherein said introduction occurs during said time period such that at least one of said impedance values is obtained prior to said introduction;
   e. generating an impedance-based curve and/or optionally a cell index curve for each biologically active agent and said control;
   f. comparing said impedance-based curves or optionally said cell index curves to one another and categorizing said impedance-based curves or optionally cell index curves into one or more groups according to the presence or absence of at least one sufficient similarity.

22. The method according to claim 21, wherein said device comprises:
   a. a nonconductive substrate; and
   b. a conductive electrode array fabricated on said nonconductive substrate;
wherein said cell is capable of attaching to said electrode array.

23. The method according to claim 22, wherein said device is in the format of a multi-well plate; wherein each well comprises said conductive electrode array.

24. The method according to claim 23, wherein said multi-well plate is selected from the group consisting of a 16 well plate, a 24 well plate, a 96 well plate, a 384 well plate, and a 1536 well plate.

25. The method according to claim 21, wherein said biologically active agent is selected from the group consisting of a compound, a peptide, a protein, an antibody or antibody fragment, an aptamer, a ribozyme, a siRNA, a miRNA, a nucleotide, an anti-sense oligo, a virus, a bacteria, a yeast, a mammalian cell, a non-mammalian cell, and a combination thereof.

26. The method according to claim 25, wherein said compound is selected from the group consisting of a DNA damaging agent, a protein tyrosine kinase inhibitor, a protein synthesis inhibitor, a nuclear receptor agonist and/or antagonist, a HDAC inhibitor, a proteasome inhibitor, a calcium pathway modulator, an anti-mitotic agent, a herbicide, a fungicide, an environmental toxicant, and an inhibitor or modulator of an enzyme or protein required for at least one selected from the group consisting of cell viability, cell adhesion, cell proliferation, apoptosis, and cell morphology.

27. The method according to claim 21, wherein categorizing said impedance-based curves or optionally said cell index curves is based on short term curves.

28. The method according to claim 21, wherein categorizing said impedance-based curves or optionally said cell index curves is based on long term curves.

29. The method according to claim 21, wherein categorizing said impedance-based curves or optionally said cell index curves is based on short term and long term curves.

30. The method according to claim 21, wherein said impedance-based curves or optionally said cell index curves are categorized from between two groups and the total number of said biologically active agents.

31. The method according to claim 21, wherein said at least two biologically active agents comprise at least a first biologically active agent whose mechanism of action is predetermined, said method further comprising concluding that biologically active agents categorized into the group containing said first biologically active agent may have similar mechanism of action on cells to that of said first biologically active agent.

32. The method according to claim 21, wherein said similarities of impedance-based curves or optionally cell index curves are calculated from correlation coefficients between two curves being compared.

33. The method according to claim 21, wherein said similarities of impedance-based curves or optionally cell index curves are calculated from differences from single characteristic parameters derived for each curve.

34. The method according to claim 21, wherein said similarities of impedance-based curves or optionally cell index curves are calculated from the distance between two curves.

35. The method according to claim 21, wherein said comparing and categorizing is performed using a curve classification algorithm.

* * * * *